US012688916B2

(12) United States Patent
Mellinger et al.

(10) Patent No.: US 12,688,916 B2
(45) Date of Patent: Jul. 21, 2026

(54) BIOMARKER BASED NICOTINE REPLACEMENT THERAPY

(71) Applicant: McNeil AB, Helsingborg (SE)

(72) Inventors: Justin Mellinger, Philadelphia, PA (US); Ryan Walsh, Downingtown, PA (US); Sophie Edgar, Hoboken, NJ (US); Ming Dong, Hoboken, NJ (US); Curt Binner, Furlong, PA (US)

(73) Assignee: McNeil AB, Helsingborg (SE)

( * ) Notice: Subject to any disclaimer, the term of this patent is extended or adjusted under 35 U.S.C. 154(b) by 737 days.

(21) Appl. No.: 17/244,709

(22) Filed: Apr. 29, 2021

(65) Prior Publication Data

US 2021/0338948 A1     Nov. 4, 2021

Related U.S. Application Data

(60) Provisional application No. 63/018,035, filed on Apr. 30, 2020.

(51) Int. Cl.
| | |
|---|---|
| *G16H 20/13* | (2018.01) |
| *A24F 40/50* | (2020.01) |
| *A24F 47/00* | (2020.01) |
| *A61B 5/11* | (2006.01) |

(Continued)

(52) U.S. Cl.
CPC .............. *G16H 20/13* (2018.01); *A24F 40/50* (2020.01); *A24F 47/00* (2013.01); *A61B 5/1118* (2013.01); *A61M 15/06* (2013.01); *G16H 20/10* (2018.01)

(58) Field of Classification Search
CPC ....... G16H 10/00–80/00; A24F 1/00–2700/08; A61B 5/1118; A61M 15/06; G05B 1/00–2223/06
See application file for complete search history.

(56) References Cited

U.S. PATENT DOCUMENTS

| | | | |
|---|---|---|---|
| 7,530,352 B2 | 5/2009 | Childers et al. | |
| 8,210,403 B2 | 7/2012 | Malorni et al. | |
| 10,206,572 B1 | 2/2019 | Utley et al. | |

(Continued)

FOREIGN PATENT DOCUMENTS

| | | | | |
|---|---|---|---|---|
| CN | 211353944 U | * | 8/2020 | |
| EP | 1 165 164 B1 | | 6/2004 | |

(Continued)

OTHER PUBLICATIONS

Chatterjee et al., "mCrave: Continuous Estimation of Craving During Smoking Cessation," UBICOMP '16, Sep. 12-16, 2016, Heidelberg, Germany; http://dx.doi.org/10.1145/2971648.2971672. (Year: 2016).*

(Continued)

*Primary Examiner* — Jonathon A. Szumny

(74) *Attorney, Agent, or Firm* — Condo Roccia Koptiw LLP

(57) ABSTRACT

A device for providing nicotine replacement therapy may be provided. The device may comprise a processor. The processor may be configured to perform one or more actions. A cessation program for a user may be determined. A program intervention event based on a phase of the cessation program may be determined. A marker associated with the user may be determined. A modification to the cessation program may be determined based on the program intervention event.

16 Claims, 42 Drawing Sheets

(51) Int. Cl.
    *A61M 15/06*        (2006.01)
    *G16H 20/10*        (2018.01)

(56)          References Cited

U.S. PATENT DOCUMENTS

| | | | |
|---|---|---|---|
| 12,171,275 B2 * | 12/2024 | Utley | A61B 5/14551 |
| 2005/0098173 A1 | 5/2005 | Childers et al. | |
| 2007/0045288 A1 | 3/2007 | Nelson | |
| 2011/0182831 A1 * | 7/2011 | Gonda | A61K 31/465 |
| | | | 424/45 |
| 2011/0182918 A1 * | 7/2011 | Kalnik | A61P 25/34 |
| | | | 435/7.92 |
| 2011/0263947 A1 | 10/2011 | Utley et al. | |
| 2011/0270053 A1 | 11/2011 | Utley et al. | |
| 2012/0072231 A1 * | 3/2012 | Mayer | G16H 20/10 |
| | | | 705/2 |
| 2013/0319439 A1 | 12/2013 | Gorelick et al. | |
| 2014/0190496 A1 * | 7/2014 | Wensley | A61M 11/042 |
| | | | 131/273 |
| 2015/0216237 A1 * | 8/2015 | Wensley | A24F 40/48 |
| | | | 131/273 |
| 2015/0245662 A1 | 9/2015 | Memari et al. | |
| 2016/0150824 A1 | 6/2016 | Memari et al. | |
| 2016/0157524 A1 | 6/2016 | Bowen et al. | |
| 2016/0158782 A1 | 6/2016 | Henry et al. | |
| 2016/0164484 A1 | 6/2016 | Madan et al. | |
| 2016/0219931 A1 | 8/2016 | Doshi et al. | |
| 2016/0331027 A1 | 11/2016 | Cameron | |
| 2017/0039045 A1 * | 2/2017 | Abrahami | A61B 5/486 |
| 2017/0055573 A1 * | 3/2017 | Utley | A61B 5/0816 |
| 2017/0189629 A1 | 7/2017 | Newberry | |
| 2017/0213014 A1 * | 7/2017 | Su | A61B 5/1123 |
| 2017/0262064 A1 * | 9/2017 | Ofir | A61B 5/11 |
| 2017/0266397 A1 | 9/2017 | Mayle et al. | |
| 2018/0001084 A1 * | 1/2018 | Imran | A61K 31/465 |
| 2018/0068080 A1 * | 3/2018 | Parate | G16H 20/70 |
| 2018/0075219 A1 * | 3/2018 | Klein | G16H 20/70 |
| 2018/0358117 A1 * | 12/2018 | Neagle | A61B 5/0015 |
| 2019/0158938 A1 * | 5/2019 | Bowen | A61M 15/06 |
| 2019/0209546 A1 | 7/2019 | Myers et al. | |
| 2019/0221297 A1 * | 7/2019 | Satake | G16H 20/00 |
| 2019/0261855 A1 * | 8/2019 | Utley | A61B 5/7242 |
| 2020/0107586 A1 | 4/2020 | Althorpe et al. | |
| 2020/0229508 A1 * | 7/2020 | Israel | A24F 40/65 |
| 2021/0130153 A1 | 5/2021 | Scott et al. | |
| 2021/0153556 A1 | 5/2021 | Lewis et al. | |
| 2021/0260312 A1 | 8/2021 | Lacour-gayet et al. | |
| 2021/0337881 A1 | 11/2021 | Mellinger et al. | |
| 2021/0346617 A1 * | 11/2021 | Wagner | H01R 13/26 |

| | | | |
|---|---|---|---|
| 2022/0059119 A1 * | 2/2022 | Varughese | G10L 15/22 |
| 2022/0061399 A1 | 3/2022 | Ferrie et al. | |
| 2025/0107571 A1 | 4/2025 | Choukroun et al. | |

FOREIGN PATENT DOCUMENTS

| | | | | |
|---|---|---|---|---|
| JP | 2004148117 A | | 5/2004 |
| JP | 2008543353 A | | 12/2008 |
| JP | 2013162975 A | * | 8/2013 |
| JP | 2016523979 A | | 8/2016 |
| KR | 2017-0026520 A | | 3/2017 |
| RU | 2 707 893 C2 | | 12/2019 |
| WO | 00/054828 A1 | | 9/2000 |
| WO | 00/54828 A1 | | 9/2000 |
| WO | 0193932 A1 | | 12/2001 |
| WO | 2015/006652 A1 | | 1/2015 |
| WO | 2016001923 A2 | | 1/2016 |
| WO | 2016/145373 A1 | | 9/2016 |
| WO | 2016/164484 A1 | | 10/2016 |
| WO | 2017/056103 A1 | | 4/2017 |
| WO | 2018024155 A1 | | 2/2018 |
| WO | 2019/074942 A1 | | 4/2019 |
| WO | 2019/104223 A1 | | 5/2019 |
| WO | 2020006311 A1 | | 1/2020 |
| WO | 2020/037226 A1 | | 2/2020 |
| WO | 2021222625 A1 | | 11/2021 |
| WO | 2021222617 A3 | | 12/2021 |

OTHER PUBLICATIONS

Ortis et al., "A Report on Smoking Detection and Quitting Technologies," Int. J. Environ. Res. Public Health 2020, 17, 2614; doi: 10.3390/ijerph17072614. (Year: 2020).*

Sandberg, et al., "Assessing Recent Smoking Status by Measuring Exhaled Carbon Monoxide Levels", https://www.ncbi.nlm.nih.gov/pmc/articles/PMC3241681/, Dec. 16, 2011, 7 pages.

Linneberg, et al., "Effect of Smoking on Blood Pressure and Resting Heart Rate", https://www.ahajournals.org/doi/full/10.1161/CIRCGENETICS.115.001225, Dec. 2015, 10 pages.

Minami, et al., "Effects of Smoking Cessation on Blood Pressure and Heart Rate Variability in Habitual Smokers", https://pubmed.ncbi.nlm.nih.gov/9931170/, Jan. 1999, 8 pages.

Stein, et al., "Effect of 21 mg Transdermal Nicotine Patches and Smoking Cessation on Heart Rate Variability", https://www.ajconline.org/article/S0002-9149(97)89203-X/pdf , Apr. 1, 1996, 5 pages.

Harte, et al., "Effects of Smoking Cessation on Heart Rate Variability Among Long-Term Male Smokers", https://link.springer.com/article/10.1007/s12529-013-9295-0 Feb. 9, 2013, 8 pages.

Papathanasiou, et al., "Effects of smoking on heart rate at rest and during exercise, and on heart rate receovery, in young adults", https://pubmed.ncbi.nlm.nih.gov/23685653/ May-Jun. 2013, 10 pages.

\* cited by examiner

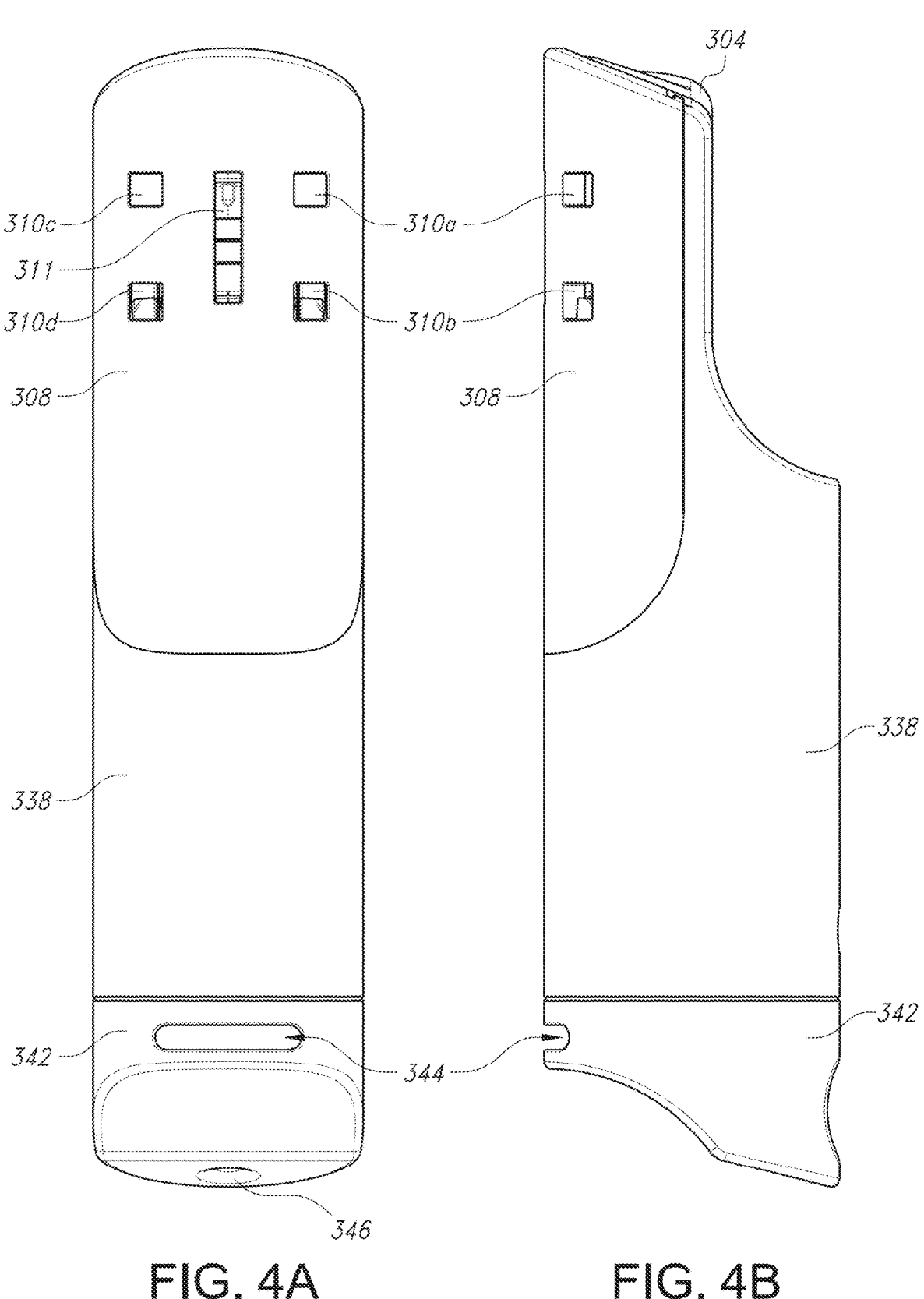
FIG. 4A             FIG. 4B

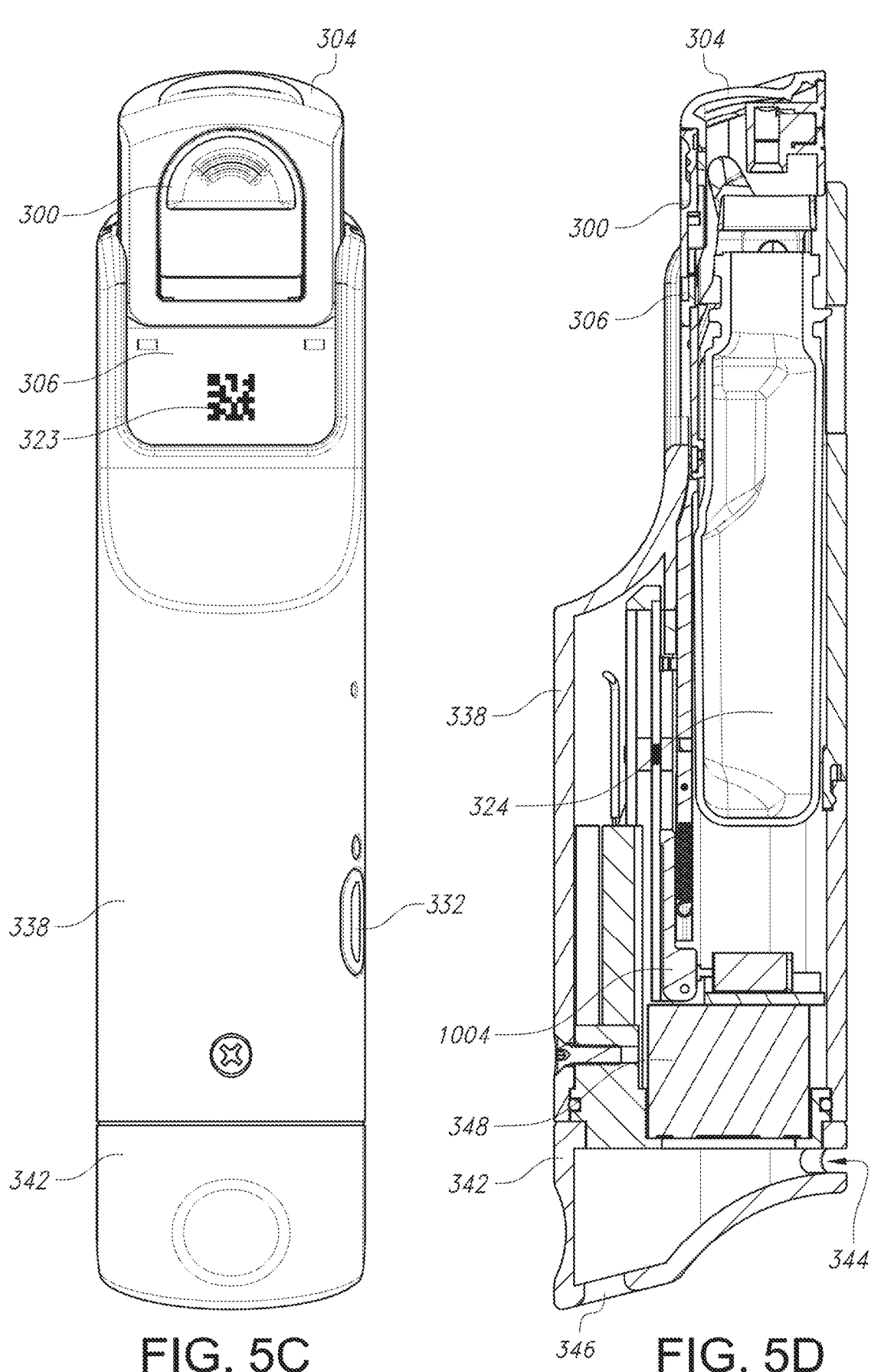
FIG. 5C        FIG. 5D

FIG. 8A                  FIG. 8B

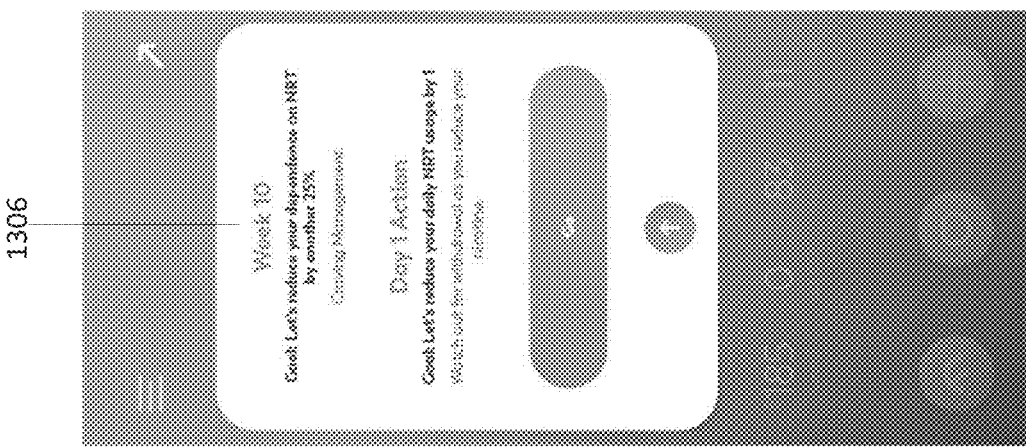
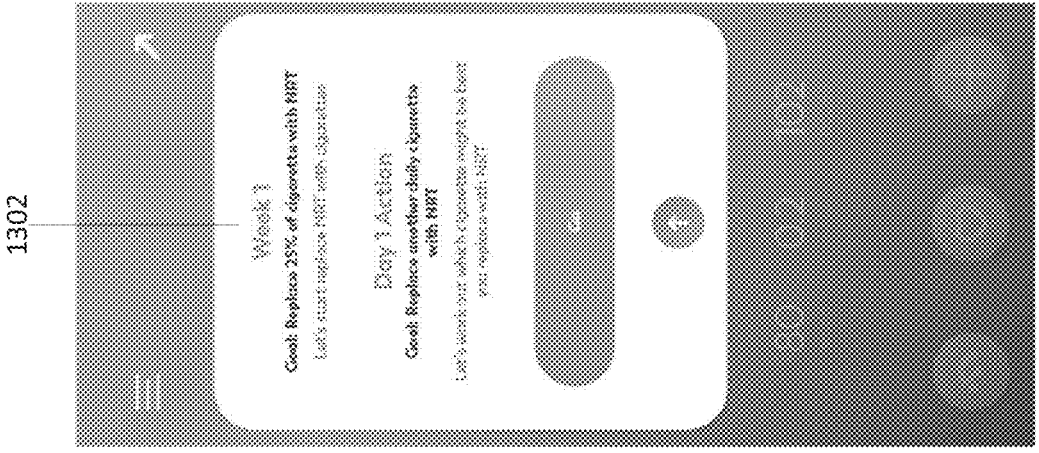
FIG. 13

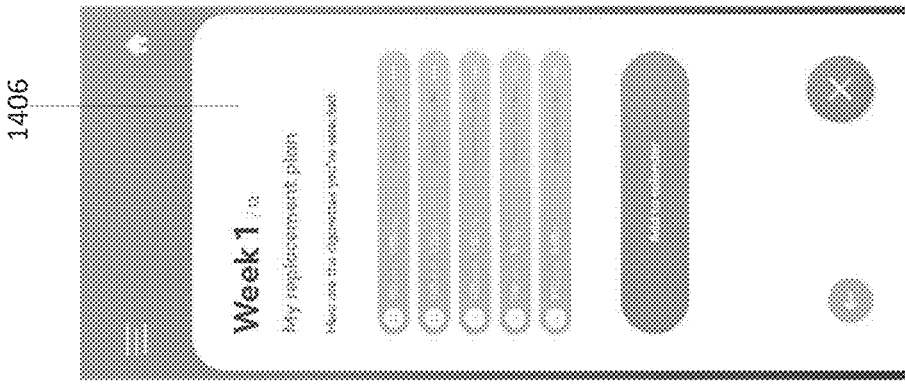
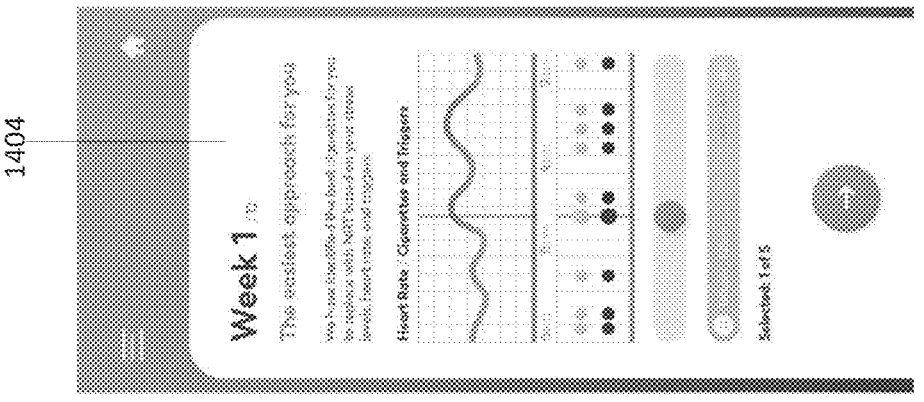
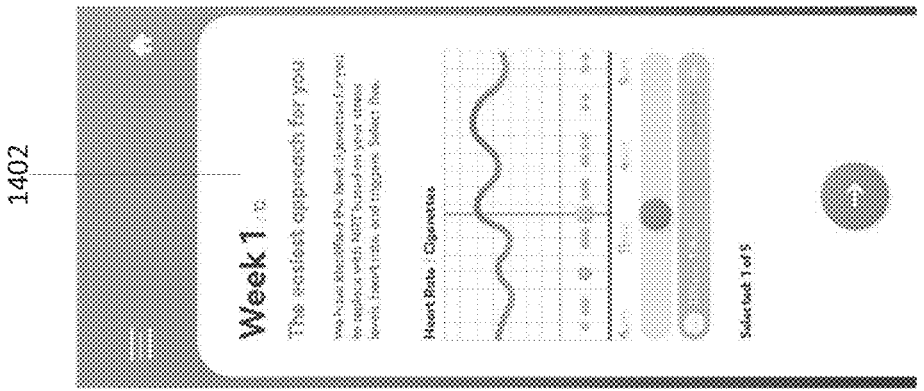
FIG. 14

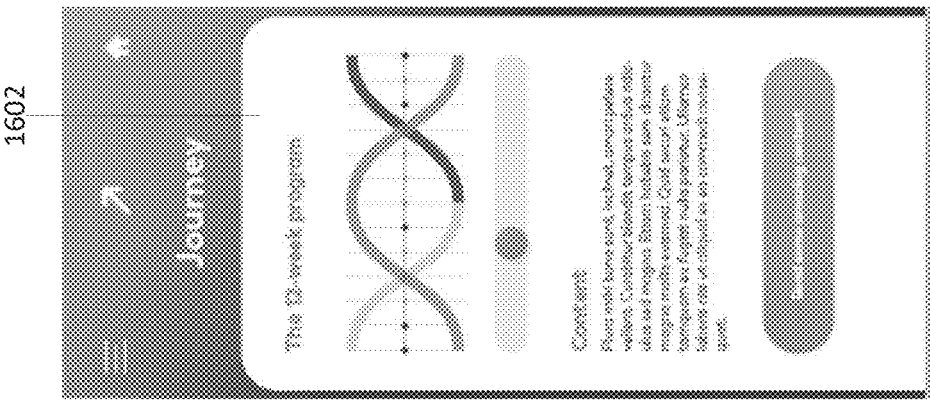
FIG. 16A
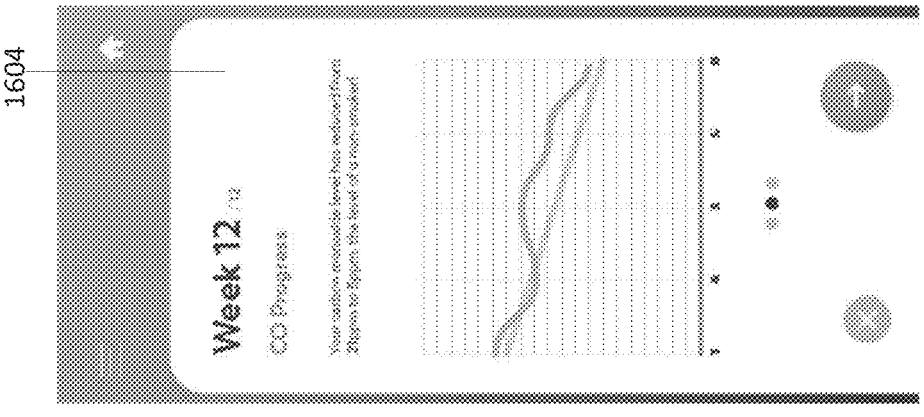
FIG. 16B
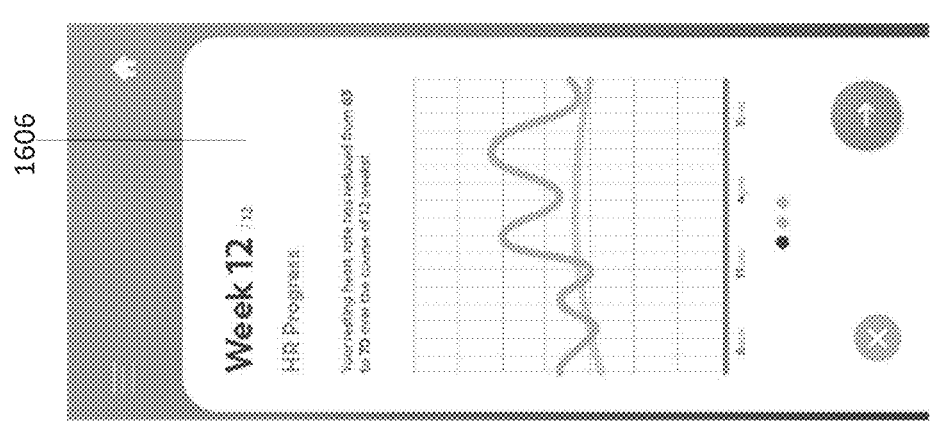
FIG. 16C

|  | Week -3 to 0 | Week 1 | Week 2 | Week 3 | Week 4 | Week 5 | Week 6 | Week 7 | Week 8 | Week 9 | Week 10 | Week 11 | Week 12 |
|---|---|---|---|---|---|---|---|---|---|---|---|---|---|
| Cigarette | No Reduction | 50% Cigarette Reduction | 25% Cigarette Reduction | 75% Cigarette Reduction | 100% Cigarette Reduction | 0% Cigarette Usage | 0% Cigarette Usage | 0% Cigarette Usage | 0% Cigarette Usage | 0% Cigarette Usage | 0% Cigarette Usage | 0% Cigarette Usage | 0% Cigarette Usage |
| NRT | No Treatment | 25% NRT usage | 50% NRT usage | 75% NRT usage | 100% NRT usage | 100% NRT usage | 100% NRT usage | 100% NRT usage | 100% NRT usage | 25% NRT reduction | 50% NRT reduction | 75% NRT reduction | 100% NRT reduction |

FIG. 21

| Inputs | | | Outputs | Craving PPV (Positive Predictive Value) |
|---|---|---|---|---|
| GSR | HR | Skin Temp | | |
| UP | UP | UP | CRAVING | 66.67% |
| UP | UP | DOWN | CRAVING | 33.33% |
| UP | DOWN | DOWN | NOT CRAVING | 0.00% |
| UP | DOWN | UP | CRAVING | 33.33% |
| DOWN | DOWN | UP | CRAVING | 66.67% |
| DOWN | UP | DOWN | CRAVING | 66.67% |
| DOWN | UP | UP | CRAVING | 100.00% |
| DOWN | DOWN | DOWN | CRAVING | 33.33% |

3112　3114　3116

3104

Biomarkers 3106　3108　3110

GSR　Skin Temp　HR

Craving Detection Event

3102

| Inputs | | | Outputs |
|---|---|---|---|
| RHR | HRV | BP | |
| UP | UP | UP | EXTEND |
| UP | UP | DOWN | EXTEND |
| UP | DOWN | DOWN | EXTEND |
| UP | DOWN | UP | EXTEND |
| DOWN | DOWN | UP | EXTEND |
| DOWN | UP | DOWN | ON TRACK |
| DOWN | UP | UP | EXTEND |
| DOWN | DOWN | DOWN | EXTEND |

3240

3218

Cigarette Reduction Phase

| | Inputs Week 1-4 | | Outputs |
|---|---|---|---|
| CS | NRT | CO | |
| UP | UP | UP | EXTEND |
| UP | UP | DOWN | N/A |
| UP | DOWN | DOWN | N/A |
| UP | DOWN | UP | EXTEND |
| DOWN | DOWN | UP | N/A |
| DOWN | UP | DOWN | ON TRACK |
| DOWN | UP | UP | N/A |
| DOWN | DOWN | DOWN | TRUNCATE |

Stabilization Phase

| | Inputs Week 5-8 | | Outputs |
|---|---|---|---|
| CS | NRT | CO | |
| UP | UP | UP | EXTEND |
| UP | UP | DOWN | N/A |
| UP | DOWN | DOWN | N/A |
| UP | DOWN | UP | EXTEND |
| DOWN | DOWN | UP | N/A |
| DOWN | UP | DOWN | EXTEND |
| DOWN | UP | UP | N/A |
| DOWN | DOWN | DOWN | TRUNCATE |

NRT Reduction Phase

| | Inputs Week 9-12 | | Outputs |
|---|---|---|---|
| CS | NRT | CO | |
| UP | UP | UP | EXTEND |
| UP | UP | DOWN | N/A |
| UP | DOWN | DOWN | N/A |
| UP | DOWN | UP | EXTEND |
| DOWN | DOWN | UP | N/A |
| DOWN | UP | DOWN | EXTEND |
| DOWN | UP | UP | N/A |
| DOWN | DOWN | DOWN | ON TRACK |

3502
A cessation program may be determine for a user.

3504
A program intervention event and/or a marker associated with the user may be determined.

3506
A modification to the cessation program may be determined.

3600

BIOMARKER BASED NICOTINE REPLACEMENT THERAPY

CROSS-REFERENCE TO RELATED APPLICATIONS

This application claims the benefit of U.S. Provisional Application No. 63/018,035, filed Apr. 30, 2020, the contents of which are incorporated by reference in their entirety herein.

BACKGROUND

Smokers, other tobacco users and electronic cigarette users often use tobacco or nicotine products due to a nicotine addiction. Specifically, the users will often use these products even in the face of negative health consequences due to a biological and/or phycological dependence on nicotine. And some of these users wish to quit. But due to their nicotine addiction, these users may not be able to successfully quit.

SUMMARY

A device for providing nicotine replacement therapy may be provided. The device may comprise a dispenser for dispensing a nicotine formulation. The device may comprise an actuating member mounted to actuate the dispenser. The device may comprise a lockout mechanism that may be movable between an operative position that may allow the actuating member to move so as to actuate the dispenser, and a non-operative position that may prevent the actuating member from moving. The device may comprise a processor. The processor may be configured to determine an amount of nicotine that was previously consumed by a user. The processor may be configured to send a lockout mechanism signal to the lockout mechanism that causes the lockout mechanism to move to the non-operative position.

A device for providing nicotine replacement therapy may be provided. The device may comprise a memory and a processor. The processor may be configured to perform a method. It may be determined that a user is experiencing a nicotine craving. An amount of nicotine that was previously consumed by the user may be determined. A nicotine threshold for the user may be determined. It may be determined that the amount of nicotine that was previously consumed by the user is below the nicotine threshold. A message may be sent to advise the user to dispense a dose of nicotine to reduce the nicotine craving.

A device for providing nicotine replacement therapy may be provided. The device may comprise a dispenser body. The device may comprise a dispenser for dispensing a dosage of a nicotine formulation. The device may comprise an actuating member mounted to actuate the dispenser. The device may comprise a carriage mounted to move relative to the dispenser body when contacted by the actuating member. The device may comprise a sensor configured to sense a movement of the carriage. The device may comprise a processor. The processor may be configured to perform one or more actions. It may be determined that a dosage of the nicotine formulation was dispensed based on a signal from the sensor. An indication of the dosage of the nicotine formulation may be sent.

A device for providing nicotine replacement therapy may be provided. The device may comprise a processor. The processor may be configured to perform one or more actions. A cessation program for a user may be determined. A program intervention event based on a phase of the cessation program may be determined. A marker associated with the user may be determined. A modification to the cessation program may be determined based on the program intervention event.

A device for providing nicotine replacement therapy may be provided. The device may comprise a processor that may be configured to perform one or more actions. A phase of a cessation program associated with a user may be determined. A smoking detection event based on a biomarker associated with the user may be determined. A modification to the cessation program may be determined based on the phase and the smoking detection event.

A device for providing nicotine replacement therapy may be provided. The device may comprise a processor. The processor may be configured to determine a phase of a cessation program associated with a user. A nicotine consumption detection event may be determined. A modification to the cessation program may be determined based on the phase and the nicotine consumption detection event.

A device for providing nicotine replacement therapy may be provided. The device may comprise a processor. A biomarker associated with a user may be determined. A nicotine craving may be detected using the biomarker associated with the user. An intervention may be provided to the user based on the nicotine craving.

A smart nicotine replacement therapy (NRT) device may include one or more integrated mechanical and/or biological sensors. For example, the device may include one or more mechanisms for detection of nicotine use, fidget detection, location detection, receiving replaceable vial, authenticating vial and/or dose tracking. One or more applications operated on the device or other device(s), may provide a dynamic personalized journey guide based on usage, sensor-based data, biological, behavioral response data to aid in cessation of cigarettes, electronic cigarettes, tobacco and use of nicotine. The smart NRT device may be used in combination with a smart phone and/or a smart watch to provide tools to monitor and adjust the smoke cessation journey.

The smart NRT device may include a sensor for measuring a physiological parameter. For example, the smart NRT device may include a carbon monoxide (CO) sensor for measuring the CO level of the user. A CO measurement may be taken, for example, via the smart NRT device or another device, during the smoking cessation program. User CO level information may be used to provide real-time feedback to a user, indicating that the smoking cessation is providing meaningful biological benefit.

The NRT device may be used in conjunction with a smart watch for obtaining information such as biomarker information. A biomarker may be a heart rate, heart rate variability, blood pressure, temperature, respiration rate, oxygen saturation, carboxyhemoglobin, carbon monoxide, galvanic skin response (GSR), location, user gesture, movement and/activity, and/or the like. Potential smoking cravings may be determined based on the information obtained from the NRT device, the smart watch, and/or a smart phone. A suggestion message for NRT use may be generated in advance of a craving.

The user's smoking behavior or nicotine addiction may be determined based on real time feedback of biological indicators, biomarkers, and/or behavioral support elements. The feedback information may be used to adapt the user's smoking cessation plan during a quit attempt.

A craving may be a desire for more of a substance or activity consisting of a desire to experience the euphoric (or other) effects. A craving may include a desire to avoid the withdrawal aspects of abstinence. A craving may be a desire to consume a particular substance, such as nicotine.

A device for providing nicotine replacement therapy (e.g., the smart NRT device) may include a dispenser for dispensing a nicotine formulation and an actuating member mounted to actuate the dispenser. The device may include a lockout mechanism movable between an operative position that may allow the actuating member to move to actuate the dispenser, and a non-operative position that may prevent the actuating member from moving. The device may include one or more processors as described therein. The device may include a sensor for measuring a physiological parameter. For example, the device may include a CO sensor. The user's CO level may be determined, and an indication of the CO level may be sent (e.g., to a processor, or to another device via a transmitter). The device may include one or more sensors for sensing one or more physiological parameters of the user. The sensors may include one or more of photoplethysmogram (PPG) sensor, carbon monoxide sensor, volatile organic compounds (VOCs) sensor, spirometer sensor, electrocardiogram (EKG) sensor, galvanic skin response sensor, temperature sensor, pressure sensor and/or the like.

The device may include a processor configured to determine whether or not to send a signal to the lockout mechanism to cause the lockout mechanism to move either to the non-operative position or to the operative position depending on the age of a user, the user's geographic location, and/or an amount of nicotine that was previously consumed by the user. For example, the lockout mechanism that causes the lockout mechanism to move to the non-operative position may be sent upon determining that the amount of nicotine that was previously consumed by the user exceeds a nicotine threshold. The nicotine threshold may be personalized based on various data gathered via the NRT device, and/or other device(s) connected with the NRT device.

The device may include a dispense tracking detection mechanism for detecting and tracking the number of sprays. The device may include a mechanism to measure a dosage of the nicotine formulation dispensed associated with a pump or a spray. The dispense tracking mechanism may include a proximity sensor. For example, the device may include a carriage (e.g., magnetic carriage) mounted to move relative to the dispenser when contacted by the actuating member and a sensor (e.g., a magnetic sensor) configured to sense a movement of the carriage. The magnetic sensor may detect when the magnetic carriage is within a range. The dosage of the nicotine formulation that was dispensed may be determined based on a signal from the sensor. An indication of the dosage may be sent (e.g., to the processor in the device, or to another device via a transmitter). The device may include a transmitter for sending a signal indicating the amount of nicotine formulation consumed by the user.

The device may include a receiver for receiving a signal indicating that the lockout mechanism is to be moved to the non-operative position (e.g., a lockout activation message) and/or a signal indicating that the lockout mechanism is to be moved to the operative position (e.g., a use resume message). The signals may be received from a smart phone, a smart watch, and/or anther device.

Whether a user is experiencing a nicotine craving may be determined, and a message may be sent or displayed to advise the user to dispense a dose of nicotine formulation to reduce the nicotine craving. A message may be sent to instruct the nicotine delivery device to allow the dose nicotine to be dispensed. A potential nicotine craving may be determined based on at least one of a detected motion, a physical location, a time of day, a scheduled activity, a calendar of the user, social media data, a biometric measurement (e.g., a resting heart rate, real-time heart rate data, skin temperature, etc.), triggers entered by the user, and/or triggers derived based on various data.

BRIEF DESCRIPTION OF THE DRAWINGS

FIGS. 4A-D depict perspective views of the smart NRT device with a dispenser head in a non-operative (e.g., locked position).

FIGS. 5A-D depict perspective views of the smart NRT device with the dispenser head in an operative position (e.g., unlocked position).

FIG. 13 depicts example user interface(s) for indicating personalized weekly and/or daily targets and recommended actions.

FIG. 14 depicts example user interface(s) for creating a personalized cigarette replacement plan.

FIG. 16A depicts an example overview of a nicotine/smoking cessation program.

FIG. 16B depicts an example user interface for providing feedback on carbon monoxide level information gathered and tracked throughout the program.

FIG. 16C depicts an example user interface for providing feedback on heart rate information gathered and tracked throughout the program.

FIG. 21 depicts an example 12-week NRT journey that may be customized based on sensor feedback.

FIGS. 32B-32C depict example tables for determining a program intervention event.

DETAILED DESCRIPTION

Nicotine replacement therapy (NRT) is a process to mitigate the difficult withdrawal symptoms that are associated with cigarette smoking cessation and/or nicotine quit. NRT does this by replacing the nicotine from a cigarette, tobacco product or electronic cigarette with nicotine from an alternate source, such as a skin patch, chewing gum, nasal spray, inhaler, lozenge/tablet, oral spray, and the like. NRT has been shown to improve the likelihood of a successful smoking cessation and/or nicotine quit journey.

Figures 1A, 1B:
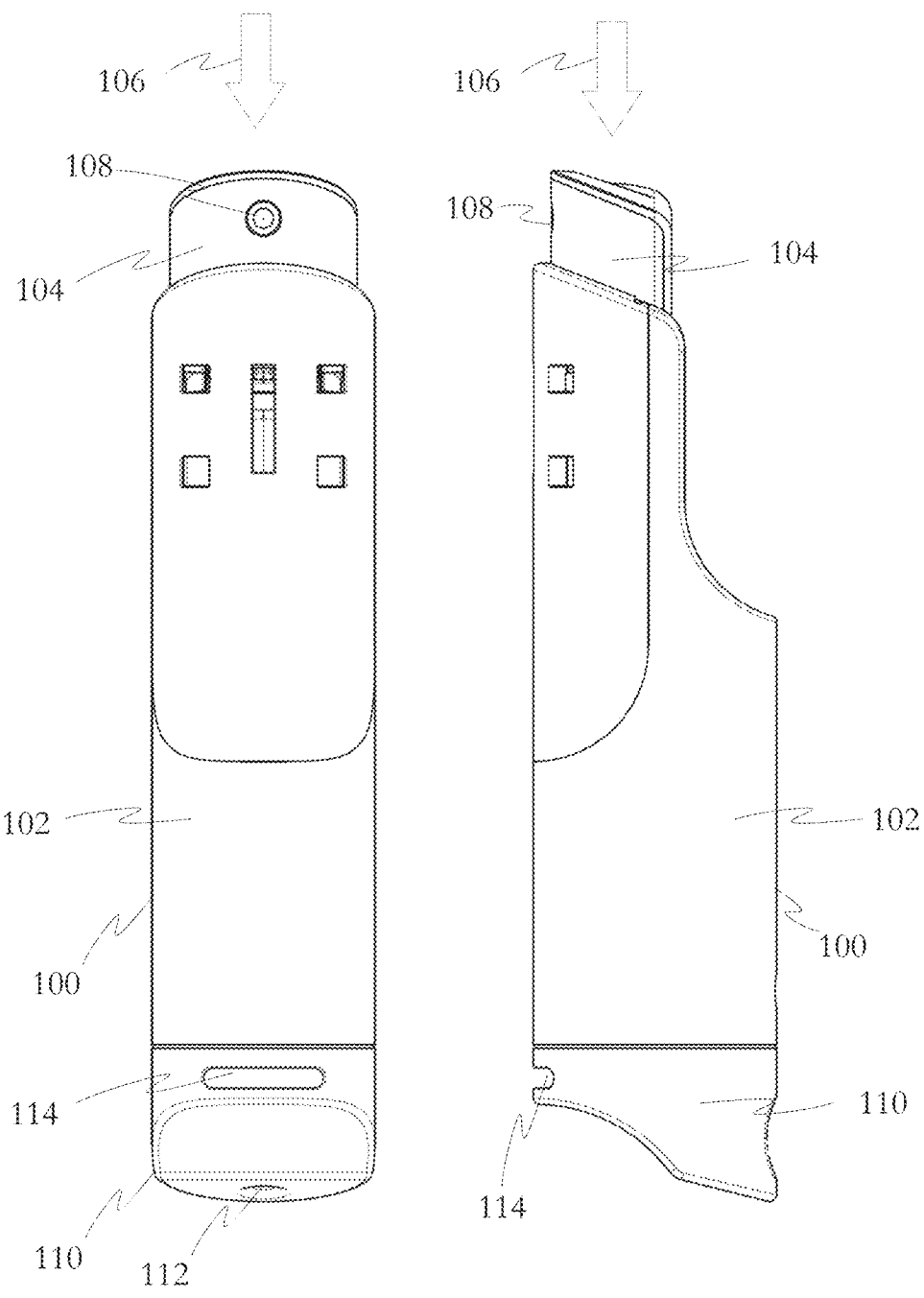
FIGS. 1A-B depict an example smart nicotine replacement therapy (NRT) device in front and side views respectively.

FIGS. 1A and 1B depict an example NRT device 100, in front and side views respectively. The device 100 may be or may include a nicotine oral spray device. To receive a dose of nicotine, the user grips the body 102 of the device 100 and depresses the actuator 104 (in the direction shown by arrow 106) while aiming the nozzle 108 to direct a mist of a nicotine formulation under the user's tongue, for example. The example NRT device 100 may include mechanical features such as a child-safe actuator and an internal, replaceable vial for holding the liquid, nicotine formulation.

The example NRT device 100 may further include certain digital-computing features to improve the modification of smoking behavior and nicotine addiction, for example. The NRT device 100 may include advanced features such as digital processing, communications, sensors, electro-mechanical interaction, user feedback, and the like. For example, the NRT device 100 may include a carbon monoxide (CO) sensor (not shown) integrated in the device 102. To use it, the user may press their lips around the mouthpiece 110 and exhale, expiring air from the lungs through the device's inlet 112, past the internal CO sensor, and out the outlet 114. The CO sensor may measure the relative concentration of CO in the person's expired air. The relative concentration of CO in a person's expired air may be indicative of magnitude of that person's cigarette smoking behavior. And it is a very useful datum for tracking and adapting a person's smoking and/or nicotine cessation/quit journey.

The NRT device 100, with such digital-computing features, may be incorporated into a broader system to further improve the modification of smoking behavior and nicotine addiction. This system may include aspects such as smart phone applications, wearable technology (e.g., smart watch) with biometric and activity tracking, cloud processing, predictive algorithms, adaptive algorithms, and the like. This system, for example, may be a closed loop NRT cessation system. And it may include the NRT device 100 with an integrated CO sensor, mechanisms for dosing detection, fidget detection, location determination, replaceable-vial authentication, dose concentration tracking, and the like. A corresponding NRT application and/or behavioral-support application (e.g., smartphone app, smart watch app, tablet app, and/or PC-based app), which may be used in combination with a smartwatch with biological sensors collecting information (e.g., biomarkers) about activity, heart rate, heart rate variability and the like, may provide the user with a dynamic, personalized journey guide. The guide may be based on the collected usage data, sensor data, biological data, behavioral response data, and the like. The guide may be supported by adaptive and/or predictive algorithms to leverage this data to adjust the planned cessation journey and/or to anticipate events, like cravings, for example—making the device 100 part of a cohesive toolkit for monitoring the use of nicotine and correspondingly adjusting a particular user's cessation journey. Such a device 100 and/or system may help the individual properly use nicotine replacements, aid in the adherence and compliance to a planned NRT journey or NRT quit journey, and ultimately drive a smoke-free success and/or nicotine cessation.

Figure 1C:
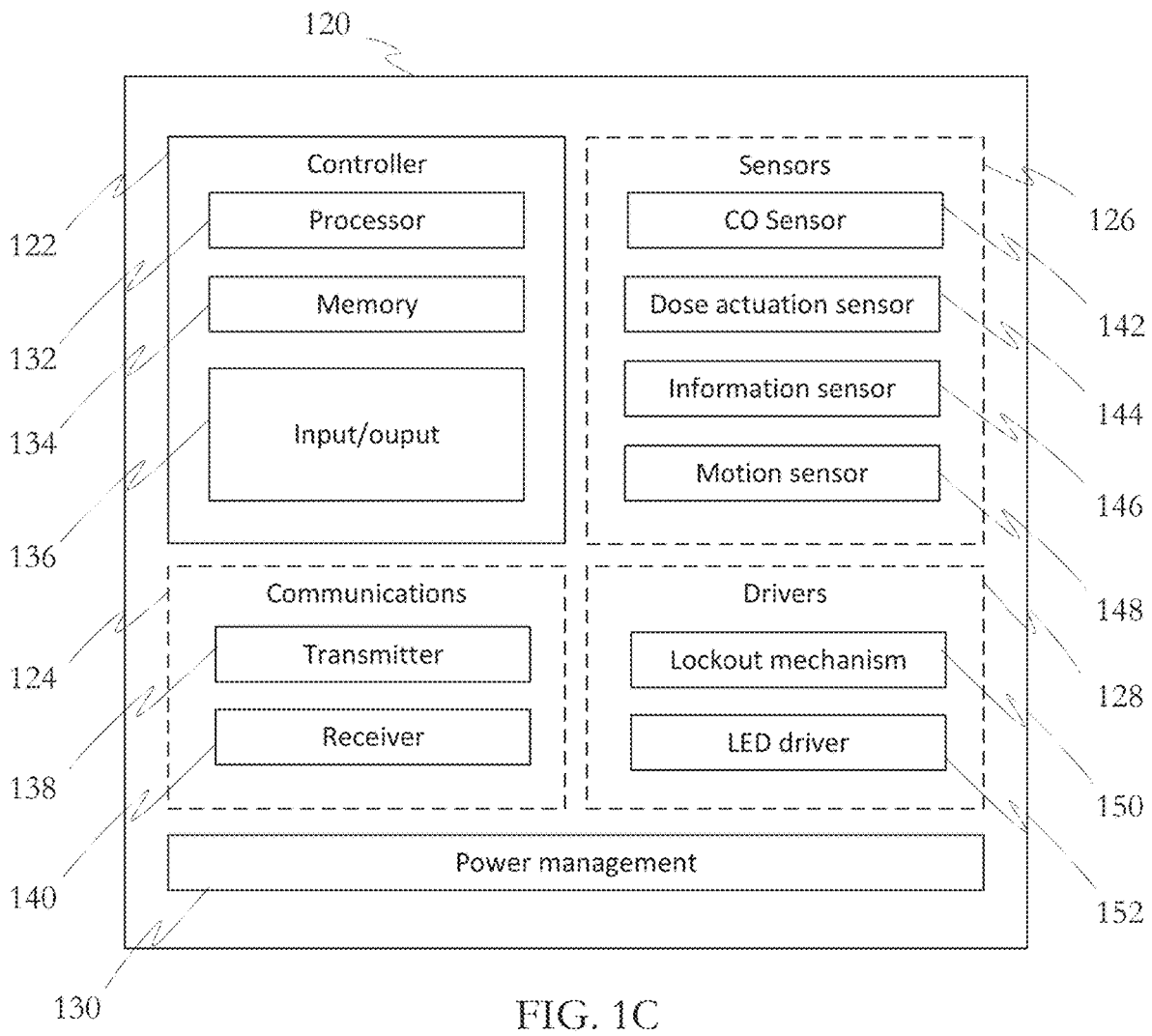
FIG. 1C is a functional block diagram of certain electrical components of the example smart NRT device.

FIG. 1C is a functional block diagram of certain electrical components 120 of the example NRT device 100. These components 120 may be incorporated into a handheld nicotine dispensing device, such as device 100. Such a dispenser may include a dispenser body and a mechanism for dispensing a nicotine replacement. For example, the dispenser may be operable to switch between an operative configuration and the non-operative configuration. For example, in the non-operative configuration, the lockout mechanism in the device may be activated to prevent nicotine formulation from being dispensed. The components 120 may integrate sensing, electromechanical driving, communications, and digital-processing functionality to the structure and operation of the dispenser. In examples, the components 120 may include a controller 122, communications interfaces 124, sensors 126, electrical and electromechanical drivers 128, and a power management subsystem 130.

The controller 122, may include a processor 132, a memory 134, and one or more input/output devices 136, for example. The controller 122 may be any suitable microcontroller, microprocessor, field programmable gate array (FPGA), application specific integrated circuit (ASIC), or the like, that is suitable for receiving data, computing, storing, and driving output data and/or signals. The controller 122 may be a device suitable for an embedded application. For example, the controller 122 may include a system on a chip (SOC).

The processor 132 may include one or more processing units. The processor 132 may be a processor of any suitable depth to perform the digital processing requirements disclosed herein. For example, the processor 132 may include a 4-bit processor, a 16-bit processor, a 32-bit processor, a 64-bit processor, or the like.

The memory 134 may include any component or collection of components suitable for storing data. For example, the memory 134 may include volatile memory and/or non-volatile memory. The memory 134 may include random-access memory (RANI), read-only memory (ROM), erasable programmable read-only memory (EPROM), (electrically erasable programmable read-only memory) EEPROM, flash memory, or the like.

The input/output devices 136 may include any devices suitable for receiving and/or sending information. This information may be in the form of digitally encoded data (from other digital components, for example) and/or analog data (from analog sensors, for example). The input/output devices 136 may include devices such as serial input/output ports, parallel input/output ports, universal asynchronous receiver transmitters (UARTs), discrete logic input/output pins, analog-to-digital converters, digital-to-analog converters. The input/output devices 136 may include specific interfaces with computing peripherals and support circuitry, such as timers, event counters, pulse width modulation (PWM) generators, watchdog circuits, clock generators, and the like. The input/output devices 136 may provide communication within and among the components 100, for example, communication between the controller 122 and the sensors 126, between the controller 122 and the drivers 128, between the controller 122 and the communications interfaces 124, and between the controller and the power management subsystem 130, and as a conduit for any other combination of components 120. The components 120 may support direct communication as well, for example, between a sensor 126 and the power management system 130.

The communications interfaces 124 may include a transmitter 138 and/or a receiver 140. Communication interfaces 124 may include one or more transmitters 138 and/or receivers 140. The transmitter 138 and receiver 140 may include any electrical components suitable for communication to and/or from the electrical components 120. For example, the transmitter 138 and receiver 140 may provide wireline communication and/or wireless communication to devices external to the components 120 and/or external to the device 100 within which the components 120 are integrated.

The transmitter 138 and receiver 140 may enable wireline communication using any suitable communications protocol, for example, protocols suitable for embedded applications. For example, the transmitter 138 and receiver 140 may be configured to enable universal serial bus (USB) communication, Ethernet local-area networking (LAN) communications, and the like.

The transmitter 138 and receiver 140 may enable wireless communications using any suitable communications protocol, for example, protocols suitable for embedded applications. For example, the transmitter 138 and receiver 140 may be configured to enable a wireless personal area network (PAN) communications protocol, a wireless LAN communications protocol, a wide area network (WAN) communications protocol and the like. The transmitter 138 and receiver 140 may be configured to communicate via Bluetooth, for example, with any supported or custom Bluetooth version and/or with any supported or custom protocol, including for example, A/V Control Transport Protocol (AVCTP), A/V Distribution Transport (AVDTP), Bluetooth Network Encapsulation Protocol (BNEP), IrDA Interoperability (IrDA), Multi-Channel Adaptation Protocol (MCAP), and RF Communications Protocol (RFCOMM), and the like. In examples, the transmitter 138 and receiver 140 may be configured to communicate via Bluetooth Low Energy (LE) and/or a Bluetooth Internet of Things (IoT) protocol. The transmitter 138 and receiver 140 may be configured to communicate via local mesh network protocols such as ZigBee, Z-Wave, Thread, and the like. for example. Such protocols may enable the transmitter 138 and receiver 140 to communicate with nearby devices such as the user's cell phone and/or a user's smartwatch. And communication with a local networked device, such as a mobile phone, may enable further communication with other devices across a wide area network (WAN) to devices remote, on the Internet, on a corporate network, and the like.

The transmitter 138 and receiver 140 may be configured to communicate via LAN protocols such as 802.11 wireless protocols like Wi-Fi, including but not limited to, communications in the 2.4 GHz, 5 GHz and 60 GHz frequency bands. Such protocols may enable the transmitter 138 and receiver 140 to communicate with local network access point, such as a wireless router in a user's home or office, for example. And communication with a local network access point may enable further communication with other devices present on the local network or across a WAN to devices remote, on the Internet, on a corporate network, and the like.

The transmitter 138 and receiver 140 may be configured to communicate via mobile wireless protocols such as global system for mobile communications (GSM), 4G long-term evolution protocol (LTE), 5G, and 5G new radio (NR), and any variety of mobile Internet of things (IoT) protocols. Such protocols may enable the transmitter 138 and receiver 140 to communicate more readily, for example when a user is mobile, traveling away from home or office, and without manual configuration.

The sensors 126 may include any device suitable for sensing an aspect of its environment such as biometric, physical, chemical, mechanical, electrical, encoded information, and the like. The controller 122 may interact with one or more sensors 126. The sensors 126 may be biometric sensors. The sensors 126 may include, for example a carbon monoxide (CO) sensor 142, a dose-detection sensor 144, an information sensor 146, a motion sensor 148, and the like.

As described herein, the term biomarker may be used interchangeably with the term biometric data. A biomarker may be a body temperature, such as a core body temperature and/or a skin temperature. A sensor, which may be included in sensors 126, may be a body temperature sensing system, which may measure body temperature data including temperature, emitted frequency spectra, and/or the like. The body temperature sensing system may measure body temperature data using some combination of thermometers and/or radio telemetry. For example, the body temperature sensing system may include a wearable antenna that measures body emission spectra. As another example, the body temperature sensing system may include a wearable patch that measures body temperature data, such as skin temperature data. The body temperature sensing system may be smartwatch 206, and/or may be associated with smartwatch 206.

The body temperature sensing system may calculate body temperature using the body temperature data. The body temperature sensing system may transmit the calculated body temperature to NRT device 100 and/or a device that may include the NRT and/or behavioral application. The body temperature data may be tracked over time and may be displayed to a user.

The body temperature sensing system may process the body temperature data locally or send the data to a processing unit and/or a computing system, such as computing resource 212. Based on the measured temperature data, the body temperature sensing system may detect body temperature-related biomarkers, characteristic fluctuations, climate, physical activity, nicotine cravings, and/or nicotine usage.

For example, the body temperature sensing system may detect that skin temperature has increased for a period before a user starts smoking, vaping, using tobacco, and/or consuming nicotine and may detect that skin temperature decreases once a user begins to smoke, vape, use tobacco, and/or consume nicotine. Nicotine consumption may comprise nicotine from a cigarette, tobacco product, electronic cigarette with nicotine, and/or an alternate source, such as a skin patch, chewing gum, nasal spray, inhaler, lozenge/tablet, oral spray, and the like. As another example, the body temperature sensing system may detect physical activities using measured fluctuations in body temperature.

A biomarker may be a maximal oxygen consumption (VO2). A sensor, which may be included in sensors 126, may be a VO2 max sensing system that may measure VO2 max data, including oxygen uptake, heart rate, and/or movement speed. The VO2 max sensing system may measure VO2 max data during physical activities, including running and/or walking.

The VO2 max sensing system may be included within a wearable device, such as smartwatch 206. The VO2 max sensing system may be smartwatch 206, and/or may be associated with smartwatch 206. The VO2 max sensing system may process the VO2 max data locally or may transmit the data to a processing unit (e.g., processor 132) and/or a computing system, such as computing resource 212.

Based on the measured VO2 max data, biomarkers may be derived, detected, and/or calculated including a VO2 max quantifier, VO2 max score, physical activity, and/or physical activity intensity. The VO2 max sensing system may select correct VO2 max data measurements during correct time segments to calculate accurate VO2 max information. Based on the VO2 max information, the sensing system may detect dominating cardio, vascular, and/or respiratory limiting factors. Based on the VO2 max information, cravings may be predicted.

A biomarker may be or may be associated with a physical activity. A sensor, which may be included in sensors 126, may be a physical activity sensing system that may measure physical activity data, including heart rate, motion, location, posture, range-of-motion, movement speed, and/or cadence. The physical activity sensing system may measure physical activity data including accelerometer, magnetometer, gyroscope, global positioning system (GPS), PPG, and/or ECG. The physical activity sensing system may include a wearable device, such as smartwatch 206. The physical activity wearable device may include, but is not limited to, a watch, wrist band, vest, glove, belt, headband, shoe, and/or garment. The physical sensing system may be smartwatch 206, and/or may be associated with smartwatch 206. The physical activity sensing system may locally process the physical activity data or transmit the data to a processing unit (e.g., processor 132) and/or a computing system, such as computing resource 212.

Based on the measured physical activity data, the physical activity sensing system may detect physical activity-related biomarkers, including but not limited to exercise activity, physical activity intensity, physical activity frequency, and/or physical activity duration. The physical activity sensing system may generate physical activity summaries based on physical activity information.

For example, the physical activity sensing system may send physical activity information to computing resource 212. The computing resource 212 may, based on the physical activity information, generate activity summaries, may associate activities to cravings, and/or may associate activities to nicotine usage. The computing system may store the physical activity information in user profiles. The computing system may display the physical activity information graphically. The computing system may select certain physical activity information and display the information together or separately.

A biomarker may be respiration rate. A sensor, which may be included in sensors 126, may be a respiration sensing system, which may measure respiration rate data, including inhalation, exhalation, chest cavity movement, and/or airflow. The respiration sensing system may measure respiration rate data mechanically acoustically, electrically, and/or optically (e.g., monitoring dilation of blood vessels using light). The respiration sensing system may measure respiration data mechanically by detecting chest cavity movement. Two or more applied electrodes on a chest may measure the changing distance between the electrodes to detect chest cavity expansion and contraction during a breath. The respiration sensing system may include a wearable skin patch. The respiration sensing system may measure respiration data acoustically using a microphone to record airflow sounds. The respiration sensing system may measure respiration data optically by monitoring dilation and contraction of blood vessels using light. The respiration sensing system may be smartwatch 206, and/or may be associated with smartwatch 206. The respiration sensing system may locally process the respiration data or transmit the data to a processing unit (e.g., processor 132) and/or a computing system, such as computing resource 212.

Based on measured respiration data, the respiration sensing system may generate respiration-related biomarkers including breath frequency, breath pattern, and/or breath depth. Based on the respiratory rate data, the respiration sensing system may generate a respiration quality score.

Based on the respiration rate data, the respiration sensing system may detect respiration-related biomarkers including irregular breathing, pain, nicotine cravings, and/or nicotine usage.

A biomarker may be a blood pressure measure. A sensor, which may be included in sensors 126, may be a blood pressure sensing system, which may measure blood pressure data including blood vessel diameter, tissue volume, and/or pulse transit time. The blood pressure sensing system may measure blood pressure data using oscillometric measurements, ultrasound patches, photoplethysmography, and/or arterial tonometry. The blood pressure sensing system using photoplethysmography may include a photodetector to sense light scattered by imposed light from an optical emitter. The blood pressure sensing system using arterial tonometry may use arterial wall application. The blood pressure sensing system may include an inflatable cuff, wristband, watch and/or ultrasound patch. The blood pressure sensing system may be smartwatch 206, and/or may be associated with smartwatch 206.

Based on the measured blood pressure data, a blood pressure sensing system may quantify blood pressure-related biomarkers including systolic blood pressure, diastolic blood pressure, and/or pulse transit time. The blood pressure sensing system may use the blood pressure-related biomarkers to detect nicotine cravings and/or nicotine usage. For example, a user that smokes 1 cigarette a day may be associated with a higher (0.21 bpm; 95% confidence interval 0.19; 0.24) resting heart rate, slightly higher diastolic blood pressure (0.05 mm Hg; 95% confidence interval 0.02; 0.08), systolic blood pressure (0.08 mm Hg; 95% confidence interval 0.03; 0.13). A blood pressure sensing system may process the blood pressure data locally or transmit the data to a processing unit (e.g., processor 132) and/or a computing system, such as computing resource 212.

A biomarker may be a heart rate variability (HRV). A sensor, which may be included in sensors 126, may be a HRV sensing system, which may measure HRV data including heartbeats and/or duration between consecutive heartbeats. The HRV data may include a standard deviation of a normal-to-normal (NN) sinus-initiated interbeat-intervals (SDNN), a room mean square of successive differences between normal heartbeats (RMSSD), a number of pairs of successive NN intervals that differ by more than 50 milliseconds (NN50), a proportion of NN50 divided by the total number of NN intervals (pNN50), a low frequency (LF) heart rate oscillation, a ultra-low-frequency (ULF) heart rate oscillation, a very-low-frequency (VLF) heart rate oscillation, a high-frequency (HF) heart rate oscillation, and the like.

The HRV sensing system may measure HRV data electrically or optically. The HRV sensing system may measure heart rate variability data electrically using ECG traces. The HRV sensing system may use ECG traces to measure the time period variation between R peaks in a QRS complex. An HRV sensing system may measure heart rate variability optically using PPG traces. The HRV sensing system may use PPG traces to measure the time period variation of inter-beat intervals. The HRV sensing system may measure HRV data over a set time interval. The HRV sensing system may include a wearable device, including a ring, watch, wristband, and/or patch. The HRV sensing system may be smartwatch 206.

Based on the HRV data, an HRV sensing system may detect HRV-related biomarkers, which may indicate cardiovascular health, changes in HRV, meal monitoring, anxiety levels, physical activity, nicotine cravings, and/or nicotine usage. For example, an HRV sensing system may detect high cardiovascular health based on high HRV. As another example, an HRV sensing system may detect an increase in a frequency domain index of HRV, which may indicate smoking cessation. As another example, an HRV sensing system may detect a biomarker that indicates a user has successfully stopped smoking and/or reduced nicotine usage, for example, by detecting a higher SDNN, a higher RMSSD, a higher pNN50, a higher LF, and/or a higher HF. The HRV sensing system may locally process HRV data or transmit the data to a processing unit (e.g., processor 132) and/or a computing system, such as computing resource 212.

A biomarker may be a heart rate. A sensor, which may be included in sensors 126, may be a heart rate sensing system, which may measure heart rate data including heart chamber expansion, heart chamber contraction, and/or reflected light. The heart rate sensing system may use ECG and/or PPG to measure heart rate data. For example, the heart rate sensing system using ECG may include a radio transmitter, receiver, and one or more electrodes. The radio transmitter and receiver may record voltages across electrodes positioned on the skin resulting from expansion and contraction of heart chambers. The heart rate sensing system may calculate heart rate using measured voltage. For example, the heart rate sensing system using PPG may impose green light on skin and record the reflected light in a photodetector. The heart rate sensing system may calculate heart rate using the measured light absorbed by the blood over a period of time. The heart rate sensing system may include a watch, a wearable elastic band, a skin patch, a bracelet, garments, a wrist strap, an earphone, and/or a headband. The heart rate sensing system may be smartwatch 206, and/or may be associated with smartwatch 206.

Based on the measured heart rate data, the heart rate sensing system may calculate heart rate-related biomarkers including heart rate, heart rate variability, and/or average heart rate. Based on the heart rate data, the heart rate sensing system may detect biomarkers, which may indicate stress, pain, nicotine cravings and/or nicotine usage. The heart rate sensing system may detect when a resting heart rate for a user exceeds a threshold. For example, the heart rating sensing system ay detect that a user may have a higher resting HR, which may indicate that the user may not have ceased smoking and/or reduced nicotine usage. As another example, the heart rate system may determine that a user may have continued smoking and/or using nicotine or may be a smoker and/or nicotine user by detecting that the user has a slower heart rate increase during exercise, a lower max heart rate, a lower heart rate reserve, and/or an attenuated heart rate decline during a recovery. The heart rate sensing system may process heart rate data locally or transmit the data to a processing unit (e.g., processor 132) and/or a computing system, such as computing resource 212.

A biomarker may be a galvanic skin response. A sensor, which may be included in sensors 126, may be a GSR sensing system, which may measure skin conductance data including electrical conductivity. The GSR sensing system may include one or more electrodes. The GSR sensing system may measure electrical conductivity by applying a voltage across the electrodes. The electrodes may include silver or silver chloride. The GSR sensing system may be placed on one or more fingers. For example, the GSR sensing system may include a wearable device, which may include one or more sensors that may attach to one or more fingers. GSR data may vary based on sweat levels. The GSR sensing system may be smartwatch 206, and/or may be associated with smartwatch 206. The GSR sensing system may process GSR data locally or transmit the data to a processing unit (e.g., processor 132) and/or a computing system, such as computing resource 212.

Based on the GSR data, a GSR sensing system may calculate GSR related biomarkers, which may indicate sympathetic activity levels, nicotine cravings, and/or nicotine usage. For example, a GSR sensing system may detect high sympathetic activity levels based on high skin conductance. As another example, the GSR sensing system may detect a smoking event by detecting an increase in a GSR measurement during a time before the smoking event, a decrease in a GSR during the smoking event, and/or an increase in GSR during a time after the smoking event.

The CO sensor 142 may include any sensing device suitable for determining a presence and/or concentration of CO in the vicinity of the sensor. The CO sensor may be a biomimetic-type CO sensor, an electrochemical-type CO sensor, a semiconductor-type CO sensor, or the like. The CO sensor 142 may communicate information about the presence and/or concentration of CO to the controller 122 via the input/output devices 136. In examples, a CO sensor 142 may determine the level of CO in the expired air of a smoker engaging in a smoking cessation and/or nicotine quit journey. The level detected by the CO sensor 142 may be indicative of the magnitude of the smoking behavior. For example, expired-air CO levels below around 9 ppm and/or at or below around 4 ppm may be indicative of general smoking abstinence.

The dose-detection sensor 144 may be any sensor suitable for detecting that a dose was dispensed. In examples, a mechanical arrangement may translate the force and/or movement that causes dispensing to the sensor 144. The sensor 144 may include a magnetic field sensor, such as a small-scale micro-electromechanical system (MEMS) magnetic field sensor, a contact closure, a reed switch, a potentiometer, a force sensor, a push button, or the like. In examples, the dispensing device may use an electrically controlled dispensing mechanism, like a controllable electric pump. The dose-detection sensor 144 may include a logical determination that the dose was dispensed. The dose-detection sensor 144 may communicate any information suitable for determining dispensing of a dose. For example, the dose-detection sensor 144 may signal a voltage level indicative of a dose, a logic toggle, a numeric dose count, or an analog signal that that may be processed (though a lowpass filter, for example) to determine that the signal indicates that a dose delivered to the controller via the input/output devices 136. A dose-detection sensor 144 may have a level of precision or resolution such that the controller 122 may determine the duration of the actuation. For example, an analog signal may be processed via an analog-to-digital converter, processed with a hysteresis threshold, and the resulting state duration may be determined.

The information sensor 146 may include any sensor suitable for reading stored information. In an embedded application with a physical platform, information may be encoded and stored on a variety a media that may be incorporated into aspects of physical design. For example, information about the authenticity, concentration, volume, etc. of the vial of nicotine formulation may be encoded and stored in a way that is physically associated with the vial itself. In examples, the information may be encoded on the vial in a quick read (QR) code, in a readable integrated circuit, such as a one-wire identification chip, in a near-field communications (NFC) tag, in physical/mechanical keying, in a Subscriber Identification Module (SIM), or the like. When a vial is inserted into the device 100, the information sensor 146 may read information encoded with the vial. The controller 122 may use that information to cross-reference and/or authenticate the vial. In an example, the function of the information sensor 146 may be performed via logic and programming to receive QR code information from a paired smartphone QR code reader. The user may pair, via Bluetooth, a smart phone with the device 100. The user may use the phone to scan the QR code, and the phone may communicate the information to the controller 122 via communications devices 124. In examples, the information sensor 146 may also be suitable for writing information back onto the medium associated with the vial, such as with a read/writable NFC tag, for example.

Once the information has been acquired by the information sensor 146 and communicated to the processor 132, the processor 132 may identify and authenticate the vial. The processor may perform any digital algorithm suitable for identification and/or authentication, such as traditional cryptographic algorithms, public/private key cryptography, security token processing, remote database look-up, blockchain processing, and/or the like.

The motion sensor 148 may include any sensor suitable for determining relative motion, acceleration, velocity, orientation, and/or the like of the device 100. The motion sensor 148 may include a piezoelectric, piezoresistive, and/or capacitive component to convert physical motion into an electrical signal. For example, the motion sensor 148 may include an accelerometer. The motion sensor 148 may include a microelectromechanical system (MEMS) device, such as a MEMS thermal accelerometer. The motion sensor 148 may be suitable for sensing a repetitive or periodic motion such as fidgeting by a user holding the device 100. The motion sensor 148 may communicate this information via the input output/devices 136 to the processor 132 for processing. The detection of a user fidgeting may be indicative of an onset craving for nicotine, for example.

The device 100 may include one or more drivers 128 to communicate feedback to a user and/or to drive a mechanical action. The drivers 128 may include a lockout mechanism 150, a light emitting diode (LED) driver 152, and the like. Other drivers 128 may include haptic feedback drivers, audio output drivers, heating element drivers, and/or the like.

The lockout mechanism 150 may include any electromechanical device suitable for providing, at the command of the controller 122, mechanical interference with the operation of the dispenser. For example, the lockout mechanism 150 may include a magnetic solenoid that is controlled by the processor 132 by way of an input/output device 136. The magnetic solenoid may cause the movement of a mechanical latch, that may be configured to enable/disable the dispenser actuation. Similarly, the lockout mechanism 150 may include piezoelectric "squiggle" motor that may be controlled by the processor 132 via the input/output devices 136 to pivot a mechanical latch in and out of the path of travel of a dispenser's actuation carriage. The lockout mechanism 150 may include a stepper motor, unipolar motor, bipolar motor, servo motor, and/or the like.

The LED driver 152 may include any circuitry suitable for illuminating an LED. The LED driver 152 may be controllable by the processor 132 via the input/output devices 136. The LED driver 152 may be used to indicate status information to a user. The LED driver 152 may include a multicolor LED driver.

The power management subsystem 130 may include circuitry suitable for managing and distributing power to the components 100. The power management subsystem 130 may include a battery, a battery charger, and a direct current (DC) power distribution system, for example. The power management subsystem 130 may communicate with the processor 132 via the input/output devices 136 to provide information such as battery charging status. The power management subsystem 130 may include a replaceable battery and/or a physical connector to enable external charging of the battery.

Figure 2A:
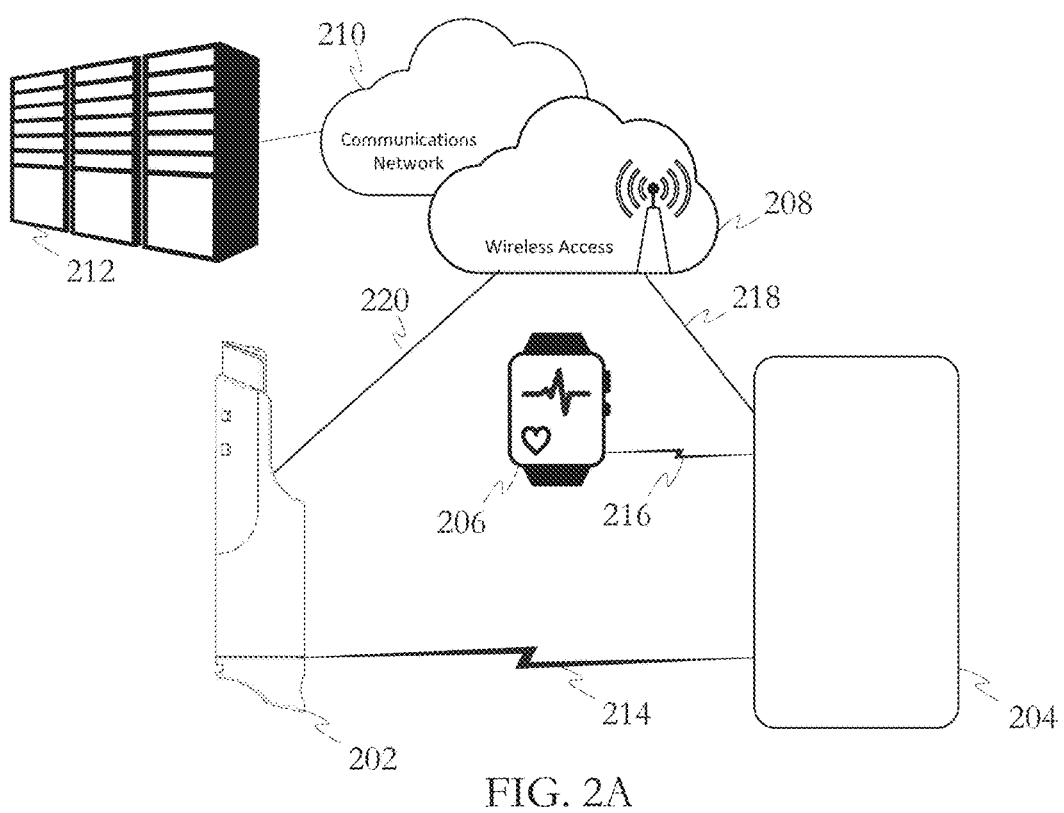
FIG. 2A is an architecture diagram for an example system to support a smart NRT device.

FIG. 2A is an architecture diagram for an example system 200 to support an NRT device 202. The NRT device 202 may be a nicotine dispenser with sensing, communications, driving, and processing functionality, such as the NRT device 100 described in FIGS. 1A-C, for example. The system 200 may include the NRT device 202, a smartphone 204 with a corresponding NRT app and/or behavioral support app, a smartwatch 206 with corresponding NRT app and/or behavioral support app, a wireless access network 208, a communications network 210, and a computing resource 212.

The smartphone 204 may include a NRT app and/or a behavioral support app. The smartphone 204 may provide a primary user interface for a personalized smoking cessation journey. The smartphone 204 may provide passive or active tracking and/or location services.

The smartwatch 206 may provide a dashboard user interface. The smartwatch 206 may also provide biometric feedback and data such as heart rate and/or heart rate variability, for example. The smartwatch 206 may perform activity tracking and provide activity information. In examples, the smartwatch 206 may include a galvanic skin response sensor.

The device 202 may include a nicotine replacement therapy dispenser, a CO sensor, an electronically controllable lock-out mechanism, a replaceable nicotine formulation vial, a vial identification and/or authentication functionality, NRT actuation/usage detection functionality, fidget detection functionality, geofencing functionality, and/or the like.

The computing resources 212 may provide data storage and processing functionality. The computing resources 212 may receive and analyze behavioral data. For example, the computing resources 212 may receive and analyze behavioral data to identify predictive endpoints for the journey such as heart rate, heart rate variability, and/or CO levels, for example.

The components of the system 200 may communicate with each other over various communications protocols. The device 202 may communicate with a smartphone 204 via a Bluetooth wireless link 214, for example. The smartwatch 206 may communicate with the smartphone 204 over a Bluetooth wireless link 216. The smart phone 204 may communicate with the wireless access network 208 over a wireless link 218 for example. The wireless link 218 may include any suitable wireless protocol, such as 802.11 wireless protocols like Wi-Fi, GSM, 4G LTE, 5G, and 5G NR, and any variety of mobile IoT protocols.

The communications network 210 may include a long-distance data network, such as a private corporate network, a virtual private network (VPN), a public commercial network, an interconnection of networks, such as the Internet, or the like. The communications network 210 may provide connectivity to the computing resource 212.

The computing resource 212 may include any server resources suitable for remote processing and/or storing of information. For example, the computing resource 212 may include a server, a cloud server, data center, a virtual machine server, and the like. In examples, the device 202 may communicate with the computing resource 212 via the smartphone 204. And in examples, the device 202 may communicate with the computing resource 212 via its own wireless link 220.

The system 200 may enable the collection and processing of information related to a smoking cessation journey. The system 200 may enable the generation of behavioral support data for the smoking cessation journey. For example, a CO measurement sensor integrated in the device 202 may enable convenient CO measurements taken during NRT usage. The measurements may be sent and processed by the NRT app and/or the behavioral support app on the smartphone 204 and/or by the computing resource 212. Analysis of this data may enable identification of a user's smoking relapse. In examples, activity data from the smartwatch 206, from the motion sensor in the device 202, and/or activity tracking by the smartphone 204 can be used to set dynamic thresholds for CO levels. Generally, CO is eliminated in expired air, and the rate of elimination depends on the individual's pulmonary ventilation rate. Accordingly, the half-life for CO may be a function of the amount of recent physical activity. The activity data may be used to more accurately interpret the CO levels for specific measurements.

Similarly, the NRT app and/or behavioral support app on the smartphone 204 and/or the computer resources 212 may analyze data from an actuation sensor on the device 202 indicative of NTR usage. This information may be used to assess adherence to the smoking cessation program and may be used to drive a feedback loop to the user—providing notifications and encouragement. The Bluetooth link 214 between the device 202 and the smartphone 204 may enable CO level and NRT usage data to be used for immediate user feedback of smoking cessation program.

In examples, other relevant data such as location, timestamps, dose number, or the duration of actuation, may be captured and processed together with CO level and NRT usage to identify patterns of successful and unsuccessful smoking cessation journeys and provide timely and relevant feedback to the user. The data may be used to train a machine learning algorithm that may determine the appropriate selection and timing. For example, location data may be used in connection with CO levels and NRT usage to identify certain triggers and/or habits associated with smoking and/or cravings. These identified location triggers may be used to drive timely feedback and encouragement to the user.

The collected data may be used to provide limitations on nicotine use to further enhance smoking cessation program effectiveness and/or for safety. For example, location data may be used to actuate a lockout mechanism to prevent nicotine formulation dispensing. For example, data collected regarding the identification and authentication of the nicotine formulation vial may be used to ensure that authentic and/or properly concentrated nicotine formulation vials are operable, and that unauthentic and/or improperly concentrated nicotine formulation vials are inoperable for the user.

Figure 2B:
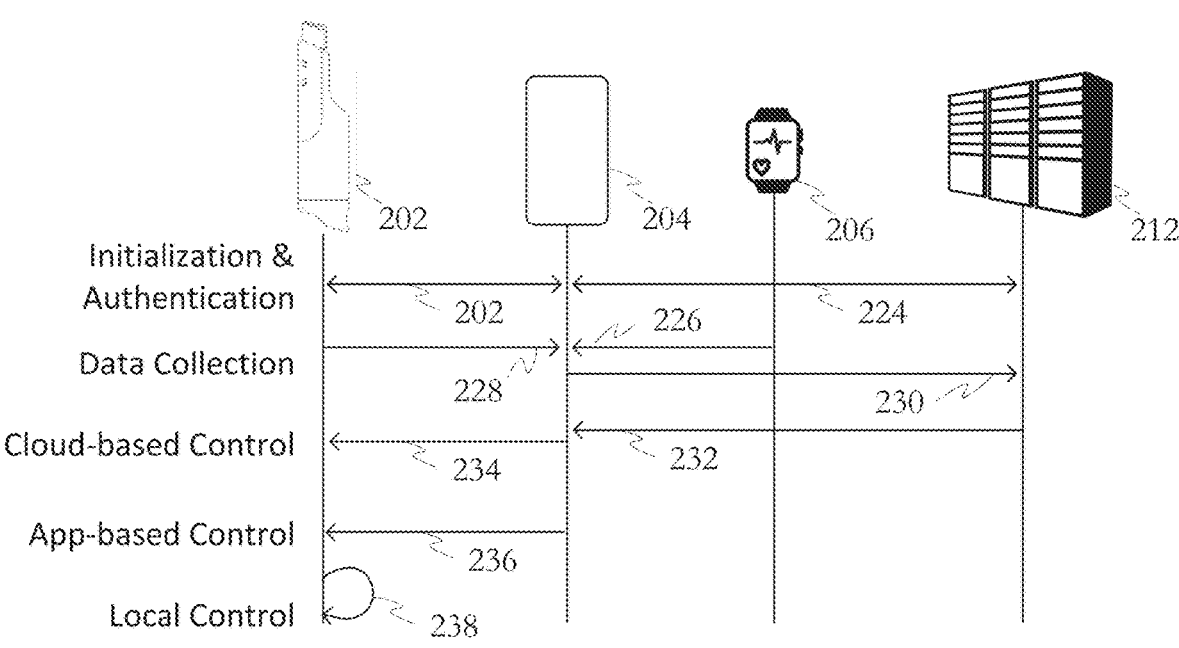
FIG. 2B is a messaging flow diagram for the example system.

FIG. 2B is an example messaging flow diagram for the example system 200. For example, the system 200 may include communication and processing for functions such as initialization and authentication of the dispensing device and the NRT app and/or the behavioral support app; data collection from a smartwatch and/or one or more sensors associated with the dispensing device 202; cloud base control, triggering, notification messaging and the like, app-based control, messaging and notifications, and the like; and/or local control of the dispensing device 202.

Initialization and authentication messages 222 may be exchanged between device 202 and the smart phone 204.

Initialization and authentication messaging 224 may be exchanged between the computing resource 212 and the smart phone 204. For example, a new user may create a user account via the smart phone 204. The account information may be processed by the computing resource 212. The new user may initialize dispensing device 202 and/or a wish to authenticate a nicotine formulation vial. That information may be communicated via messaging 222 to the smartphone 204 and then via messaging 224 to computing resources 212. Responsive information about user accounts, vial authentication, etc. may be messaged back to the device 202.

Data collection functionality may include messaging 226 from the smartwatch 206 and/or to the smartphone 204. This messaging may include information such as activity information, heart rate, heart rate variability, and other biometric information. The data collection functionality may include messaging 228 from the device 202 to the smartphone 204. This messaging 228 may include information about device operation, such as actuation time/date/location, actuation duration, motion, CO level, and the like. In examples, the smartphone 204 may aggregate the messaging 226, 228, process it locally, and/or communicate it or related information to the computing resources 212 via messaging 230.

The system 200 enables cloud-based control functions, app-based control functions, and local control functions. For example, cessation journey information, such as predicative advice/encouragement to the user, adaptive journey updates, mechanical lockouts, and other feedback may be provided from the computing resources 212 to the smartphone 204 via messaging 232, and if appropriate, from the smartphone 204 to the device 202 via messaging 234. The computing resource 212 may communicate directly to the device 202 by a direct wireless link 230 via its own messaging (not shown).

In examples, smoking cessation journey information may be generated from the NRT application and/or behavior support application, displayed directly (and/or displayed via the smartwatch 206). The smoking cessation journey information may be communicated to the device 202 via messaging 236.

In examples, the device 202 may provide local control via its local processor. Internal system calls and/or local messaging is illustrated as a local loop 238.

Figure 3A:
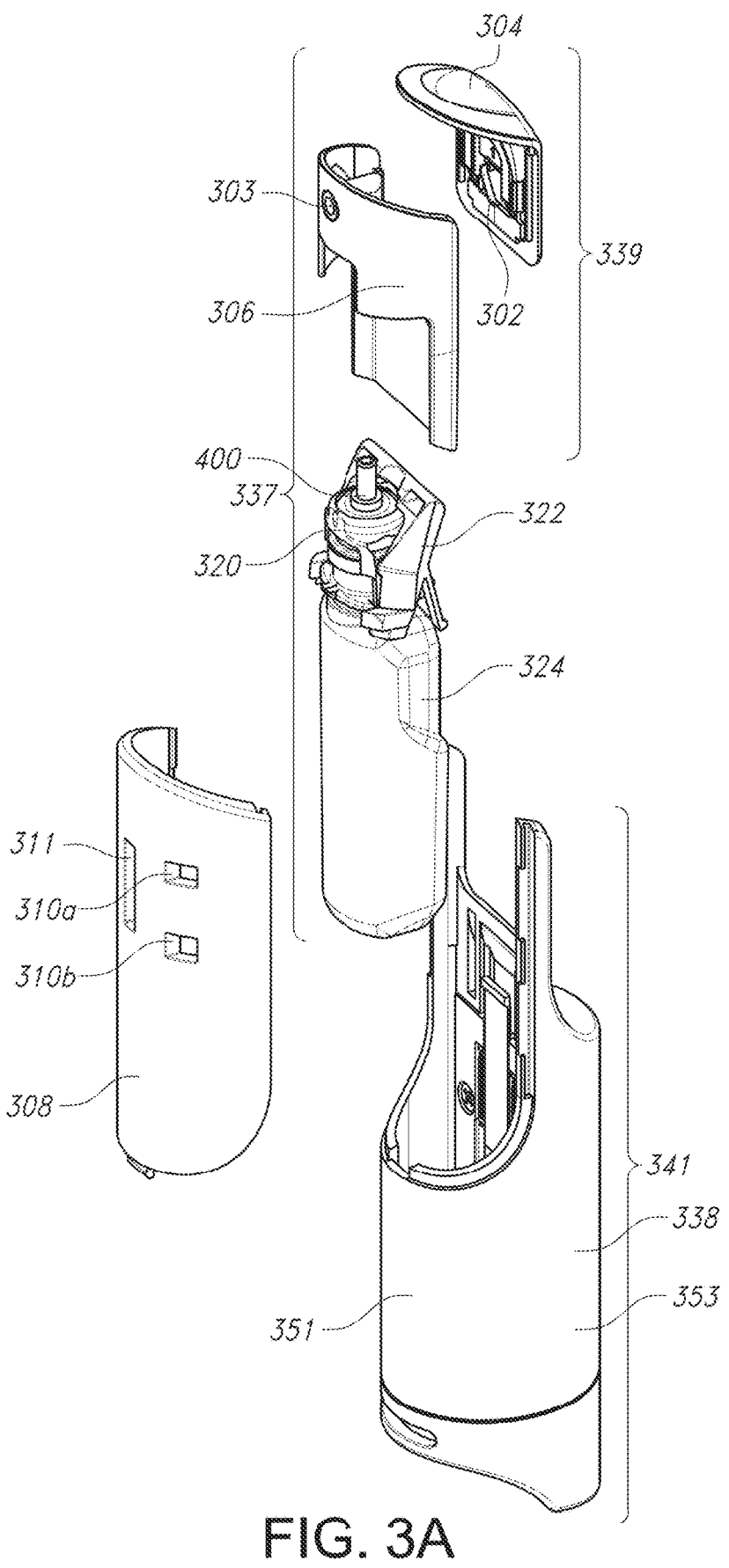
FIGS. 3A-B depicts example schematic views of the smart NRT device.

FIG. 3A depicts an example schematic view of a device, which may be the smart NRT device 100. The device 100 may include a housing 341, a dispenser 337 slidably receivable within the housing 341, and a cover 308 that is attachable to housing 341.

The housing 341 may be an elongate, hollow body, open at one end, and having an oblong cross-section. The housing 341 may have a curved front wall 351 and a curved back wall 353. The curved front wall 351 may have a cut out such that it the cover 308 is attachable to the housing 341. The housing 341 may have a mouthpiece 342 (see FIG. 3B) at one end.

An elongate, generally vertical, central slot 311 may be provided in the cover 308. A pair of smaller, square apertures 310a and 310c (see FIG. 5A) may be positioned at the upper end of the central slot 311, the apertures 310a and 310c being positioned either side of the central slot 311, diametrically opposite one another. A second pair of corresponding square apertures 310b and 310d may be positioned at the lower end of the central slot 311 in like manner, such that the four apertures 310a, 310b, 310c, and 310d may be positioned at the four corners of a notional square (see FIG. 5A).

Figure 3B:
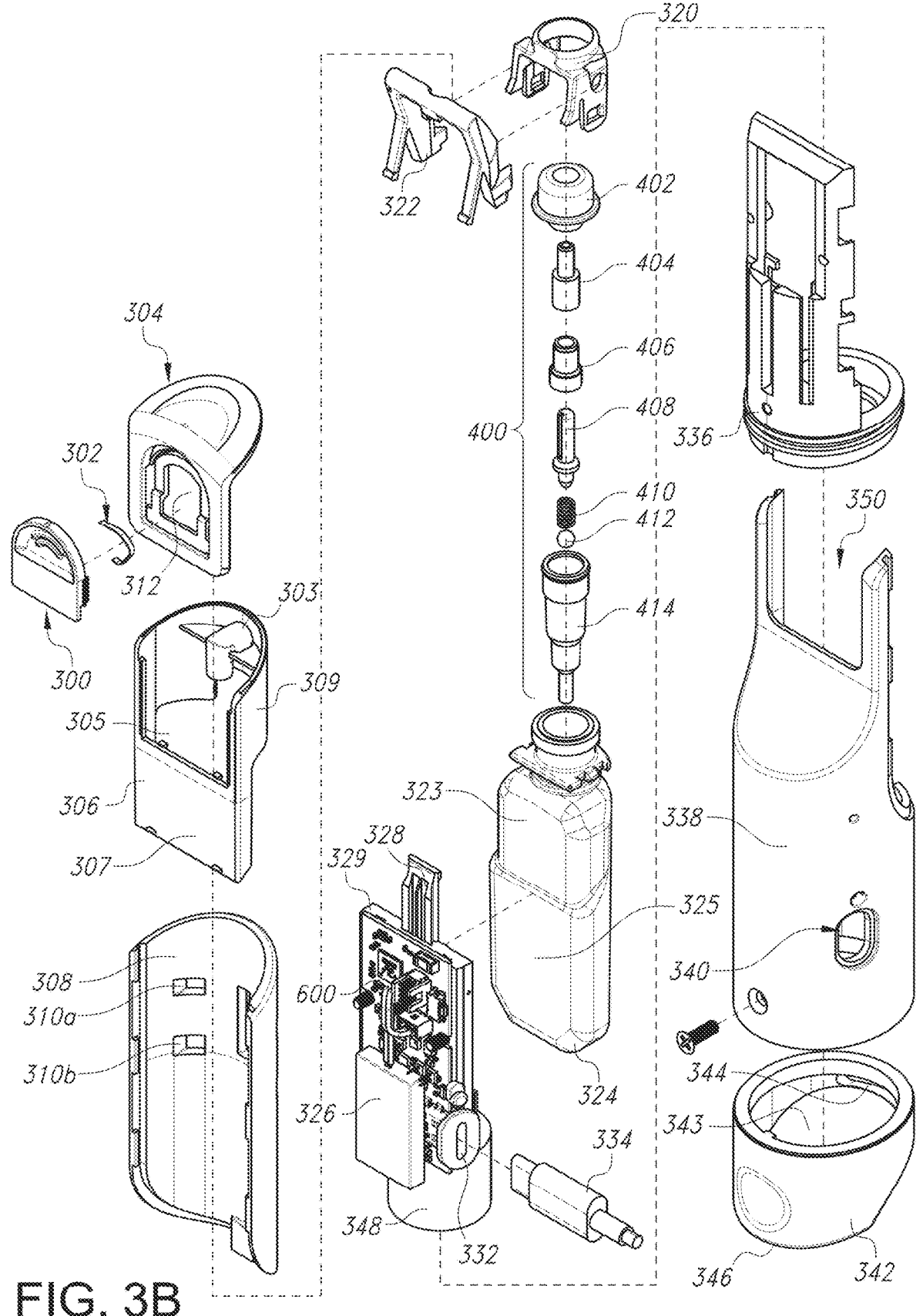

FIG. 3B depicts another example schematic view of the device. The dispenser head 339 may comprise a cap portion 304, a face portion 306, a sprung member 302, and a transmission plate 300.

The face portion 306 may have a D-shaped cross-section. The face portion 306 may allow for a telescopic, sliding engagement within the housing 341. The face portion 306 may have a curved front wall 309 and a flat rear wall 307. The curved front wall 309 and the flat rear wall 307 of face portion 306 may be complementary to one or more walls of housing 341.

An upper section of the flat rear wall 307 of face portion 306 may be cut away to form an irregular shaped opening 305. A lower section of the flat rear wall 307 may be made of a clear material and may correspond to the irregular shaped opening 305 in the main housing portion 338 of the housing 341. The lower section of the flat rear wall 307 and irregular shaped opening 305 may allow for a portion of the vial 324 to be seen when the vial 324 is contained within housing 341. This may be done, for example, to allow the QR code 323 to be seen via irregular shaped opening 350. This may allow another device to scan the QR code, such as for authentication purposes, while vial 324 is contained within housing 341.

The lower section of the curved front wall 309 may be cut away. A pair of slide projections may be provided along the bottom edge of the outer face of a rear wall of face portion 306. The pair of slide projections may be slidably engageable with the guide slots on a rear wall of main housing portion 338 of the housing 341. In addition, a pair of ramp projections may be provided along the top edge of the inner face of the rear wall of the main housing portion 338. This pair of ramp projections may be provided for a locking engagement with the ramp elements that may be provided on the collar 320.

An outlet 303 may be provided in the curved front wall 309. The outlet 303, which may be any spray outlet, is in fluid communication with a supply passage that may be formed as an integral part of the face portion 306 and may extending back into the opening 303.

The cap portion 304 may comprise a flat rear wall that may fit the cut-away section of the flat rear wall 307 of the face portion 306. The cap portion 304 may have a cantilevered top portion that may projecting from the upper edge of the rear wall and may have a D-shaped cross-section corresponding to the cross section of the face portion 306.

The cap portion 304 may be fitted within an opening of the face portion 306 such that the rear wall of cap portion 304 and the flat rear wall 307 form a peripheral skirt. The rear wall of cap portion 304 may form a stop in the form of a ridge.

The rear wall of the cap portion 304 may comprise an arched window 312. The upper edge of the arched window 312 may be provided by a crescent-shaped shoulder, recessed from the rear wall of the cap portion 304. A straight lower edge of the arched window 312 may be provided with a hinged arched frame on the inside of the rear wall of cap portion 304 and may be attached along the lower edge of the via a hinge.

A sprung member 302 may be attached to a portion of the arched window 312 and the transmission plate 300. For example, sprung member may be used to hold the transmission plate 300 within the arched window 312.

The transmission plate 300 may have a similar outline shape to the arched window 312. The inner face of the transmission plate 300 may comprise guide channels that may be used to slidably engaging a frame section of the cap portion 304.

The transmission plate 300 may be slidably mounted to a hinged frame of the cap portion 304. For example, guide channels of transmission plate 300 may contact a frame section of the cap portion 304. The transmission plate 300 may be attached to the upper arm of the sprung member 302 and the sprung member 302 may act to resiliently bias the transmission plate 300 into the position.

The cover 308 may be attachable to the main housing portion 338 of the housing 341. The cover 308 has one or more guide projections that may be slidably engaged with the main housing portion 338 such that the cover 308 may be snap fitted into place. The cover 308 may cover the dispenser 337 and the dispenser head 339 when the dispenser head 339 is in a non-operative position. The cover 308 may not cover the dispenser head 339 when the dispenser head 339 is in an operative position. The cover 308 may allow the dispenser head 339 to slide telescopically along an axis relative to the main housing portion 338. For example, the cover 308 may be configured to allow the dispenser head 339 slide telescopically out of the main housing portion 338 such that the dispenser head 339 may be in an operative position for dispensing.

The dispenser 337 comprises a number of sub-components: a dispenser body in the form of a vial 324, a dispensing mechanism, a collar 320, a locking lever 322, and an actuating member. The dispensing mechanism may be in the form of a pump mechanism 400. The collar 320 may be for securing the pump mechanism 400 to the vial 324. The actuating member may be the dispenser head 339.

The vial 324 may comprising a main body portion that may have a D-shaped cross-section. The main body portion may have a dispensing chamber for holding a substance. For example, the vial 324 may hold a nicotine formulation. The vial 324 may have a hollow, cylindrical neck portion that may be an open mouth. The open mouth may allow a pumping mechanism 400 to dispense a nicotine formulation held within the vial 324.

The vial 324 may include a QR code 323. The QR code 323 may be used for authentication purposes. For example, QR code 323 may be used to authenticate the vial such that device 100 may be allowed to use vial 324. As further described herein, device 100 may use a lockout mechanism to prevent the vial 324 from being used when the device 100 is unable to authenticate the vial 324, for example, using QR code 323.

The QR code 323 may be used for information purposes. For example, the QR code 323 may provide information as to the strength of the nicotine formulation, the volume of nicotine formulation contained within the vial 324, an amount of nicotine in a dose of the nicotine formulation, an expiration date of the nicotine formulation, and/or the like.

The vial 324 may include a chip 325. The vial 324 may include a slight indentation to accommodate the thickness of the chip 325. The chip 325 may be a near field communication (NFC) device, a wire trace, an electronic chip, and/or the like. The chip 325 may comprise a thing or flexible PCB substrate. The device 100 may provide a mechanism that may contact or detect the chip 325 such that the device 100 may read and/or write information to the chip 325.

The chip 325 may be used for authentication purposes. For example, the chip 325 may be used to authenticate the vial such that the device 100 may be allowed to use the vial 324. As further described herein, the device 100 may use a lockout mechanism to prevent the vial 324 from being used when the device 100 is unable to authenticate the vial 324, for example, using the chip 325.

The chip 325 may be used for information purposes. For example, the chip 325 may provide information as to the strength of the nicotine formulation, the volume of nicotine formulation contained within the vial 324, an amount of nicotine in a dose of the nicotine formulation, an expiration date of the nicotine formulation, and/or the like.

The vial 324 may be formed from any suitable material using any suitable method, for example by blow-molding a plastics material or the like. The vial 324 may hold a nicotine formulation and may be formed from a nicotine-inert material that may not absorb or react with the nicotine formulation. The vial 324 may be made from a material that may provide a barrier against migration of oxygen and water. The vial 324 may be made of glass, a copolymer of acrylonitrile and methyl acrylate, a cyclic olefin copolymer (COC), and combination thereof, and/or the like. Other suitable materials of which the vial 324 may be formed include materials selected from polymers based on dimethyl-2,6 naphthalene dicarboxylate or 2,6-naphthalene dicarboxylic acid monomers, such as polyethylene naphthalate (PEN) and polytrimethylene naphthalate (PTN), liquid crystal polymers (LCP), preferably LCPs comprising hydroxy benzoic acid and hydroxy naphthalenic acid, and combinations thereof. Suitable materials also include materials mixed with one or more of other polymer(s), selected from one or more of polyacrylonitrile (PAN), polyamide (PA), polyvinylidene chloride (PVDC), fluoropolymers, ethylene vinyl alcohol copolymer (EVOH), polyvinyl alcohol (PVA), ionomers, polyethylene (PE), polypropylene (PP) and polyethylene terephtalate (PET).

The vial 324 may include a neck portion that may incorporate a peripheral flange. The peripheral flange may be a rectangular shape but may include a curved front edge that may correspond a wall of housing 341. A front edge of the vial may include a guide projection and/or a pair of mounting projections respectively located on the opposite, shorter sides of the generally rectangular peripheral flange.

The dispensing mechanism may be in the form of a pump mechanism 400. The pump mechanism 400 may be a manually control mechanism or an electronically controlled mechanism. For example, the pump mechanism 400 may be a controllable electric pump.

Figure 3C:
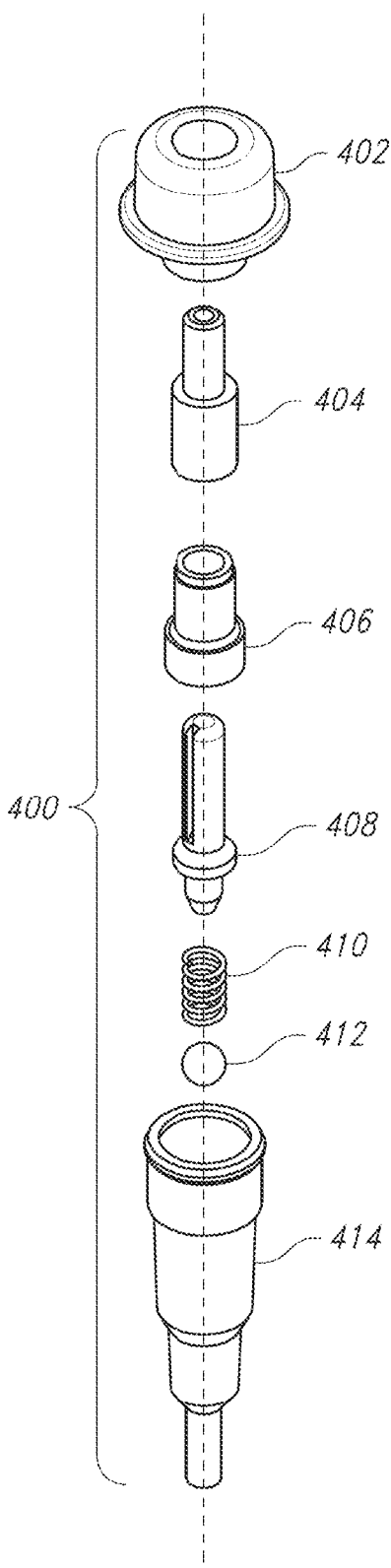
FIG. 3C depicts an example pumping mechanism that may be used by the smart NRT device.

FIG. 3C depicts an example pumping mechanism that may be used by the smart NRT device. The pump mechanism 400 may comprise an intake tube for drawing liquid from within the main body of the vial 324; a cylindrical pump housing that may provide an internal pump chamber, communicating with the intake tube; and a piston member 408 mounted for movement within the pump chamber, against a biasing member 410 in the form of coil spring, for displacing the contents of the pump chamber up through a bore in the piston member 408 and out through a hollow stem 404 connected to piston member 408.

The pump mechanism 400 may comprise a pump housing formed by connecting a pump chamber 414 to a ring cap 402. The pump mechanism 400 may provide an internal pump chamber within the pump chamber 414. The pump chamber 414 may communicate with the intake tube. Check valve 412 may be placed within the pump chamber 414. The check valve 412 allows contents from vial 324 to be received into the pump chamber 414 through the intake tube. The check valve 412 may prevent contents within the pump chamber 414 from moving through the intake tube and into vial 324.

A piston member 408 may be mounted for movement within the pump chamber 414. The piston member 408 may be placed against a biasing member 410 in contact with the check valve 412, such that the piston member may displace the contents of the pump chamber 414 through a bore in the piston member 408 and out through a hollow stem 404. The hollow stem 404 may be connected to the piston member 408. The piston member 408 may be held in position within the pump chamber 414 by a piston collar 406. The piston collar 406 may fit within the ring cap 402. The ring cap 402 may have a bore that may allow an upper portion of the hollow stem 404 to pass through while allowing the ring cap 402 to connect with a lower portion of the hollow stem 404.

Referring again to FIG. 3B, the pump housing may be seated on the rim of the mouth of the vial 324, such that the pump housing may seal the mouth of the vial 324, with the intake tube extending down into the dispensing chamber of the vial 324.

The collar 320 may clamp the pump mechanism 400 to vial 324. For example, the collar 320 may clamp the pump mechanism 400 to a mouth of vial 324 and may assist in sealing the vial 324 during use. The collar 320 may comprise a ring portion and a pair of diametrically opposed arms from the ring portion. An arm (e.g., each arm) may have an aperture at its lower end. The collar 320 may have a pair of secondary legs that may terminate in respective ramp elements for locking the dispenser head 339 to the collar 320.

To clamp the pump mechanism 400 to the vial 324, the pump housing may be seated on the rim of the mouth of the vial 324, and the collar 320 may be pressed down over the top of the pump housing with the arms of the collar 320 extending down either side of the pump housing. The arms of the collar 320 may be resiliently deformed by the sides of the pump housing and may engage with one or more mounting projections of the vial 324 in a snap fit. The pump housing may be clamped between the rim of the mouth of the vial 324 and the ring portion of the collar 320.

The locking lever 322 may comprise a pair of legs extending from the ends of a connecting yoke portion that extends perpendicularly to the pair of legs. A leg (e.g., each leg) may comprise a latching element in the form of a projecting foot positioned at the distal end of the leg, an inwardly projecting lug, positioned at a bend of the respective leg. The leg may comprise an element, which may be resilient, extending rearwardly from the back of the bend the leg and terminating opposite the heel of the projecting foot. The latching element, which may be resilient, may connect with square apertures 310a-d to allow device 100 to be locked into an operative position (e.g., unlocked position) or a non-operative position (e.g., locked position). The locking may occur using a snap fit. For example, the latching elements of the locking lever 322 may connect with the square aperture 310a and the square aperture 310c to allow the device 100 to be locked into an operative position where the dispenser head 339 is in a position that extends beyond the main housing portion 338. As another example, the latching elements of locking lever 322 may connect with square aperture 310b and square aperture 310d to allow device 100 to be locked into a non-operative position where the dispenser head 339 may be flush with or below an edge of the main housing portion 338.

A leg of the locking lever 322 may have resilience to allow a snap fit. For example, a rotating engagement of the lugs of the locking lever 322 with the circular apertures on the arms of the collar 320 may allow the locking lever 322 to be secured to the collar 320. The locking lever 322 may be secured to the collar 320 such that such that the locking lever 322 may rotate with respect to the collar 320 about an axis passing through the lugs of the locking lever 322.

The dispenser head 339 may be mounted for movement relative to the vial 324 to actuate the pump mechanism 400. For example, the dispenser head 339 may be resiliently mounted on the pump mechanism 400 for actuating movement relative to the vial 324, against the action of the coil spring, to actuate the pump mechanism 400 and dispense the contents of the vial 224 through the outlet 303. The actuation of dispenser head 339 may cause the locking lever 322 and/or the vial 324 to contact the carriage 328 such that the carriage 328 may move. For example, the carriage 328 may move in a direction relative to the movement of the actuation, the movement of vial 324, and/or the movement of the locking lever 322. The actuation of the dispenser head 339 may cause the carriage 328 to move, which may be detected by electronics 600. For example, electronics 600 may detect the carriage 328, which may be magnetic or may comprise magnets, or may have moved to such a degree that it may indicate that a dose of nicotine has been dispensed from the vial 324.

To mount the dispenser head 339, the dispenser head 339 may be pressed down onto the pump mechanism 400 such that the down pipe of a supply passage of the dispenser head 339 may engage a hollow stem of a piston member to form a closed passageway between the vial 324 and the outlet 303, via an internal pump chamber in the pump mechanism, for example. As the dispenser head 339 is pressed down onto the pump mechanism, engagement of the ramp projections and ramp elements may serve to snap-fit the rear wall 307 down over the collar 320, whereby the ramp projections and ramp elements may subsequently limit upward movement of the dispenser head 339 relative to the collar 320 and the vial 324.

The housing 341 may include a mouthpiece 342, a main housing portion 338, a body frame 336, a carbon monoxide sensor 348, a port 332, a battery pack 326, electronics 600, a carriage frame 329, and a carriage 328.

The body frame 336 may be attached to the main housing portion 338, for example, using a screw. The body frame 336 may have a hollow cylindrical neck portion that may provide an open mouth at one end. The carbon monoxide sensor 348 may be seated within the mouth of the body frame 336 and may extend past an edge of the mouth of the body frame 336. The mouthpiece 342 may be seated on the rim of the mouth of body frame 336 such that the mouthpiece 342 may seal the mouth of the body frame 336 with the carbon monoxide sensor 348, extending down into the upper opening 343 of the mouthpiece 342.

The main housing portion 338 is an elongate, hollow body, open at one end, and having an oblong cross-section. The main housing portion 338 may have a curved front wall and a curved back wall. The front wall may have a cut out such that the cover 308 is attachable to main housing portion 338. The main housing portion 338 may have an opening at one end, which may be in contact with mouthpiece 342. An upper section of a rear wall of main housing portion 338 may be cut away to form an irregular shaped opening 350. The irregular shaped opening 350 may correspond with a lower section of the flat rear wall 307 which may be made of a clear material. Irregular shaped opening 350 may allow for a portion of the vial 324 to be seen when the vial 324 is contained within the main housing portion 338. This may be done, for example, to allow the QR code 323 to be seen via irregular shaped opening 350. And this may allow another device to scan the QR code, such as for authentication purposes, while the vial 324 is contained within the main housing portion 338.

The mouthpiece 342 may be attached to the body frame 336 and may be in contact with the main housing portion 338. The mouthpiece 342 may include the upper opening 343 at a top portion of the mouthpiece 342 that may attach to the body frame 336. An edge of the upper opening 343 may be in contact with an edge of the main housing portion 338. The upper opening 343 may correspond to a dimension of the carbon monoxide sensor 348 such that the carbon monoxide sensor 348 may protrude into the mouthpiece 342 via the upper opening 343.

The mouthpiece 342 may include a circular aperture 346 (see FIG. 4A). The circular aperture 346 may be positioned to allow a flow of air from a user to enter the mouthpiece 342 via the circular aperture 346. The mouthpiece 342 may include an indentation on a face of the mouthpiece 342 that may encourage a user to properly use the mouthpiece 342. For example, the indentation may signal to the user that the user may place the mouthpiece 342 in their mouth such that their upper lip would be in contact with the indentation. The mouthpiece 342 may include an oblong aperture 344. The oblong aperture 344 may be positioned to allow a flow of air from a user to exit the mouthpiece 342 via the oblong aperture 344.

The carriage frame 329 may be attached to the body frame 336. For example, the carriage frame 329 may be mounted to the body frame 336 using one or more screws. The carriage frame 329 may include a pair of legs depending from the ends of a connecting yoke portion that may extend perpendicularly to each of the legs. The yoke portion of the carriage frame may have a recessed or cut away portion in the center. The cut away portion of the yoke may allow the carriage 328 to lay within the cut away portion such that the carriage 328 may lay flush with the carriage frame 329 while being able to move relative to the carriage frame 329.

The electronic package 600 may be attached to the carriage frame 329 using a screw, and the carriage frame 329 may be snapped fit into the body frame 336. The electronic package 600 may be attached to the port 332. The port 332 may be a universal serial bus (USB) port. The port 332 may be capable of receiving power. The port 332 may be capable of sending and/or receiving data. The port 332 may accept a corresponding plug such as the plug 334.

The electronics 600 may be connected and/or attached to battery pack 326. The battery pack 326 may include a battery, such as a lithium ion battery. the electronics 600 may include the communications interfaces 124, the sensors 126, the electrical and electromechanical drivers 128, and the power management subsystem 130. For example, the electronics 600 may include a sensor that may be used to read data from the QR code 323 and/or the chip 325. The electronics 600 may use the data to authenticate the vial 324.

The electronics 600 may comprise a PCB with a number of chips mounted thereon. The PCB may include castellated edges, such as a castellated edge 602 (see FIGS. 6A-B), to facilitate its mounting on the back face of carriage frame 329. The electronics 600 may be attached to a battery pack 326. The battery pack 600 may be affixed to a face of the PCB of electronics 600 that may face away from the carriage frame 329. The electronics 600 may be interposed between the battery pack 326.

To assemble the dispensing device 100, the various subcomponents of the dispenser 337 may be assembled as described herein. The dispenser 337 may be slidably engaged with the housing 341 by sliding the housing 341 over the vial 324 and snap-fitting the dispenser 337 into place. The cover 308 may be attached to the housing 341 by snap-fitting into place.

Figures 4C, 4D:
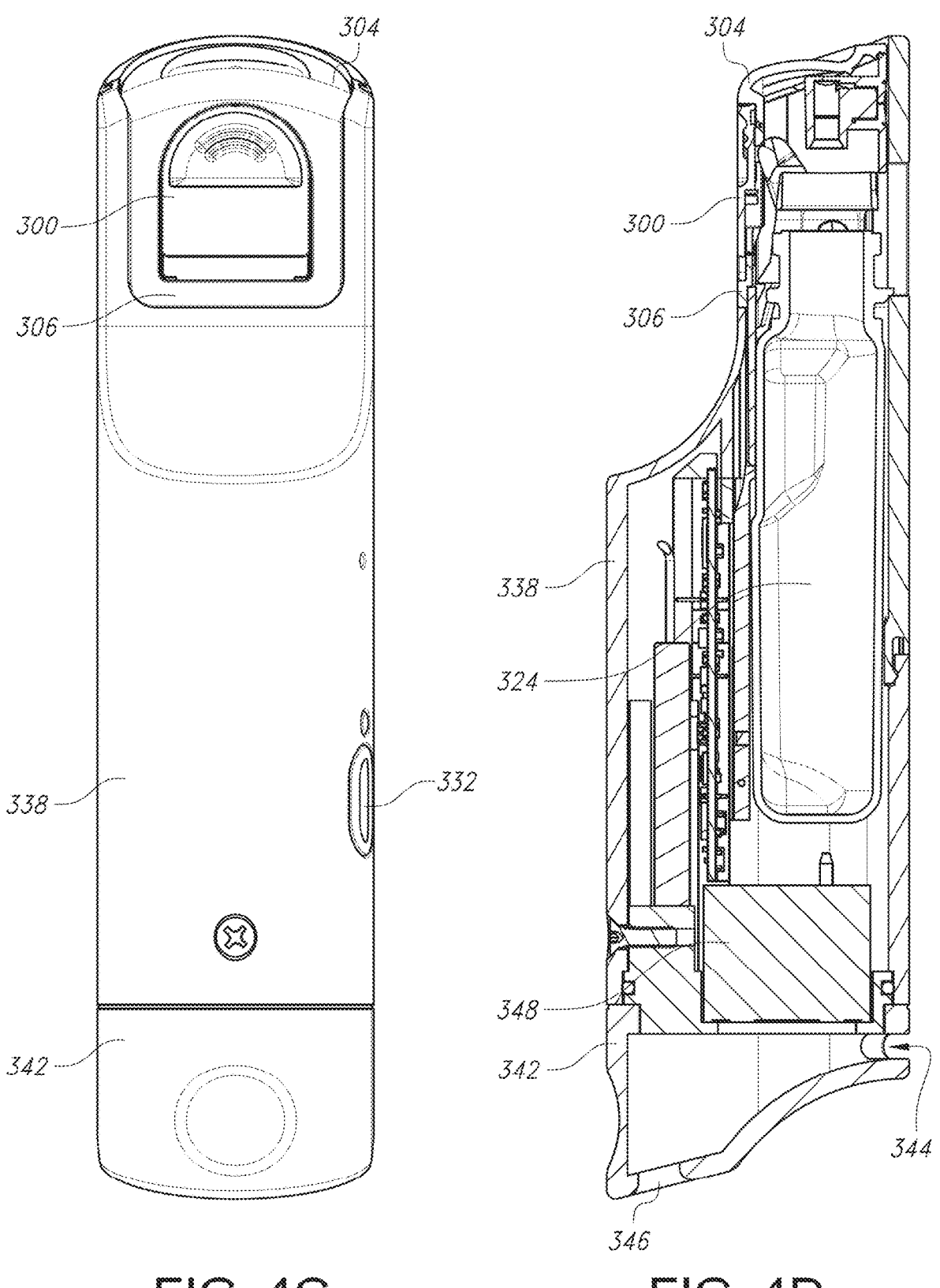

FIG. 4A-D depict perspective views of the smart NRT device with a dispenser head in a non-operative (e.g., locked position). FIG. 4A shows a front view of the smart NRT device, such as device 100. As shown in FIG. 4A, the dispensing device 100 may include the cover 308, the main housing portion 338, and the mouthpiece 342. The mouthpiece 342 may comprise the oblong aperture 344 and circular aperture the 346. The cover 308 may comprise square apertures 310a, 310b, 310c, and 310d. The cover 308 may comprise the central slot 311.

The device 100 can be put into a non-use configuration to prevent accidental dispensing of the nicotine formulation contained within device 100. As shown in FIG. 4A, the dispenser head may be retracted within the housing such that the dispenser head may be behind the cover 308 and an edge of the dispenser head may be flush with or below an edge of cover 308. For example, as shown in FIG. 4B, when in the non-operative or locked position, the cap portion 304 of the dispenser head may be flush with or below an edge of the cover 308. As shown in FIG. 4C, the face portion 306 of the dispenser head has been lowered into the main housing portion 338 such that the lower section of the flat rear wall 307 and/or the QR code 323 may not be seen.

FIG. 4D is a cut-away perspective view of device 100 in a non-use or non-operative position. As shown in FIG. 4D, the dispenser 100 can be put into a non-use configuration to prevent accidental dispensing of the nicotine formulation. The dispenser 337 may be lowered within main housing portion 338 to ensure that the dispenser 337 is prevented from mechanical shock which might otherwise damage the vial 324, with consequent leakage of the substance. The dispenser 337 may be lowered to provide a child resistant. For example, lowering the dispenser 337 within main housing portion 338 may prevent operation of the dispensing 100 by a child.

As shown in FIG. 4D, the dispenser 337 may be lowered within main housing portion 338 while allowing for room for the carbon monoxide sensor 348. For example, the dispenser 337 may be lowered within the main housing portion 338 in a way that the dispenser 337 may not damage or come in contact with the carbon monoxide sensor 348 while preventing mechanical shocks that may otherwise damage the vial 324.

Figures 5A, 5B:
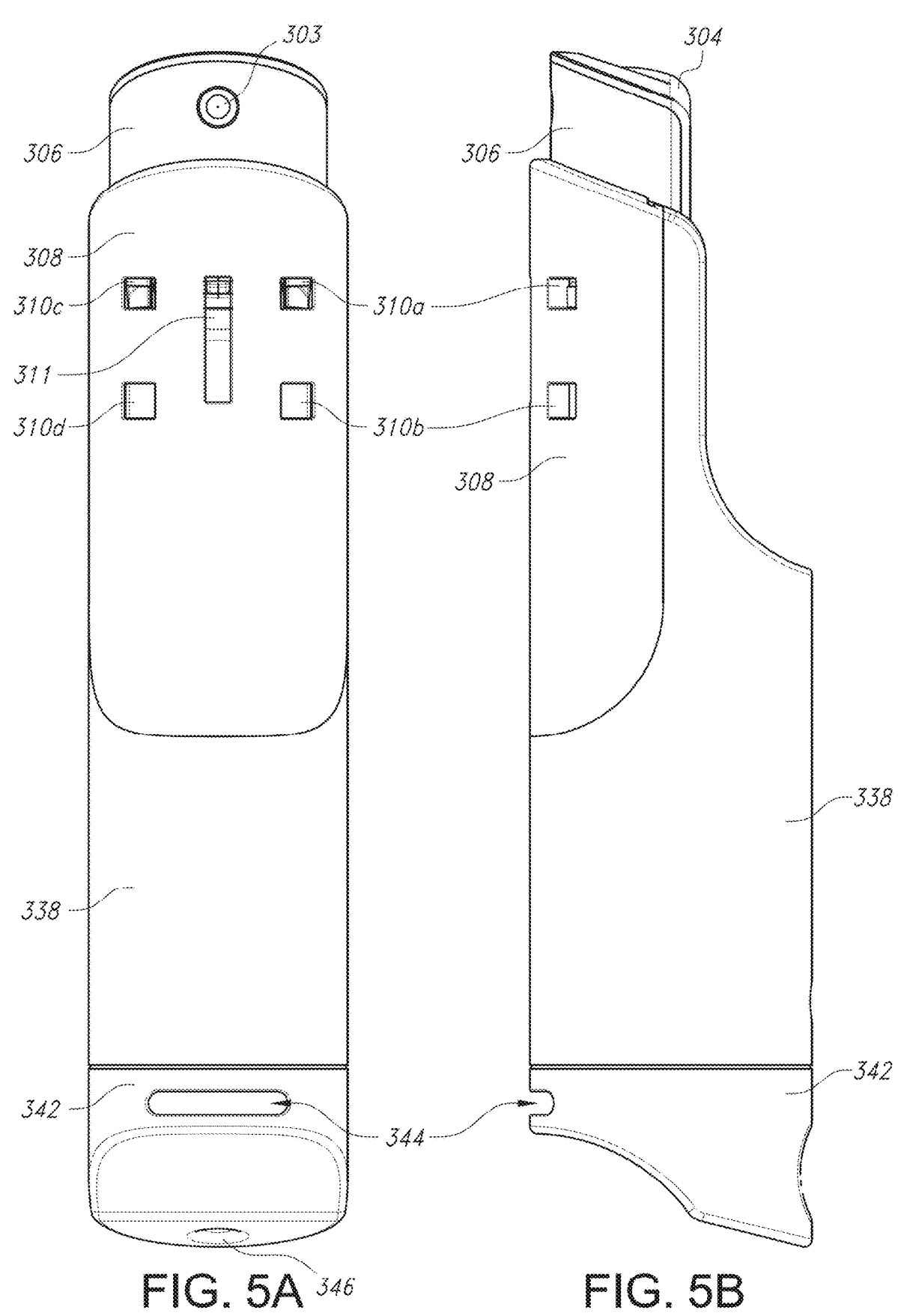

FIG. 5A-D depict perspective views of the smart NRT device with the dispenser head in an operative position (e.g., unlocked position). FIG. 5A shows a front view of the smart NRT device, such as device 100. As shown in FIG. 5A, the dispensing device 100 may comprise the cover 308, the main housing portion 338, the mouthpiece 342, and a dispenser head. The dispenser head may comprise the outlet 303, the face portion 306, and the cap portion 304. The mouthpiece 342 may comprise the oblong aperture 344 and the circular aperture 346. The cover 308 may comprise square apertures 310a, 310b, 310c, and 310d. The cover 308 may comprise the central slot 311.

The device 100 can be put into a use a configuration to allow for the dispensing of the nicotine formulation contained within the device 100. As shown in FIG. 5A, when in the operative position, the outlet 303 may be unobstructed such that the nicotine formulation may be dispensed. The operative position of device 100 may allow the dispenser head to extend outside the housing and the cover 308. For example, as shown in FIG. 5B, the dispenser head may extend beyond an edge of the cover 308 and/or an edge of the main housing portion 338.

FIG. 5C shows that the face portion 306 of the dispenser head, which has been raised from the main housing portion 338 such that the lower section of the flat rear wall 307 of the face portion 306 may be seen. The flat rear wall 307 may be made of a clear window such that a portion of the flat rear wall 307 may act of as a window, which may allow QR code 323 to be seen. The QR code 323 may be affixed to the vial 324.

As shown in FIG. 5D, the dispenser 337 may be raised within the main housing portion 338 such that space can be made to allow a lockout mechanism 1004 to move. As further described herein, the amount of space may allow the lockout mechanism 1004 to move between a first position (e.g., operative position) that may allow an actuating member to move so as to actuate the dispenser and a second position (e.g., non-operative) position that may prevent the actuating member from moving.

Figures 6A, 6B:
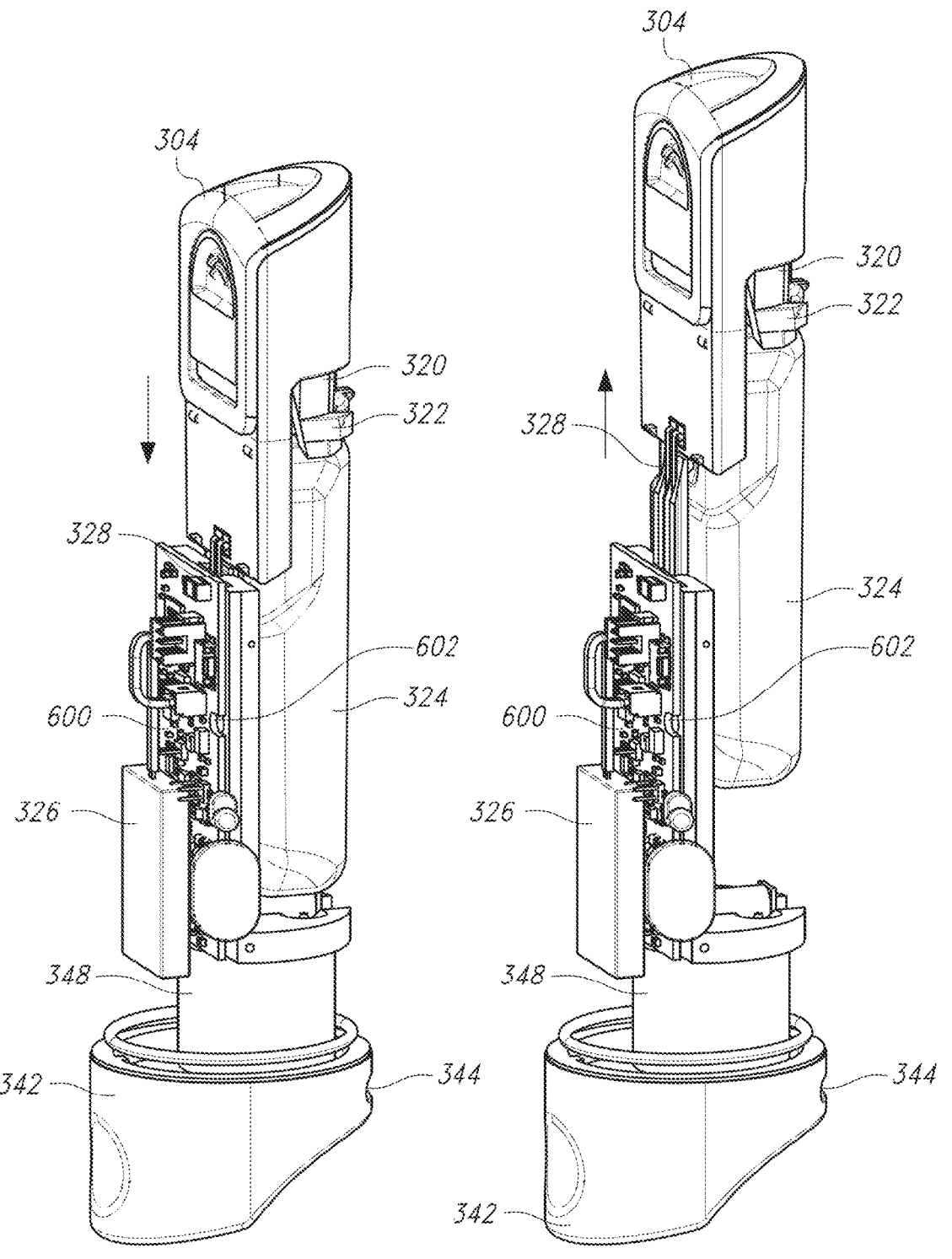
FIGS. 6A-B depict example schematic views of one or more components within the smart NRT device that may be used to dispense a nicotine formulation.

FIGS. 6A-B depict example schematic views of one or more components within the smart NRT device that may be used to dispense a nicotine formulation. As described herein, a dispenser may comprise a number of sub-components: a dispenser body in the form of a vial 324, a dispensing mechanism, a collar 320, a locking lever 322, and an actuating member. The dispensing mechanism may be in the form of a pump mechanism. The collar 320 may be for securing the pump mechanism 400 to the vial 324. The actuating member may be the dispenser head 339, which may include cap portion 304. The locking lever 322 may engage the collar 320 such that the locking lever 322 may be secured to the collar 320.

FIG. 6A depicts an example schematic view of the smart NRT device when a vial has been inserted into the housing. When the vial 324 is inserted into the housing, the vial 324, the locking lever 322, the collar 320, or cap portion 304 of the dispensing head 339 may come in contact with the carriage 328. The insertion of the vial 324 may cause another component within the device 100 to move in such a way as to contact the carriage 328.

For example, the vial 324 may be connected to the cap portion 304 of the dispenser head 339 via the locking lever 322 and/or the collar 320. The cap portion 304 of the dispensing head 339 be in contact with the carriage 328. When the vial 324 is inserted into the housing, the cap portion 304 may press down on the carriage 328, and the latching elements of the locking lever 322 may engage with the square aperture 310b and the square aperture 310d. The latching elements of the locking lever 322 may connect with the square aperture 310b and the square aperture 310d that may allow the device 100 to be locked into a non-operative position where the dispenser head 339 may be flush with or below an edge of the main housing portion 338. The carriage 328 may be connected to one or more biasing members, such as a spring, such that the carriage 328 may be pressed against the cap portion 304.

The contact with the carriage 328 may cause the carriage 328 to move, and a sensor may sense the movement. Upon sensing the movement of the carriage 328, the sensor may send a signal indicating that the vial 324 has been inserted. This may allow the device 100 to determine when the 324 vial is inserted into the housing. The device 100 may use a sensor to detect a QR code or chip associated with the vial 324. The device 100 may use a wire contact to connect to wire trace or chip associated with the vial 324. The device 100 may use the QR code, chip, and/or wire trace to determine an amount of nicotine formulation that can be dispensed from the vial 324, a volume of nicotine formulation within the vial 324, a strength of the nicotine formulation within the vial 324, an expiration for the nicotine formulation within the vial 324, and/or the like.

The vial 324, the locking lever 322, or the collar 320 may remain in contact with the carriage 328 or may remain in contact with a component that is in contact with the carriage 328. For example, the vial 324 may be connected to the cap portion 304 via the locking lever 322 and the collar 320.

When the dispenser is actuated, the actuation motion may cause the carriage 328 to move. For example, the actuation motion may exert a downward pressure on the carriage 328 and may cause the carriage 328 to move downward towards the distal end of the housing where the mouthpiece may be located. The movement may be sensed by a sensor. The device 100 may use the sensor to determine that the movement may be indicative of a dose of nicotine formulation being dispensed. In determining that the dose of nicotine formulation may have been dispensed, the device 100 may determine that the carriage 328 may have moved beyond a threshold. The threshold may be selected to prevent false positive. For example, the threshold may be selected to ensure that small movements of the carriage 328, such as those that may occur when the device 100 is shaken or dropped, are not determined to be indicative of nicotine formulation being dispensed.

The carriage 328 may be made of a magnetic material or may comprise a magnetic component. For example, the carriage 328 may comprise a bore and magnetic component, such as a small magnet, may be fit into the bore (e.g., press fit). An actuation motion may cause the carriage 328 to move towards the carbon monoxide sensor such that the carriage 328 or a magnetic component of the carriage may pass over a sensor that may sense the magnetic presence of the magnetic material. For example, the sensor may be a Hall effect sensor, and the movement of the carriage 328 may be detected by measuring the magnitude of a magnetic field produced by the magnetic material or a magnetic component of the carriage 328.

The motion and direction of the carriage 328 may be detected using one or more sensors. For example, the carriage 328 may pass over one or more Hall effect sensors, and the sequence of detection may indicate which direction the carriage 328 is moving.

The carriage 328 may be used in conjunction with a sensor to determine when a dose of the nicotine formulation was dispensed. For example, the device 100 may use the sensor to detect that the carriage 328 has moved, which indicates that the dose of the nicotine formulation was dispensed. The device 100 may record the time that the dose was dispensed, where the dose was dispensed, and/or how many times a dose was dispensed. For example, the device 100 may record a number of dosages remaining in the vial 324.

In examples, the device 100 may detect a movement of the carriage 328 indicates that the vial 324 was inserted. The device 100 may detect a number of follow-up movements of the carriage 328 that may indicate that the pumping mechanism was primed. The device 100 may determine to ignore the priming motion by the carriage 328 and may not consider it as a dispensing of the nicotine formulation.

The movement of the carriage 328 may be controlled by the carriage frame 329 such that the carriage 328 may be prevented from contacting the carbon monoxide sensor 348. This may be done, for example, to ensure that the carbon monoxide sensor 348 is not damaged by an impact from the carriage 328.

FIG. 6B depicts an example schematic view of the smart NRT device when a vial is being removed from the housing. When the vial 324 is removed from the housing, the vial 324, the locking lever 322, the collar 320, or the cap portion 304 of the dispensing head 339 may remain in contact with the carriage 328 until the vial 324 is removed. The removal of the vial 324 may cause another component within the device 100 to move in such a way as to remain in contact with the carriage 328.

For example, the vial 324 may be connected to the cap portion 304 of the dispenser head 339 via the locking lever 322 and/or the collar 320. The cap portion 304 of the dispensing head 339 be in contact with the carriage 328. When the vial 324 is removed from the housing, the latching elements of the locking lever 322 may disengage with the square aperture 310b and the square aperture 310d. The latching elements of the locking lever 322 may disconnect with the square aperture 310b and the square aperture 310d to allow the carriage 328 to push the dispensing head above an edge of the main housing portion 338 such that the vial 324 may be removed.

The device 100 may detect that a movement of the carriage 328 indicates that the vial 324 was removed. The device 100 may detect the removal of the vial 324 when the carriage has moved beyond a threshold. For example, the device 100 may detect that the carriage has moved past one or more Hall effect sensors in a sequence that would indicate removal of the vial.

Figure 7:
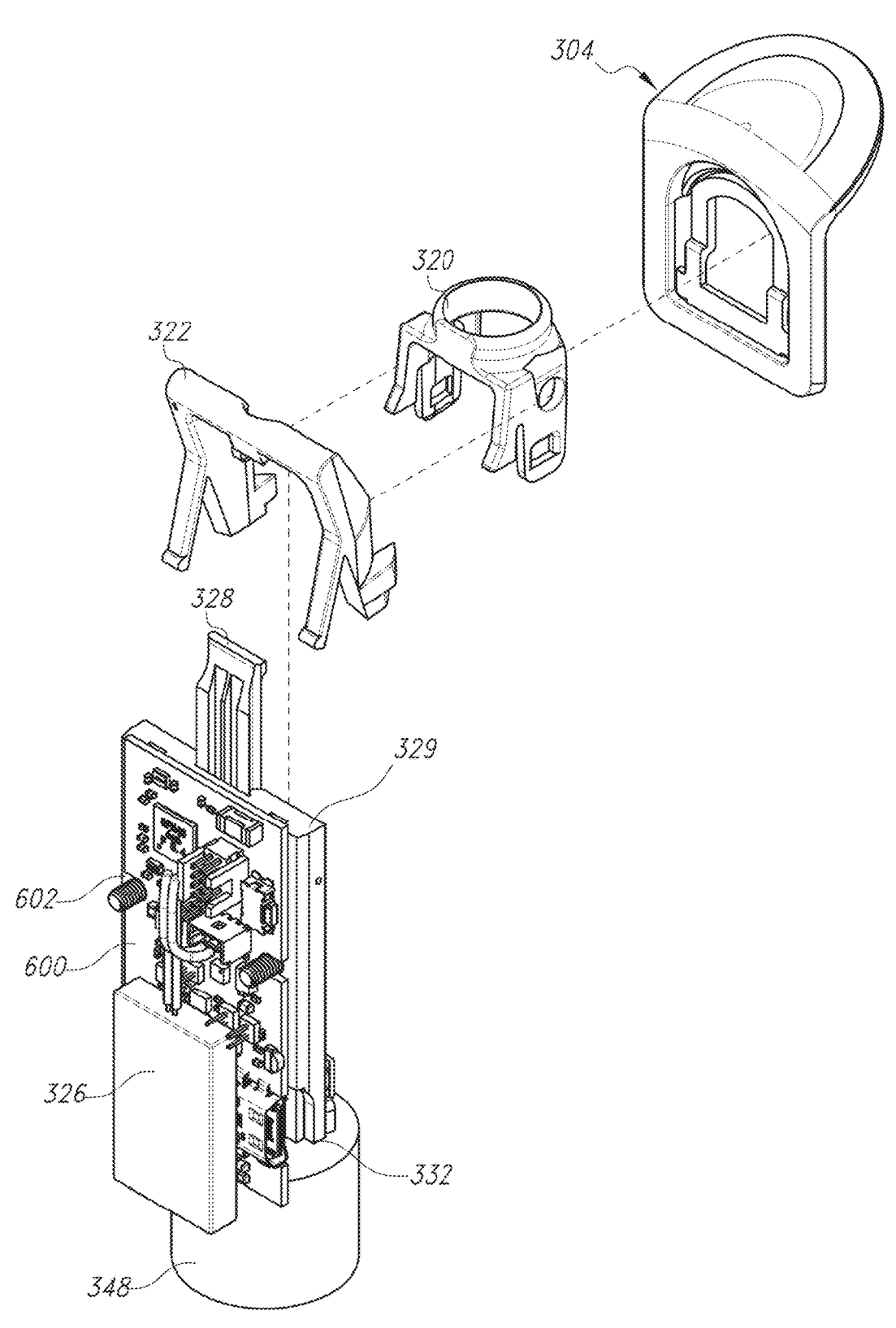
FIG. 7 depicts a schematic view of components within the smart NRT device that may be used to dispense nicotine formulation and/or record that nicotine formulation has been dispensed.

FIG. 7 depicts a schematic view of components within the smart NRT device that may be used to dispense nicotine and/or record that nicotine was dispensed. As shown in FIG. 7, the carriage frame 329 may comprise a pair of legs depending from the ends of a connecting yoke portion that may extended perpendicularly to each of the legs. The pair of legs belonging to the carriage frame 329 may terminate a distance above the carbon monoxide sensor 348 to prevent the carriage 328 from coming in contact with the carbon monoxide sensor 348.

The yoke portion of the carriage frame 329 may have a recessed or cut away portion in the center. The cut away portion of the yoke may allow the carriage 328 to lay within the cut away portion of the yoke portion of the carriage frame 329 such that the carriage 328 may lay flush with carriage frame 329 while being able to move relative to the carriage frame 329. The carriage 328 may have an end that may extend a distance beyond the carriage frame 329 and may terminate in a projecting foot. For example, the projecting foot may be positioned at the distal end of the carriage 328. The projecting foot of the carriage 328 may be in contact with the vial 324, the locking lever 322, the collar 320, and/or the cap portion 304 of the dispensing head. For example, the projecting foot of the carriage 328 may be in contact with the cap portion 304, such that the carriage 328 may move when a vial is inserted, when the smart NRT device is actuated to dispense nicotine, and/or when a vial is removed.

The carriage frame 329 may be attached to electronics 600, for example using one or more screws. The electronics 600 may comprise a PCB with a number of chips mounted thereon. The PCB may include castellated edges, such as castellated edge 602, to facilitate its mounting on the back face of the carriage frame 329. The electronics 600 may be attached to a battery pack 326. The battery pack 600 may be affixed to a face of the PCB of electronics 600 that faces away from the carriage frame 329. The electronics 600 may be interposed between the battery pack 326.

Figure 8:
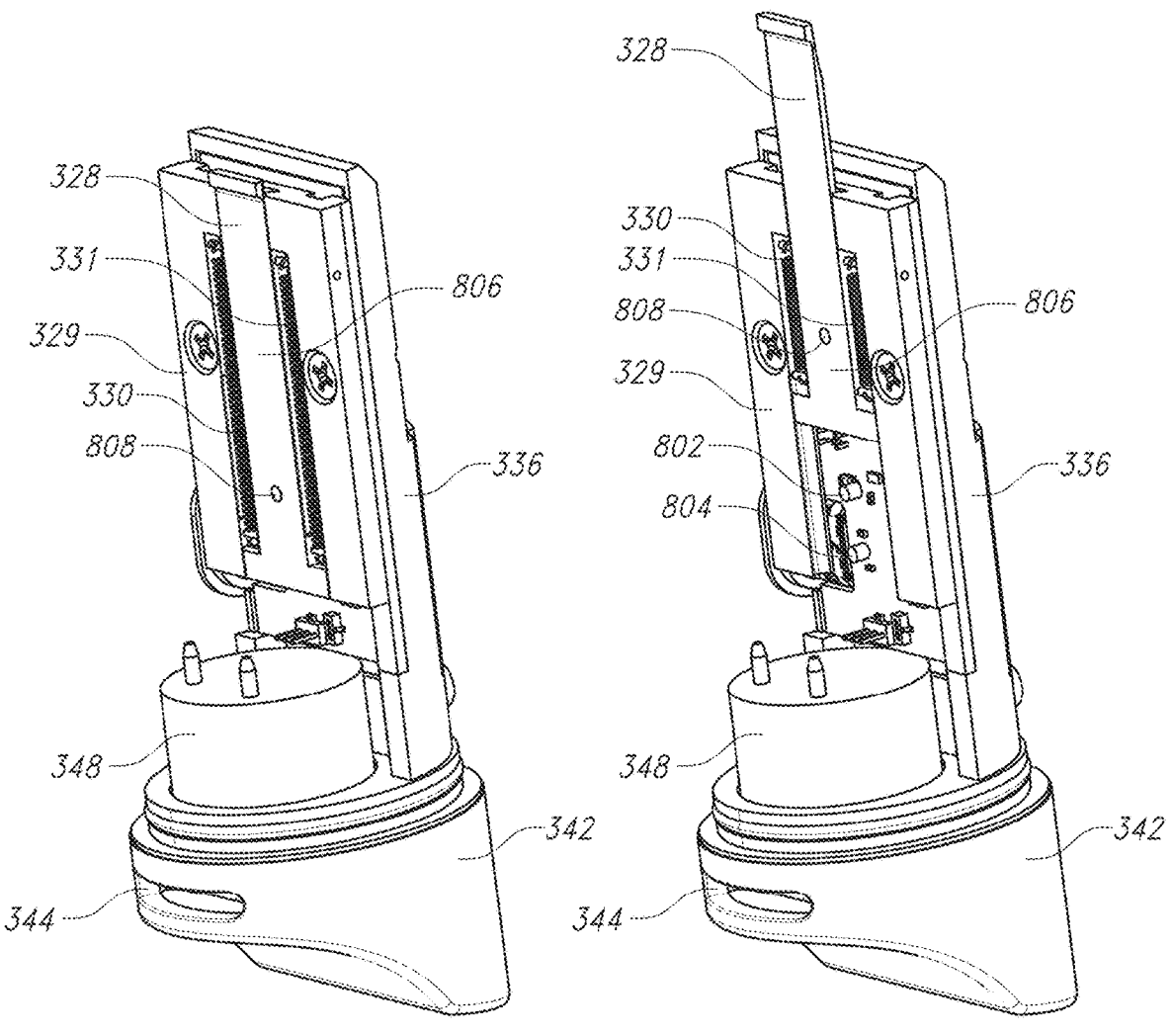
FIGS. 8A-B depict schematic views of a carriage system within the smart NRT device that may be used to detect and/or record when a vial is inserted, when a vial is removed, and/or when nicotine was dispensed.

FIGS. 8A-B depict schematic views of a carriage system within the smart NRT device that may be used to detect and/or record when a vial is inserted, when a vial is removed, and/or when nicotine is dispensed.

As shown in FIG. 8A, the carriage 328 may lay within the cut away portion of the yoke of the carriage frame 329. One end of the carriage 328 may terminal in a projecting foot and the opposing end of the carriage 328 may terminal in a T-shape. The carriage 328 may be of a long rectangular shape, where the length runs parallel to the carriage frame 329. The T-shape of the carriage 328 may be the width of an opening created by the two legs of the carriage frame 329. Above the T-shape may be an aperture through the carriage 328 that allows for a pin to be placed through the carriage 328. The pin may be perpendicular to the length of carriage 328. The pin may be affixed to a spring 330 and a spring 331.

The carriage 328 may be made of a magnetic material or may comprise a magnetic component. For example, the carriage 328 may comprise a bore and a magnetic component 808, which may be a small magnet, may be fit into the bore (e.g., press fit).

The spring 330 and the spring 331 may be biasing members and may control the movement of the carriage 328. For example, the spring 330 and the spring 331 may bias towards the yoke of the carriage frame 329 such that the T-shape of the carriage 328 may be pulled towards the yoke of the carriage frame 329. The carriage 328 may come in contact with the cap portion 304 (not shown) of the dispensing head. The carriage 328 may push the cap portion 304 upward so that dispenser (e.g., dispenser 337 shown in FIGS. 3A-C) can be placed in an operative position (e.g., FIG. 5A-B) or into a position where a vial may be removed or/inserted (e.g., FIG. 6B). The carriage 328 may push the cap portion 304 upward so that resistance may be provided when the dispenser is pushed down into a locked position and/or non-operative position (e.g., FIGS. 5C-5D).

FIG. 8A shows the carriage system in a position that may be used to detect and/or record when a vial is inserted or when nicotine was dispensed. The spring 330 and the spring 331 may provide a resistance to indicate to the user that the vial 324 is being inserted properly. For example, the spring 300 and the spring 311 may be biased members such that the carriage 328 connects with the cap portion 304 and presses the cap portion 304 upward such that the dispenser is extended out of the housing. The spring 300 and the spring 331 may provide resistance such that when the vial 324 is being inserted, the carriage 328 may move a distance as it maintains contact with the cap portion 304. This distance may be detected by a sensor and may indicate that the vial 324 was inserted.

The spring 330 and the spring 331 may provide resistance such that when the device 100 is actuated so as to dispense the nicotine formulation, the resistance from the spring 330 and the spring 331 may control the movement of the carriage 328 such that the carriage 328 moves a distance. This distance may be detected by a sensor and may indicate that the nicotine formulation has been dispensed.

The carriage frame 329 may be attached to the body frame 336. The body frame 336 may be attached to the main housing portion 338, for example, using a screw. The body frame 336 may have a hollow cylindrical neck portion that provide an open mouth at one end. The carbon monoxide sensor 348 may be seated within the mouth of the body frame 336 and may extend past an edge of the mouth of the body frame 336. The mouthpiece 342 may be seated on the rim of the mouth of the body frame 336 such that the mouthpiece 342 may seal the mouth of the body frame 336 with the carbon monoxide sensor 348 extending down into the upper opening 343 of the mouthpiece 342.

FIG. 8B shows the carriage system in a position that may be used to detect and/or record when a vial is being removed when nicotine was dispensed. The spring 330 and the spring 331 are connected to the carriage 328 such that the carriage 328 pushes upward against the cap portion 304. The spring 330 and the spring 331 may apply pressure to the cap portion 304 via the carriage 328 so that the dispenser can be pushed out of the housing to allow the vial 324 to be removed. The spring 330 and the spring 331 may apply pressure to the cap portion 304 via the carriage 328 so that the dispenser can be moved within the housing to allow the device to be placed in an operative position.

The spring 300 and the spring 331 may provide resistance such that when the vial 324 is removed, the carriage 328 may move a distance. This distance may be detected by a sensor and may indicate that the vial 324 was removed.

The spring 330 and the spring 331 may provide resistance such that when the device 100 is actuated to dispense the nicotine formulation, the resistance from the spring 330 and the spring 331 may control the movement of the carriage 328 such that the carriage 328 may move a distance. This distance may be detected by a sensor and may indicate that the nicotine formulation has been dispensed.

The carriage 328 may be made of a magnetic material or may comprise a magnetic component. For example, the carriage 328 may comprise a bore and magnetic component 808, which may be a small magnet, may be fit into the bore (e.g., press fit). As the carriage 328 moves, it may pass over a sensor 802, a sensor 804, and a sensor 806. The sensor 806 may be located behind the carriage 328 as shown in FIGS. 8A and 8B. The sensor 806 and may be located so that the sensor 806 may be in proximity to the magnetic component 808 when the T-shape of the carriage 328 has been pulled towards the yoke of the carriage frame 329.

The sensor 802, the sensor 804, and the sensor 806 may detect the movement of the carriage 328. For example, the sensor 802, the sensor 804, and the sensor 806 may be Hall effect sensors, and the movement of the carriage 328 may be detected by measuring the magnitude of a magnetic field produced by the magnetic material of the carriage 328 and/or the magnetic component 808.

An actuation motion may cause the carriage 328 to move towards the carbon monoxide sensor 348 such that the carriage 328 and/or the magnetic component 808 may pass over the sensor 802, the sensor 804, and the sensor 806.

The motion and direction of the carriage 328 may be detected using one or more sensors. For example, the carriage 328 may pass over one or more Hall effect sensors, and the sequence of detection may indicate which direction the carriage 328 is moving. It may be determined that a vial has been inserted when the magnetic component 808 passes over or is in proximity to the sensor 806. It may be determined that a vial has been removed when the magnetic component 808 passes over the sensor 804, passes over the sensor 802, and passes over or is in proximity to the sensor 806. It may be determined that nicotine was dispensed when the magnetic component 808 passes over the sensor 802 and passes over or is in proximity to the sensor 804.

The magnetic component 808 and/or the carriage 328 may be used in conjunction with the sensor 802, the sensor 804, and the sensor 806 to determine that a movement of the carriage 328 and/or the magnetic component 808 indicates that the vial 324 was inserted. The sensor 802, the sensor 804, and the sensor 806 may detect a number of follow-up movements of the carriage 328 and/or the magnetic component 808 that may indicate that the pumping mechanism was primed. The device 100 may determine to ignore the priming motion and may not consider it as a dispensing of the nicotine formulation.

The magnet component 808 may be moved into or may be in a position that may be on top of the sensor 804 (e.g., FIG. 8A). This may occur, for example, when the nozzle 303 may be in a retracted position within the main housing portion 338 and the dispenser head 339 may be flush with or below the upper edge of the main housing portion 338.

The magnetic component 808 may be moved into or may be in a position that may be on top of the sensor 806 (e.g., FIG. 8B). This may occur, for example, when the dispenser head 339 may be in an extended position and the nozzle 303 may be outside of the main housing portion 338. With regard to FIG. 8B, the sensor 806 is not visible because it is covered by the carriage 328 that includes the magnet component 808.

The magnetic component 808 and/or the carriage 328 may be used in conjunction with the sensor 802, the sensor 804, and the sensor 806 to determine when a dose of the nicotine formulation was dispensed. For example, the sensor 802, the sensor 804, and the sensor 806 may detect that the carriage 328 and/or the magnetic component 808 have moved, which indicates that the dose of the nicotine formulation was dispensed.

The smart NRT device may determine that nicotine is dispensed when the magnet component 808 moves a position that may be in proximity to or overlapped with the sensor 806 to a position that may be in proximity to or overlapped with the sensor 802. A user may allow the actuator to move or bounce back up into an extended position, which may cause the magnet component 808 to return to a position that may be in proximity to or overlapped with the sensor 806. The user may push the actuator down to lock it within the housing, which may cause the magnet component 808 to move into a position that may be in proximity to or overlapped with the sensor 804.

Figure 9:
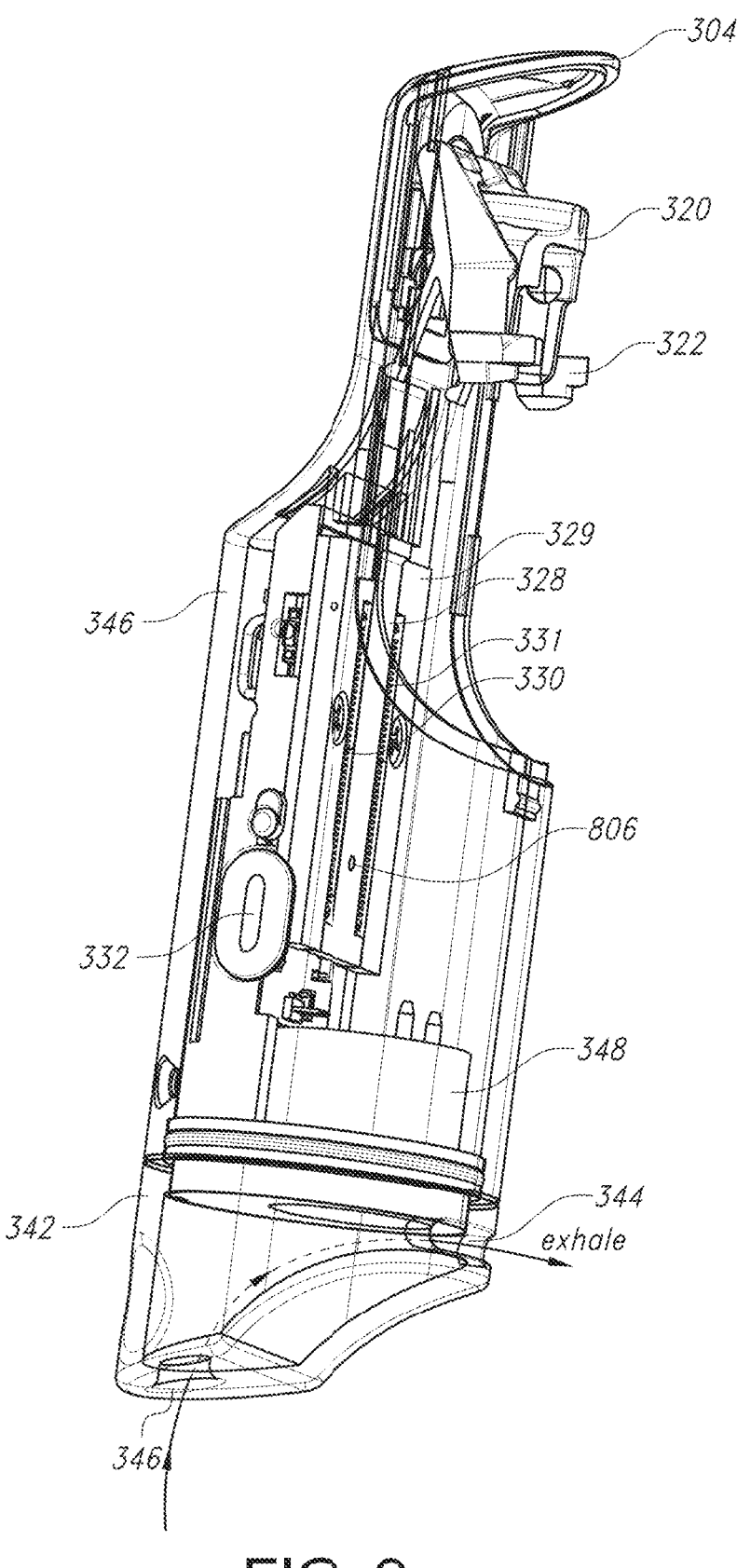
FIG. 9 depicts a schematic view of the smart NRT device that may include a sensor, such as a carbon monoxide sensor, to detect tobacco use by a user.

FIG. 9 depicts a schematic view of the smart NRT device that may include a sensor, such as a carbon monoxide sensor, to detect tobacco user by a user. As shown in FIG. 9, the mouthpiece 342 may be at an end of the housing of the device 100. For example, the mouthpiece 342 may be the opposite end of the dispenser head. The mouthpiece 342 may be designed to allow an exhalation from a user to flow through the mouthpiece and past a carbon monoxide sensor. For example, a user may exhale into the circular aperture 346 such that the user's exhalation passes over the carbon monoxide sensor 348 and exists the mouthpiece 342 at the oblong aperture 344. The carbon monoxide sensor 348 may use an exhalation from the user to determine a carbon monoxide level within the user. For example, the carbon monoxide sensor 348 may determine a carbon monoxide level from the flow of air through the mouthpiece 342. The device 100 may use the carbon monoxide level to determine the amount of carbon monoxide in the user. The device 100 may determine that the amount of carbon monoxide indicates that the user may have consumed one or more tobacco products.

Figures 10A, 10B, 10C:
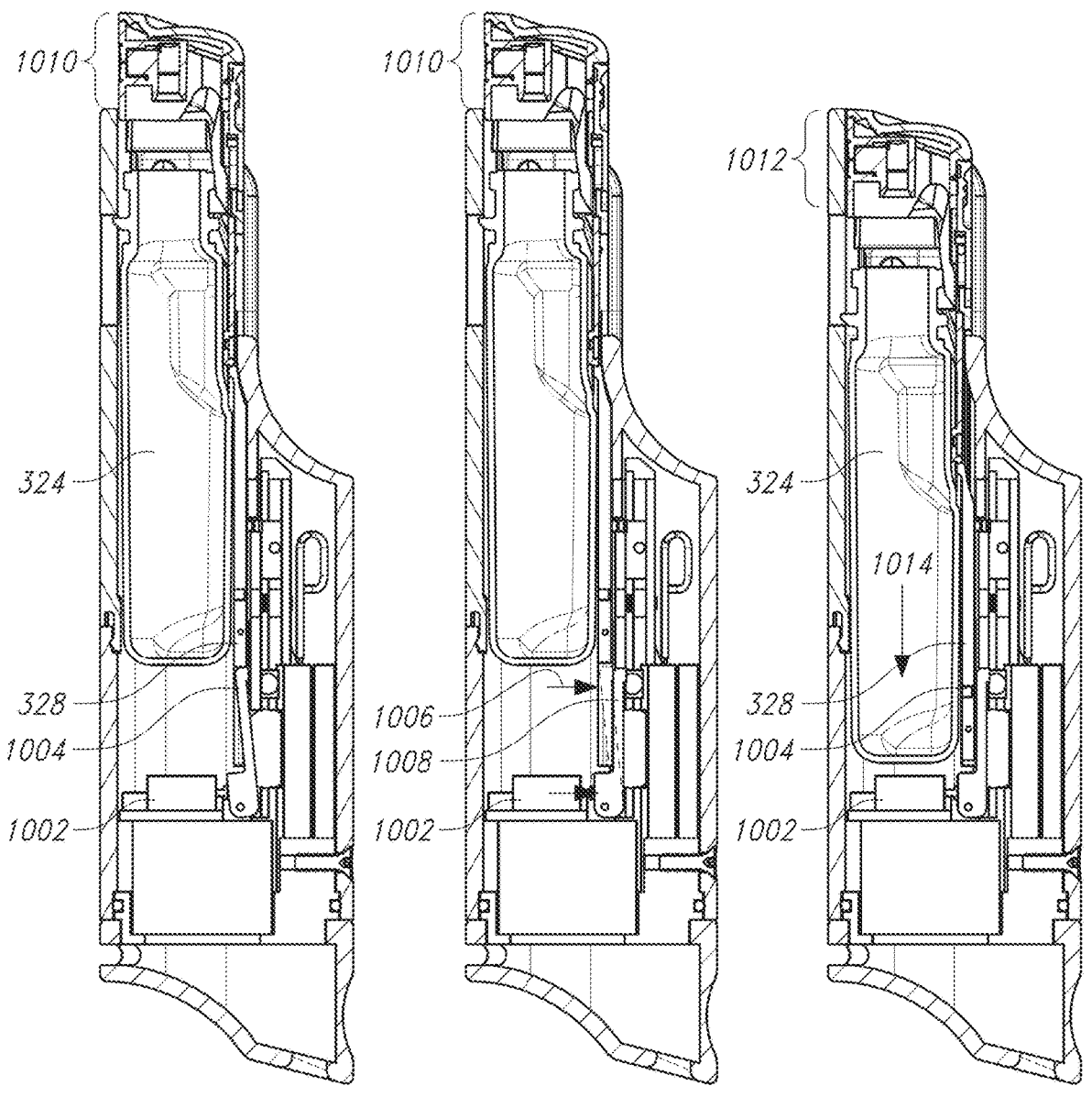
FIGS. 10A-C show a schematic views of a lockout mechanism within the smart NRT device that may be used to prevent a nicotine formulation from being dispensed.

FIG. 10 shows a schematic view of a lockout mechanism within the smart NRT device that may be used to prevent a nicotine formulation from being dispensed. The device 100 may include a solenoid 1002 that may be operatively connected to a lockout mechanism 104. As shown in FIG. 10A, device 100 may be in an operative position such that, as shown at 1010, the dispenser head may extend above the main housing portion. This may allow the dispenser to move within the main housing portion so that the vial 324 provides an amount of space that may allow the lockout mechanism 1004 to move between a first position (e.g., an operative position) that may allow an actuating member to move to actuate the dispenser and a second position (e.g., non-operative position) that may prevent the actuating member from moving.

The lockout mechanism 1004 may be used to prevent action of the dispenser head. For example, as shown in FIG. 10A, lockout mechanism 1004 may contact the carriage 328. The lockout mechanism 1004 may block the carriage 328 from moving down, which may prevent a spray actuation and may prevent the device 100 from being moved to a non-operative position. The lockout mechanism 1004 may be placed in the operative position by the solenoid 1002. For example, the device 100 may determine that the vial 324 may not have been authenticated and may send a signal to the solenoid 1002 that causes solenoid to move the lockout mechanism 1004 into the blocking or non-operative position that prevents the actuating member from moving.

The device 100 may determine the vial 324 may have been authenticated and may send a signal to the solenoid 1002 that causes the solenoid 1002 to move the lockout mechanism 1004 into an operative position. For example, as shown at FIG. 10B, the lockout mechanism 1004 has moved to position 1008, which allows a space at 1006 to occur such that the carriage 328 may move downward.

The lockout mechanism 1004 may be used to prevent a user from dispensing more than an amount of nicotine. For example, a user may be allowed an amount of nicotine that they may use for a time period, such as a day. If the user attempts to go over the amount of nicotine that they may use, the solenoid 1002 may receive a signal to move the lockout mechanism 1004 to the non-operative position such that the lockout mechanism 1004 may make contact with the carriage 328, and the user may not be able to dispense nicotine using the device 100.

The lockout mechanism 1004 may be used to allow a user to dispense nicotine. For example, it may be predicted that a user may have a craving. And the user may receive a notification to dispense a dose nicotine using the device 100. The solenoid 1002 may receive a signal to move the lockout mechanism 1004 to the operative position such that lockout mechanism may not contact the carriage 328 and the user may be able to dispense nicotine using the device 100.

To allow the device 100 to move to a non-operative position, as shown in FIG. 10C, the solenoid 1002 may cause the lockout mechanism 1004 to move to an operative position to avoid contact with the carriage 328. The carriage 328 may move down along with dispenser. For example, the dispenser may move into the housing so that the device 100 may become more compact and may be in a non-operative position. Although the solenoid 1002 may be shown, the solenoid 1002 may be replaced with another compatible component such as a piezoelectric motor.

A user may interact with the NRT application and/or behavioral-support application, for example, installed on a smart phone, a tablet, and/or on smart watch. As described with respect to FIG. 2B, the application may receive data from the smart NRT device (e.g., a hand-held nicotine formulation dispensing device), the smart watch, and/or a remote server. The application may analyze the received data and provide a personalized program for the user.

A personalized smoking/nicotine cessation program may include a default 12-week journey, with the biometric feedback and behavioral patterns. The journey can be dynamic and customized to the specific user of the system during the program. For example, the duration of the program may be determined based on the user's smoking behavior prior to using the NRT device. For example, if the user is a light smoker, the program duration may be shorter than 12 weeks. A longer program, (e.g., longer than 12 weeks), may be created for a long-term heavy smoker. The cessation program duration may be updated based on the various collected data, as described herein. The cessation program can also be customized to users of other tobacco products, electronic cigarettes and vaping products. For example, the cessation program may be customized to user that may consume nicotine from a cigarette, tobacco product, electronic cigarette with nicotine, and/or an alternate source, such as a skin patch, chewing gum, nasal spray, inhaler, lozenge/tablet, oral spray, and the like.

The application may receive biometric data, which may be referred to as biomarker data, associated with the user, for example, from the smart watch, the smart phone, the smart NRT device, and/or other devices. For example, biological sensors of a smart watch may provide biometric data such as heart rate, heart rate variability, skin temperature, user gesture, and/or the like. Biometric data may be used to predict the onset of a craving or potential relapse in smoking or nicotine usage. Recommendations on coping strategies may be provided, via the application, based on the predicted craving or potential relapse in smoking or nicotine usage.

As described herein, the smart NRT device may include an accelerometer. User motion or gesture may be detected based on signals from the accelerometer. For example, user gesture information may be used to detect a user fidgeting. This information can be used to predict a craving and preemptively stop the craving by promoting the use of NRT or some behavioral exercise (such as breathing exercise).

The application may receive CO level information, for example, from the smart NRT device. Based upon biometric feedback and/or CO improvement information, health improvement related to cigarettes/nicotine reduction may be determined.

Figures 11A, 11B:
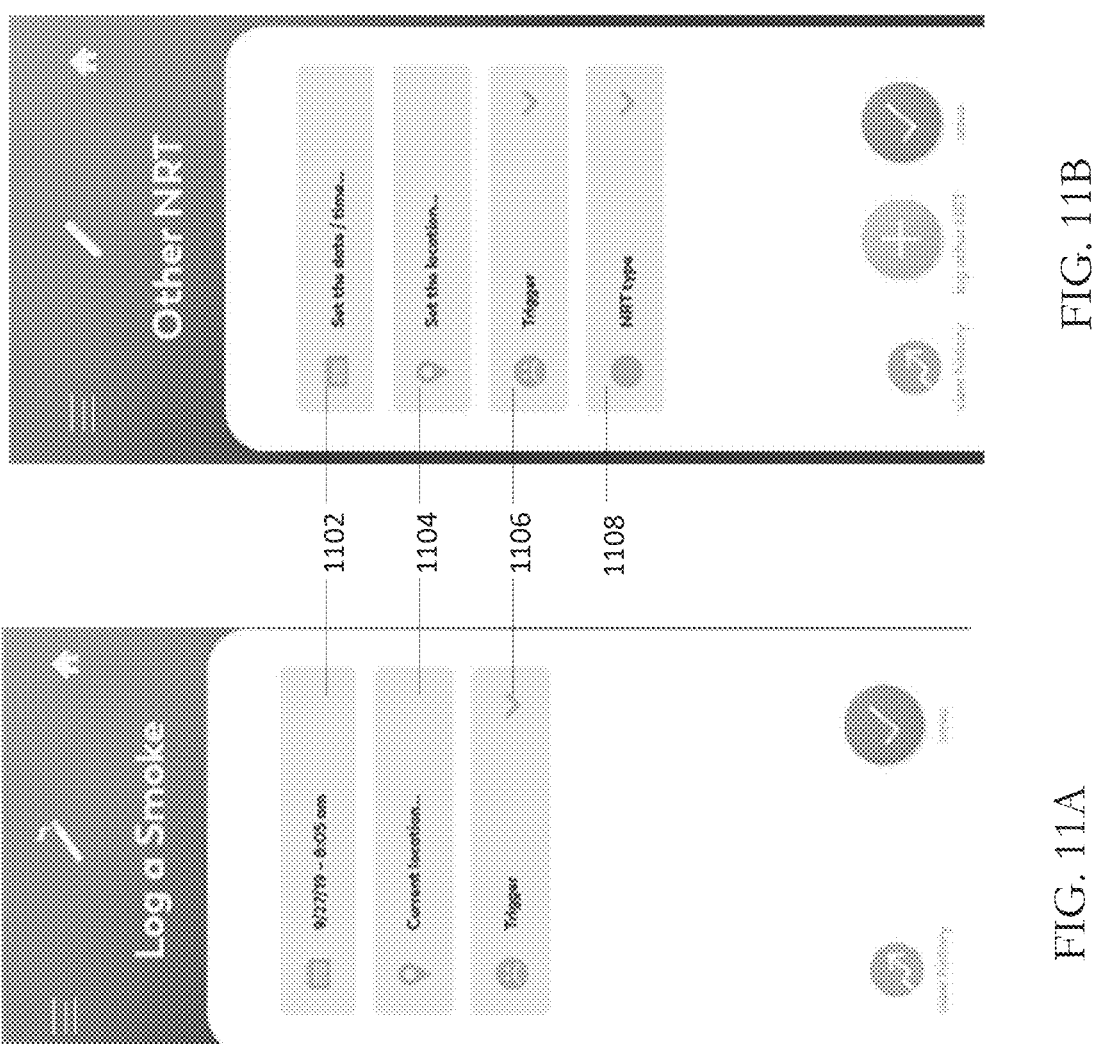
FIG. 11A depicts an example user interface for entering cigarette or other tobacco product consumption.
FIG. 11B depicts an example user interface for collecting nicotine intake related information.

FIG. 11A depicts an example user interface for entering cigarette consumption. FIG. 11B depicts an example user interface for collecting other NRT intake related information. The application may allow the user to enter cigarette and/or tobacco and/or electronic cigarette and/or vaping products and/or other NRT substance consumption information, such as the date and time of each smoke, the location, and/or an associated trigger. At 1102, a user may enter in a time and/or date when for when a smoking event occurred and/or a NRT event occurred. The event may have occurred in the past, may be occurring, or may occur in the future. For example, the user may plan to smoke and/or use nicotine after entering in the information. At 1104, the user may enter a location for the smoking event and/or NRT event. The location for the event may be entered manually by the user, or the user may allow the smartphone to determine the location (e.g., using a GPS associated with the smartphone). At 1106, the user may enter in a trigger that may have caused the smoking event and/or the NRT event. For example, the user may indicate that they had an increase in stress as a trigger. At 1108, the user may enter the type of nicotine formulation that was used. For example, the user may indicate that they used a nicotine gum, nicotine spray, and/or the like.

Recommendations for cigarettes/tobacco/electronic cigarette/vaping product/NRT reduction may be determined based on data including, but not limited to, user-reported triggers, system-derived triggers, user biometrics data, cigarette/tobacco/electronic cigarette/vaping product/NRT consumption tracking, user's age, gender, geographic location, and/or daily activities. For example, recommendations may be identified such that the user may start with easier occasions to reduce cigarette consumption or replace cigarette consumption with NRT use, and thus may increase likelihood of successful overall reduction and eventual elimination.

NRT/nicotine formulation intake information may be received, for example, from the nicotine formulation dispensing device. The intake information may include the amount of nicotine formulation dispensed and the time associated with the intake. NRT/nicotine formulation intake information may be tracked over time.

Information related to the carbon-monoxide level of the user may be received, for example, from the nicotine formulation dispensing device. The received user carbon-monoxide level may be time-stamped and tracked over time.

One or more triggers to a smoking event or NRT consumption may be derived. Triggers may be derived based on various data collected through various sources. For example, the application may receive data from other sources on the smartphone, for example a calendar, to identify activities that might present a trigger. For example, location-based triggers may be derived by correlating NRT dispense data with the user's location. Triggers may be continuously derived, updated, and/or removed based on the data collected.

Figure 12:
FIG. 12 depicts example user interface(s) for displaying progress made in the nicotine replacement therapy program.

FIG. 12 depicts example user interfaces for displaying progress made in the nicotine replacement therapy program. Information on health improvement may include, but not limited to, the reduction in CO level, and/or reduction in heart rate. At 1202, a goal may be presented to the user. The goal may indicate that the user is to reduce cigarette consumption by an amount. For example, at 1202, the goal may indicate that the user is to replace 50% of the cigarettes that would be consumed with a nicotine formulation. The goal may also indicate a week of a cessation program phase that the users may be in. At 1204, a program progress may be displayed. The program progress may indicate an amount of nicotine that a user may consume. For example, the program progress may indicate how much nicotine a user may consume and how much nicotine that the user has consumed. This may be used, for example, to indicate to a user how much nicotine they may consume. At 1206, the interface may include a count of cigarettes consumed by a user and/or an amount of tobacco consumer by a user and/or a count of electronic cigarettes or vaping products consumed by a user and/or a count of nicotine formulation consumed by a user. The interface may include a count of the days that a user has been without a consuming nicotine from a cigarette, tobacco product, electronic cigarette with nicotine, and/or an alternate source, such as a skin patch, chewing gum, nasal spray, inhaler, lozenge/tablet, oral spray, and the like.

At 1208, the interface may indicate which week out of a program a user may be in. For example, the interface may indicate that the user is in week 4 of a 12 week program. At 1210, the interface may indicate an amount of money saved by quitting smoking. Providing improvement information at moment (e.g., key moments) in the journey may increase the likelihood that user will stay the course with the program. At 1212, the user interface may indicate that the application is connect to the smart NRT device, for example, via Bluetooth. At 1220, an indication of the battery life of the smart NRT device may be provided. At 1222, an indication of an amount of nicotine formulation within a vial associated with the smart NRT device may be provided.

FIG. 13 depicts example user interface(s) for indicating personalized weekly targets and plans. As shown in FIG. 13, the application may provide personalized weekly targets, and/or specifically timed daily/weekly support activities to address the habit changes that the user is going through at that stage in the journey.

At 1302, the user interface may indicate that the user may be in week 1 of the cessation program. There may be a goal associated with the week of the cessation program. For example, the goal of week 1 of the cessation program may be to replace 25% of the cigarettes a user may smoke with a nicotine formulation. There may be a daily action associated with the week of the cessation program. For example, the action for day 1 of week 1 of the cessation program may be to replace another daily cigarette.

At 1304, the user interface may indicate that the user may be in week 5 of the cessation program. There may be a goal associated with the week of the cessation program. For example, the goal of week 5 of the cessation program may to avoid smoking cigarettes and to focus on using nicotine formulation. There may be a daily action associated with the week of the cessation program. For example, the action for day 1 of week 5 of the cessation program may be to get a CO level for the user within a range or below a threshold.

At 1306, the user interface may indicate that the user may be in week 10 of the cessation program. There may be a goal associated with the week of the cessation program. For example, the goal of week 10 of the cessation program may be to reduce a user's dependence on nicotine formulation by 25%. There may be a daily action associated with the week of the cessation program. For example, the action for day 1 of week 10 of the cessation program may be to reduce the consumption of nicotine formulation by a dose.

FIG. 14 depicts example user interface(s) for creating a personalized cigarette replacement plan. A plan for a week, such as week 1, may include identifying the cigarettes to replace with NRT/nicotine formulation based on user's perceived stress levels, heart rates, triggers, and/or the like. For example, at 1402, the application may identify one or more cigarettes for a user to consider replacing with nicotine formulation based on a heart rate. A user may interact with the interface and may select one or more of the identified cigarettes. The user may be presented with a time and a heart rate that are associated with the selected cigarette. As another example, at 1402, the application may identify one or more cigarettes for a user to consider replacing with nicotine formulation based on a heart rate and a trigger. A user may interact with the interface and may select one or more of the identified cigarettes. The user may be presented with a time, a heart rate, and a trigger that are associated with the selected cigarette.

At 1406, the user may be presented with one or more cigarettes that the user may have selected to be replace with nicotine formulation. At 1406, reminders or events may be added to a calendar to remind the user of NRT/nicotine formulation use.

Figure 15C:
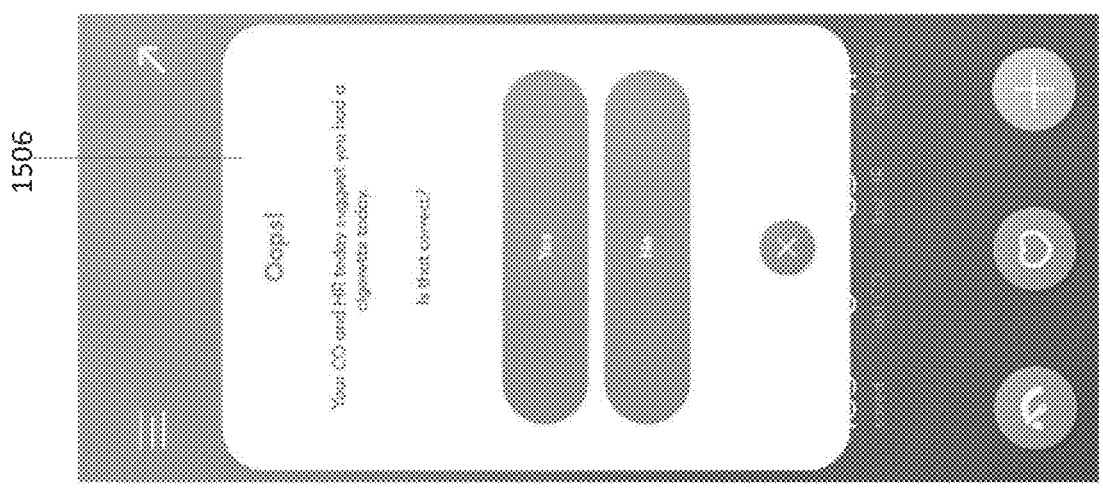
FIG. 15C depicts an example user interface for prompting a user to confirm cigarette or other tobacco product consumption.
Figure 15B:
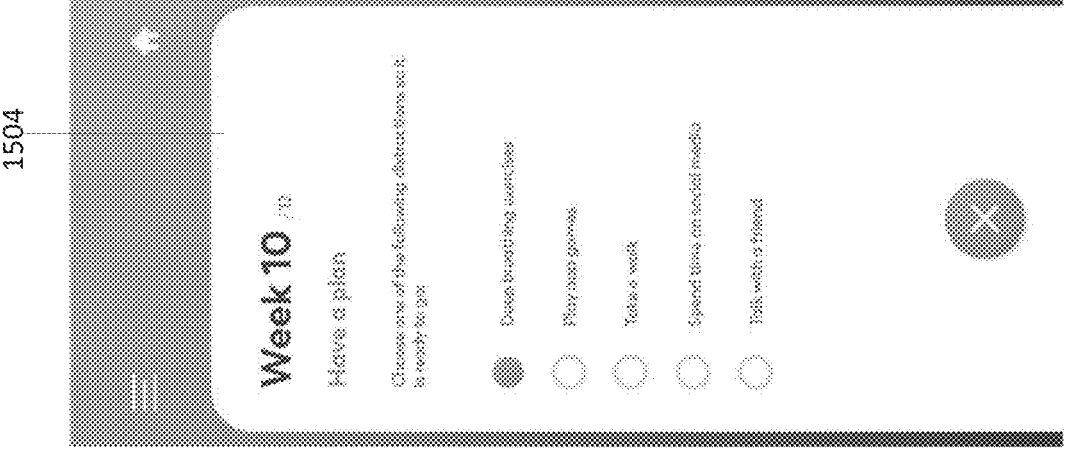
FIG. 15B depicts an example user interface for entering an action for coping with anticipated cravings.
Figure 15A:
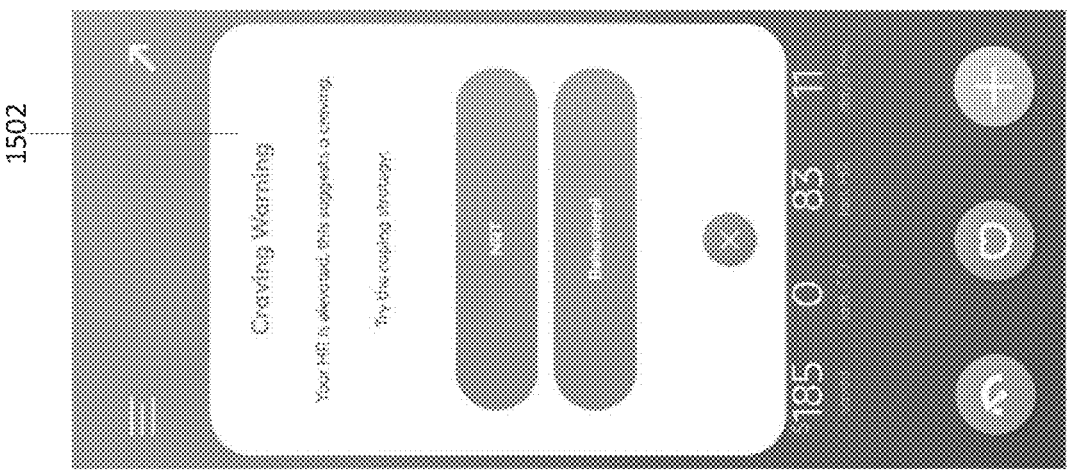
FIG. 15A depicts an example user interface for suggesting an action in advance of a predicted nicotine craving.

FIG. 15A depicts an example user interface for suggesting an action in advance of an anticipated craving. An anticipated craving time may be determined based on various data. For example, an anticipated craving time may be determined based on nicotine intake information, user CO level information, location information, the heart rate of the user, a heart rate change, skin temperature, a scheduled activity based on a calendar, and/or detected motion/user gesture (e.g., fidgeting). An indication suggesting an action in advance of the anticipated craving time may be provided. For example, use recommendations for NRT or behavioral coping technique(s) may be provided. As shown at 1502, a craving warning message may be displayed. Use of the nicotine formulation in NRT device may be proactively suggested in advance, anticipating potential cravings. An action to distract the user from the anticipated craving may be suggested. For example, at 1502, the user may be presented with an option to use NRT or to take a behavioral copying strategy.

FIG. 15B depicts an example user interface for the user to select an action for coping with an anticipated craving. For example, the user may have opted to take a behavioral coping strategy. At 1504, one or more suggested distractions may be selected for a specific week or a particular time period. The suggested distractions may include, a deep breathing exercise, playing a game (e.g., a video game or application), taking a walk, spending time on social media, talking with a friend, and/or the like.

FIG. 15C depicts an example user interface for prompting user to confirm cigarette consumption. For example, the user may have opted not to use a suggested coping strategy. The application may analyze the user's heart rate and CO level. The application may determine that the user may have consumed a cigarette based on the user's CO level data and/or the user's heart rate information. When detecting the user's cigarette consumption, at 1506, a message may be provided to allow the user to confirm cigarette consumption. The confirmation may be used to track the user's cigarette consumption information, and/or nicotine consumption information.

The application may send messages to the smart NRT device to control one or more components in the smart NRT device. For example, the application may send a message to the smart NRT device indicating the device should stop nicotine formulation dispensing, for example, for a period of time, or until receiving a dispense resume message. The application may send a message to the smart NRT device indicating that a dose of nicotine formulation can be dispensed. The application may send an indication of the amount of nicotine formulation that can be dispensed, for example, during a period of time, during a use, or until the receipt of a dispense resume indication. The dispense resume message may be sent after a period of time lapses, which can be determined based on various data collected and/or tracked as described herein.

Whether to initiate a nicotine formulation dispenser lockout may be determined. For example, the determination may be based on a nicotine threshold (e.g., a standard threshold or personalized threshold) for the user and the amount of nicotine that was previously consumed by the user. A lockout may be activated upon determining that the amount of nicotine consumed by the user (e.g., over a period of time) exceeds the nicotine threshold (e.g., associated with that period time). The amount of nicotine that was previously consumed by the user may be determined based on the tracked tobacco product or NRT consumption data and/or the level of carbon monoxide within the user. A lockout may be activated when determining that an inauthentic vial has been inserted into the NRT device. Authentication may be performed, for example, via QP code recognition. A lockout may be activated upon determining that the device is associated with an area where use of the substance is prohibited.

A standard nicotine threshold may include a number of sprays, such as 64 sprays. The threshed can be of other values, such as 60, 62, 66, 68 sprays or the like. Sprays pumped for priming purposes may be discounted or discard from spray counts.

A personalized nicotine threshold for the user may be determined based on one of more of considerations including, but not limited to, the level of CO within the user, user biometrics data, user's prior smoking habits, daily intake limit associated with the NRT program, tracked cigarette consumption, traced NRT consumption, user's age, gender, geographic location, and/or daily activities.

The amount of formulation that can be dispensed during a period time, (e.g., per use, per 30 minutes, per hour, per 24 hours) may be determined based on a predetermined nicotine intake limit, the stage of NRT program, the concentration of the nicotine formulation, the nicotine consumption reduction target, and/or the like.

The smart watch may provide a user interface to the user, for example, to display metrics related to the smoking cessation journey, how much NRT has been used during a period of time (e.g., within half an hour, within an hour, within 24 hours), cigarette usage, and/or the like. The metrics may be displayed against the smoking cessation program targets.

FIG. 16A depicts an example overview of a nicotine/smoking cessation program. A personalized smoking/nicotine cessation program may include a default journey, which may be a 12-week journey. The cessation program may be personalized for a user, for example, using biometric feedback and/or behavioral patterns. The journey may be dynamic and customized to the user of the system during the program. For example, the duration of the program may be determined based on the user's smoking behavior prior to using the NRT device. For example, if the user is a light smoker, the program duration may be shorter than 12 weeks. A longer program, (e.g., longer than 12 weeks), may be created for a long-term heavy smoker. As another example, the duration of the program may be determined and/or adjusted by a user. At 1602, the user may be presented with a personalized smoking/nicotine cessation program. The user may be presented with a slider button. The user may use the slider button to length or shorten the cessation program. For example, the user may be presented with a range of lengths, and the user may use the slider button to select a range from the range of lengths.

FIG. 16B depicts an example user interface for providing user feedback on CO level reduction information gathered and tracked throughout the program. The application may track one or more CO levels for a user. For example, the application may store a history of CO levels for the user that were measured over a length of time. The application may determine from the CO levels that the user has reduced their cigarette consumption. For example, at 1602, a user may be notified that their history of CO levels indicates that CO levels have been reduced from 21 ppm to 5 ppm. The user may also be notified that 5 ppm indicates that the user has a CO level of a non-smoker.

FIG. 16C depicts an example user interface for providing user feedback on user heart rate information gathered and tracked throughout the program. The application may track one or more HR measurements for a user. For example, the application may store a history of HR measurements taken from the user over a length of time. The application may determine from the HR measurements that the user has improved their health. For example, at 1606, a user may be notified that their resting HR has been reduced from 83 to 70 over the course of 12 weeks.

The user's smoking behavior or nicotine addiction may be determined based on real time feedback of biological indicators and/or behavioral support elements. The feedback information may be used to adapt the user's smoking cessation plan during a quit attempt. For example, biomarkers, which may include physiological and phycological biomarkers, may use to suggest actions and/or behavioral modifications that may promote a benefit.

Figures 17A, 17B, 17C:
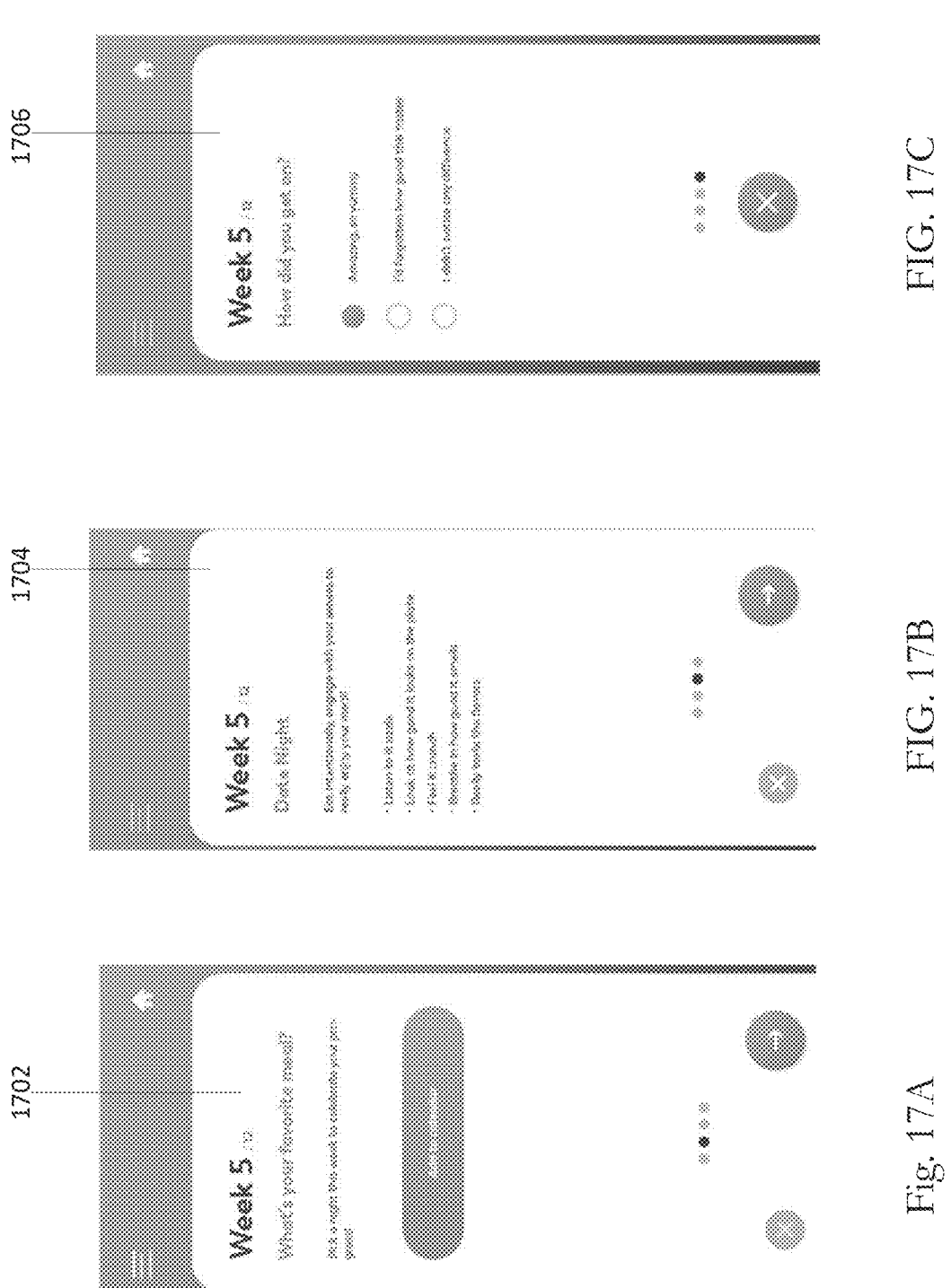
FIGS. 17A-C depict example user interfaces for suggesting an action to experience the benefits of the nicotine cessation journey.

FIGS. 17A-C depict example user interface(s) for suggesting an action to experience a benefits of the nicotine cessation journey. The timing for offering a suggestion may be determined based on biological indicators. FIG. 17A depicts an example user interface that may suggest an action for a user to take that may be based on one or more biomarkers. For example, one or more biomarkers may be used to determine that a user may have a craving around dinner time. The one or more biomarkers may indicate that the user may have had a positive progression associated with the cessation program. For example. The one or more biomarkers may indicate that the user may have reduced nicotine consumption (e.g., reduced smoking or NRT). At 1702, the user interface may suggest that the user celebrate their progress with a meal. For example, the user interface may ask the user what their favorite meal may be and may suggest that the user schedule that meal on their calendar. FIG. 17B shows an example user interface that a behavioral modification associated with a selected user action. For example, at 1704, the user may have scheduled a meal and the user interface may suggest that the user eat intentionally. This may be done, for example, to prevent a nicotine craving that may occur around the time of the meal. FIG. 17C shows an example user interface that may seek feedback from a user regarding an action and/or a behavioral modification. For example, at 1706, the user interface may ask the user how the scheduled meal went. The user may respond. The use response may indicate that the user engaged with the action. The response may indicate that the user made the behavioral modification. The response may indicate that a likelihood that the action prevented a nicotine craving and/or lessened the likelihood of a nicotine craving.

Figure 18:
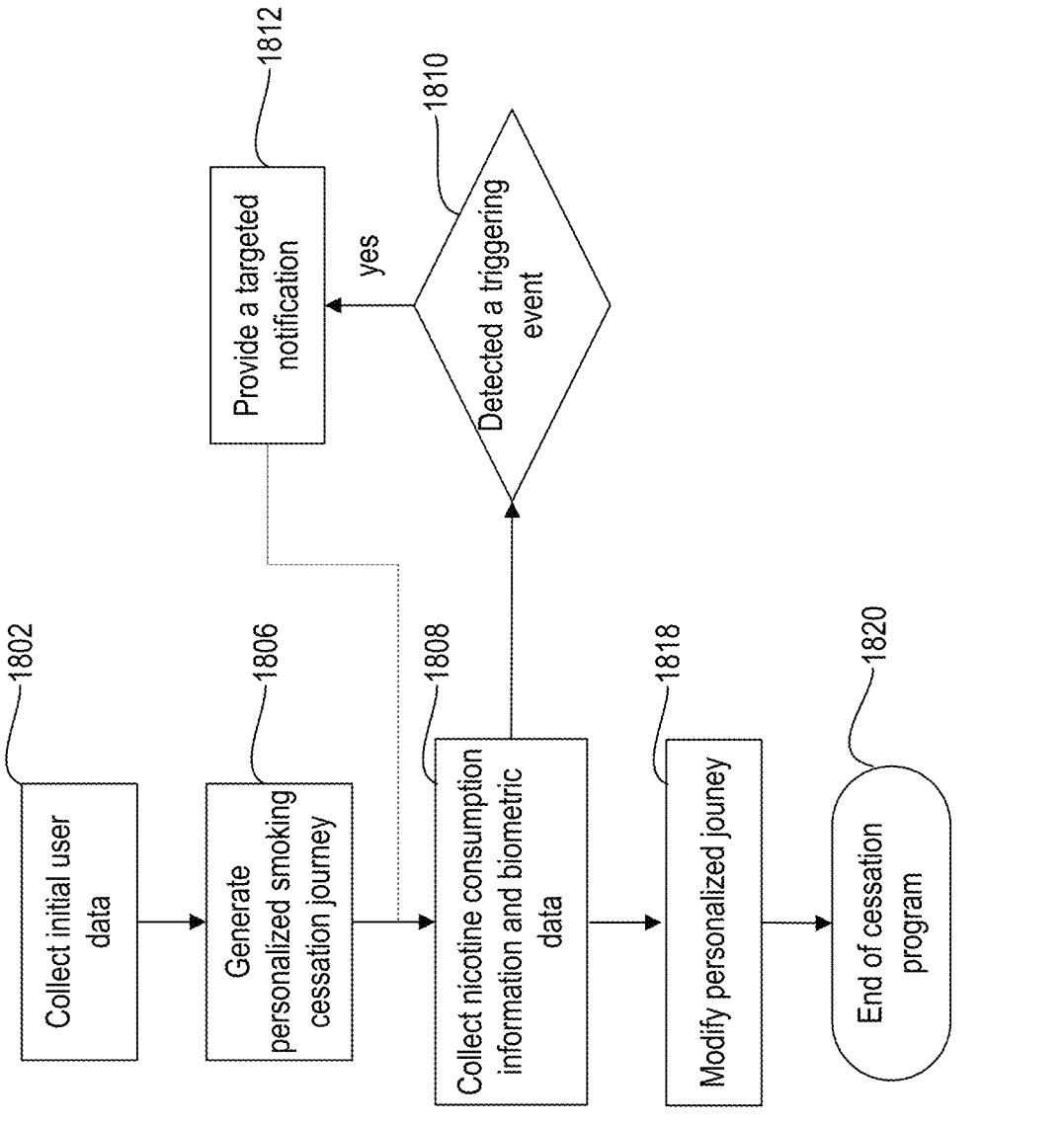
FIG. 18 depicts an example flowchart for providing a personalized nicotine/smoking cessation journey.

FIG. 18 depicts an example flowchart for providing a personalized nicotine cessation journey. As shown, at the beginning of the personalized nicotine cessation journey, initial user data may be collected at 1802. At 1806, a personalized smoke cessation journey may be generated based at least in part on the collected user data. At 1808, additional data, such as nicotine consumption information and user's biometric data may be collected as the journey progresses. At 1810, a triggering event may be detected, and at 1812, a targeted notification may be provided. For example, a potential craving may be detected and, a suggestion to use NRT may be provided. For example, a potential cigarette smoking may be detected based on the collected user CO level, and a confirmation of smoke may be requested. At 1818, the personalized journey may be modified based on the collected up-to-date user data. For example, the journey length may be shortened or prolonged. Weekly targets and/or daily targets may be updated. The type of behavioral suggestions may be refined based on the user's response. At 1820, the smoking cessation program may end. The initial user data and the collected data referred to in FIG. 18 may include various data received or obtained from various data sources described herein.

Figure 19:
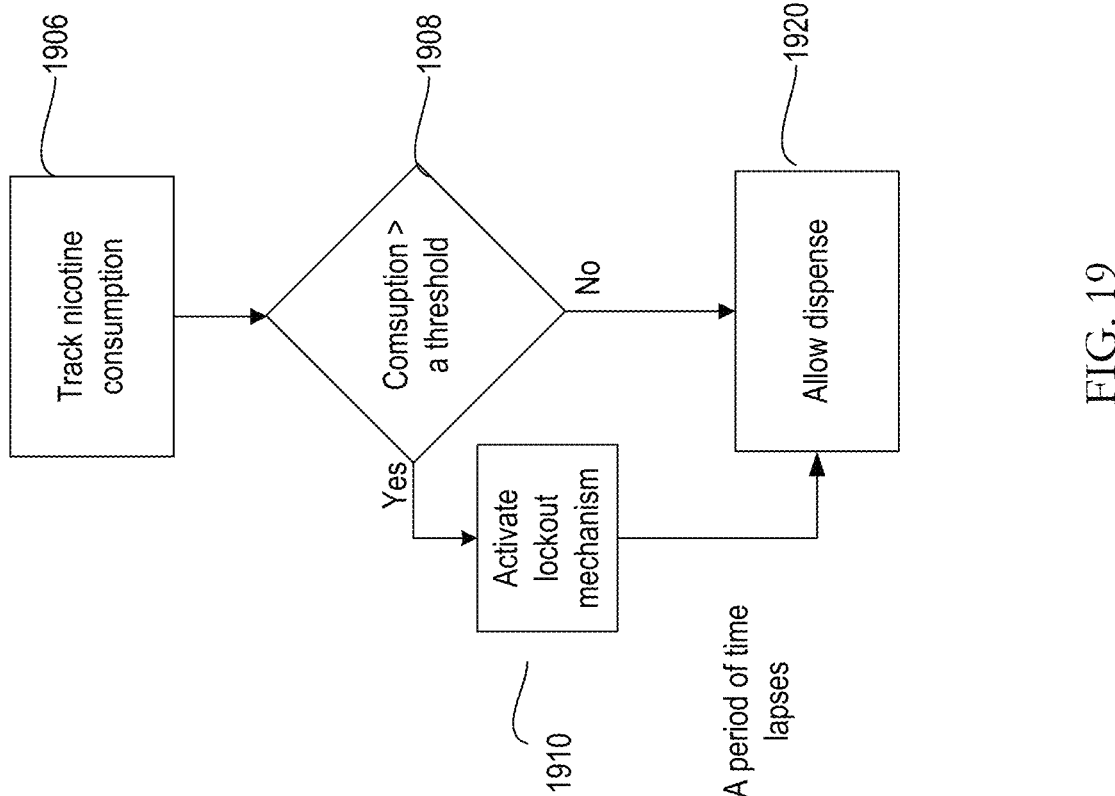
FIG. 19 depicts an example flowchart for controlling the lockout mechanism.

FIG. 19 depicts an example flowchart for controlling the lockout mechanism. At 1906, nicotine consumption may be tracked, for example using techniques described herein. Nicotine consumption data may be determined based on the nicotine concentration of the nicotine formulation in the NRT device, the number of full actuations, partial actuations of the dispenser and associated actuation time, and/or cigarette/tobacco consumption data logged by the user. At 1908, the nicotine consumption may be compared to a threshold. At 1910, a lockout mechanism may be activated, when determining that the consumption exceeds the threshold. Nicotine consumption threshold may be associated with a period time, such as 2 mg within half an hour, 4 mg within an hour, 64 mg within 24 hours, or the like. Nicotine consumption amount may be reset after a period of idle time during which the NRT device has not dispensed any nicotine formulation. For example, after the NRT device sitting idle for 4 hours, the nicotine consumption amount for comparing against the 24-hour consumption threshold may be reset to 0. The determination of whether nicotine consumption has exceeded a threshold may be performed at the NRT device and/or at another device such as a mobile phone, a smart watch, a tablet, a cloud computing function or the like. For example, a signal may be sent to the NRT device to instruct the NRT device to active the lockout mechanism. The lockout mechanism may be deactivated when a period of time lapses. For example, the lockout mechanism may be deactivated after half an hour, one hour, two hours or the like. If the consumption does not exceed the threshold, the NRT device may be allowed to dispense the nicotine formulation at 1920.

Figure 20:
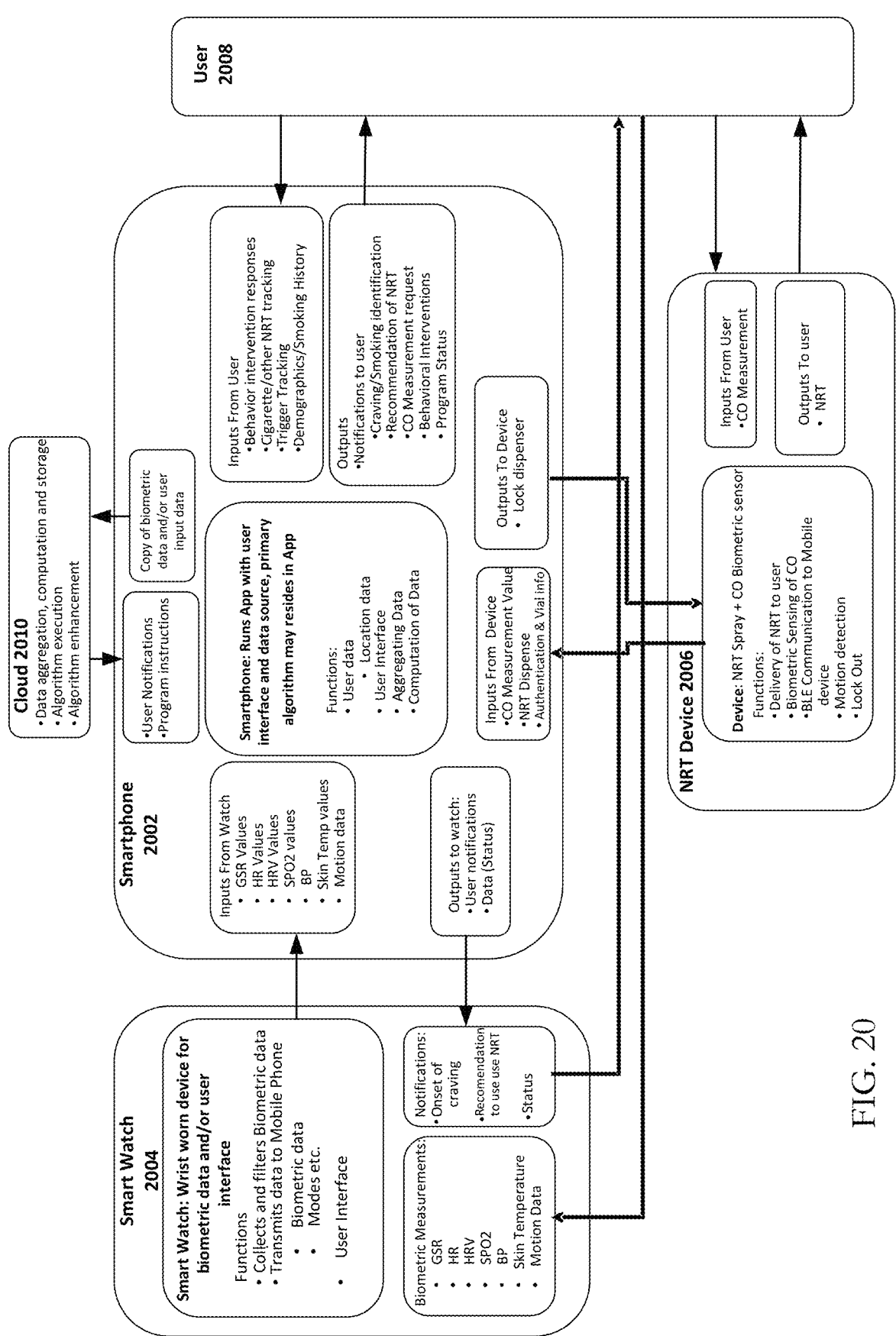
FIG. 20 depicts an example NRT system.

FIG. 20 depicts an example NRT system. As shown, the example NRT system may include smartphone 2002, a smart watch 2004, NRT device 2006, and cloud 2010. User 2008 may interact with the NRT system.

The NRT device 2006 may receive instructions from the smartphone 2002 to lock the dispenser. The NRT device 2006 may send data, such as CO measurements, NRT dispense data, vial authentication information, and/or vial information, to the smartphone 2002. As described herein, the NRT device 2006 may include an NRT spray and a biometric sensor such as a CO sensor. The NRT device 2006 may include one of more functions including, delivering NRT to user, performing biometric sensing of CO, performing motion detection, locking the dispenser, and communicating to other device(s), for example, via BLE.

As shown in FIG. 20, the smartphone 2002 may run an app having a user interface. The smartphone 2002, via the app, may perform one or more functions including, tracking user data such as location data, providing a user interface, aggregating data, and computing data. The smartphone 2002 may, for example, via the user interface in the app, receive various indications from a user, such as user 2008. User indications may include one or more of behavior intervention responses, cigarette, NRT, or other nicotine product consumption tracking information, trigger tracking information, user demographics, user smoking history, and/or the like. The smartphone 2002 may receive data from and/or send data to smart watch 2004. For example, the app may, via smartphone 2002, receive data from the smart watch 2004 including GSR values, HR values, HRV values, peripheral oxygen saturation (e.g., SPO2) values, blood pressure, skin temp values, and/or motion data. The smartphone 2002 may send user notifications and program status to the smart watch 2004 for displaying on the smart watch 2004.

The smart phone 2002 may, for example, via the user interface in the app, provider user notifications. User notifications may include, but not limited to, indicating potential craving, indicating potential smoking activities, recommending NRT, requesting CO measurement, providing behavioral intervention recommendations, and providing program status/health improvements.

As shown, cloud-based control functions may be used. For example, the smart phone 2002 may send biometric data and user input data to the cloud 2010 (e.g., one or more cloud servers, which may be computing resource 212). The cloud 2010 may perform data aggregation such as aggregating data from a community of users, perform data computation, and store various data. The cloud 2010 may enhance algorithm based on the received, aggregated, and/or computed data. The cloud 2010 may send user notifications and program instructions to the smartphone 2002.

As shown, the NRT system may include the smart watch 2004 that may send various data to the smartphone 2002. The smart watch 2004 may be or may include a wrist worn device for sensing biometric data and/or providing a user interface. The smart watch 2004 may collect and filter user biometric data. The smart watch 2004 may perform biometric measurements such as GSR values, HR values, HRV values, SPO2 values, blood pressure, skin temp values, and/or motion data. The smart watch 2004 may send data such as biometric data and mode information to other device(s), such as the mobile phone, and the NRT device 2006. The smart watch may be configured to provide notifications such as notification of onset of craving, recommendation to use NRT, and/or providing program status/health improvements.

FIG. 21 depicts an example 12-week NRT journey that may be customized based on various data sources such as senor feedback. Success rate of quitting addition may be increased through various feedback and personalization. In examples, a user's biometric data may be collected during a control period, such as a period time prior to the program (e.g., one week prior to starting the program). A personalized program may be generated based on the biometric data collected during the control period and/or other behavior inputs from the user. The recommended program may be updated via a continuous update loop such that the program may timely address user needs, such as slipups or exceeding expected progress.

As shown in FIG. 21, the program may include cigarette reduction targets that may be modified based on the user's data. The program may include NRT usage recommendations, such as NRT recommendations (for example, during an initial portion of the program) and NRT reduction targets (for example, during a later portion of the program), which may be modified based on user data (such as sensor feedback). The program may include NRT usage recommendations 2120, which may be provided and/or modified on a weekly basis. The program may include cigarette usage recommendations 2128, which may be provided and/or modified on weekly basis.

At 2102, the cessation program may include a recommendation for a time period before the program may begin. This may be done, for example, to allow a user to become familiar with the cessation application and/or an NRT device. The time period may be three weeks before the cessation of cigarettes may be being. The recommendation at 2102 may be allow for the user to become familiar with the program, and may recommend no reduction in cigarettes and/or NRT.

At 2104, the cessation program may include a recommendation for week 1. Week 1 may recommend a 50% cigarette reduction and a 25% NRT usage. For example, week 1 may recommend that a user reduce a baseline cigarette consumption by 50% and increase a baseline nicotine formulation consumption by 25%. The baseline cigarette consumption and/or baseline nicotine formulation consumption may be based on a prior time period, a current time period, and/or a combination thereof.

At 2106, the cessation program may include a recommendation for week 2. Week 2 may recommend a 25% cigarette reduction and a 50% NRT usage. For example, week 2 may recommend that a user reduce a baseline cigarette consumption by 25% and increase a baseline nicotine formulation consumption by 50%. The baseline cigarette consumption and/or baseline nicotine formulation consumption may be based on a prior time period, a current time period, and/or a combination thereof.

At 2108, the cessation program may include a recommendation for week 3. Week 3 may recommend a 75% cigarette reduction and a 75% NRT usage. For example, week 2 may recommend that a user reduce a baseline cigarette consumption by 75% and increase a baseline nicotine formulation consumption by 75%. The baseline cigarette consumption and/or baseline nicotine formulation consumption may be based on a prior time period, a current time period, and/or a combination thereof.

At 2110, the cessation program may include a recommendation for week 4. Week 4 may recommend a 100% cigarette reduction (e.g., stop smoking) and a 100% NRT usage. For example, week 4 may recommend that a user reduce a baseline cigarette consumption by 100% and increase a baseline nicotine formulation consumption by 100%. The baseline cigarette consumption and/or baseline nicotine formulation consumption may be based on a prior time period, a current time period, and/or a combination thereof.

At 2112, the cessation program may include a recommendation for week 5. Week 5 may recommend a 0% cigarette usage (e.g., user may no longer smoke) and a 100% NRT usage (e.g., maintain using nicotine formulation). For example, week 5 may recommend that a user avoid smoking and continue to consume nicotine formulation.

At 2114, the cessation program may include a recommendation for week 6. Week 6 may recommend a 0% cigarette usage (e.g., user may no longer smoke) and a 100% NRT usage (e.g., maintain using nicotine formulation). For example, week 6 may recommend that a user avoid smoking and continue to consume nicotine formulation.

At 2116, the cessation program may include a recommendation for week 7. Week 7 may recommend a 0% cigarette usage (e.g., user may no longer smoke) and a 100% NRT usage (e.g., maintain using nicotine formulation). For example, week 7 may recommend that a user avoid smoking and continue to consume nicotine formulation.

At 2118, the cessation program may include a recommendation for week 8. For example, week 8 may recommend a 0% cigarette usage (e.g., user may no longer smoke) and a 100% NRT usage (e.g., maintain using nicotine formulation). For example, week 8 may recommend that a user avoid smoking and continue to consume nicotine formulation.

At 2120, the cessation program may include a recommendation for week 9. Week 9 may recommend a 0% cigarette usage (e.g., user may no longer smoke) and a 25% NRT reduction (e.g., reduce nicotine formulation consumption). For example, week 9 may recommend a user avoid smoking and reduce a baseline nicotine formulation consumption by 25%. The baseline nicotine formulation consumption may be based on a prior time period, a current time period, and/or a combination thereof.

At 2122, the cessation program may include a recommendation for week 10. Week 10 may recommend a 0% cigarette usage (e.g., user may no longer smoke) and a 50% NRT reduction (e.g., reduce nicotine formulation consumption). For example, week 10 may recommend a user avoid smoking and reduce a baseline nicotine formulation consumption by 50%. The baseline nicotine formulation consumption may be based on a prior time period, a current time period, and/or a combination thereof.

At 2124, the cessation program may include a recommendation for week 11. Week 11 may recommend a 0% cigarette usage (e.g., user may no longer smoke) and a 75% NRT reduction (e.g., reduce nicotine formulation consumption). For example, week 11 may recommend a user avoid smoking and reduce a baseline nicotine formulation consumption by 75%. The baseline nicotine formulation consumption may be based on a prior time period, a current time period, and/or a combination thereof.

At 2126, the cessation program may include a recommendation for week 12. Week 12 may recommend a 0% cigarette usage (e.g., user may no longer smoke) and a 100% NRT reduction (e.g., user may no longer consume nicotine formulation). For example, week 12 may recommend a user avoid smoking and avoid nicotine formulation consumption.

The 12-week NRT journey may also be customized for smokeless tobacco users, heated or non-combusted tobacco users, electronic cigarette users and/or vaping product users. For example, the 12-week NRT journey may be customized for nicotine consumption that may comprise nicotine from a cigarette, tobacco product, electronic cigarette with nicotine, and/or an alternate source, such as a skin patch, chewing gum, nasal spray, inhaler, lozenge/tablet, oral spray, and the like.

Various data may be collected prior to the user joining the example smoking cessation program and periodically during the program. Control data may be collected, received and/or stored prior to or at the beginning of the program. Such control data may include one or more of the biometric measurements as described herein. For example, control data may include control HR, HRV, CO level, and/or the like.

The user may experience CO level reduction. The dropout risk of the user may be determined based on the CO level tracked over time. Whether the user has smoked a cigarette may be tracked. For example, if the user's tracked CO level is not reduced as expected or the user's CO level increases, potential dropout may be identified. The program may be updated to address the potential dropout.

Health improvements, in terms of HRV, HR, CO level and blood pressure, may be determined and indicated to the user, for example, to encourage the user to stay with the program.

Behavioral support data may be collected at the beginning of the program and tracked throughout the program for personalizing the program. For example, data related to motivation, willpower, and addiction may be entered by the user. The easiest cigarettes to eliminate may be identified (e.g., by the user, and/or by the program based on user data) via the app. Craving coping strategies may be entered by the user. Craving coping strategies may be generated and presented to the user. For example, craving coping strategies may be generated based on the behavioral support data of the user tracked overtime and/or behavioral support data of other users. Potential withdrawal may be predicted based on the behavioral support data, and corresponding behavioral change recommendations may be indicated to the user.

As described herein, cigarette and/or tobacco and/or electronic cigarette and/or vaping product and/or NRT consumption may be tracked, along with trigger(s), location, and timing. Location tracking data may be used to determine location-based behavior support. Nicotine or cigarette craving may be tracked during the program. NRT dropout risk may be determined based on whether the user is using NRT more frequently than recommended. The program may be updated to address the potential dropout.

Figure 22:
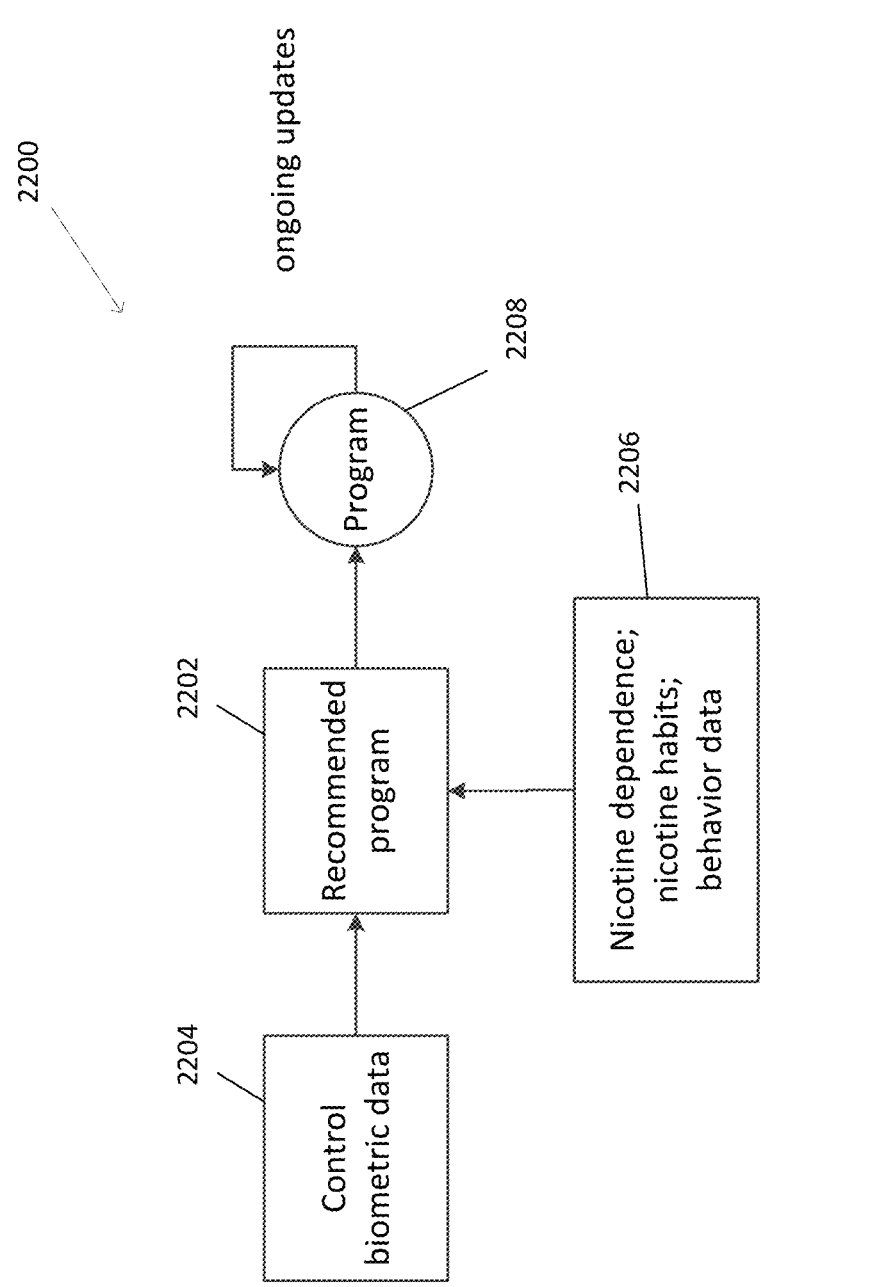
FIG. 22 depicts an example flowchart for updating the NRT program.

FIG. 22 depicts an example flowchart for updating the NRT program. As shown, a recommended program 2202 may be generated by a system 2200 based on control biometric data 2204 and nicotine dependence, nicotine habits, and/or behavior data 2206. The recommended program 2202 may be performed by the system 2200 as an NRT program 2208. The NRT program 2208 may be updated continuously based on program adaptation data and detected user activity, such as smoking slipup.

As the user progresses through each stage of the NRT program 2208, the system 2200 may use the control biometric data 2204 and the nicotine dependence, nicotine habits, and/or behavior data 2206 to determine if the user is on track, behind expectation, or ahead of expectation. If the user is on track, the system 2200 may not recommend any change to the initially recommended program 2202. If the user is behind expectation, the system 2200 may determine whether the setback is due to a single occurrence or multiple occurrences of smoking acts. If the user is behind expectation due to occurrence of single smoking act, then a behavioral intervention (e.g., a coping technique) may be suggested to help the user get back on track. If the user is behind expectation because of multiple occurrences of smoking acts (e.g., a behavioral trend is identified), the system 2200 may recommend extending the initially recommended program 2202 to give the user more time to get back on track. If the user is ahead of expectation, the system 2200 may recommend truncating the initially recommended program 2202.

Figures 23A, 23B:
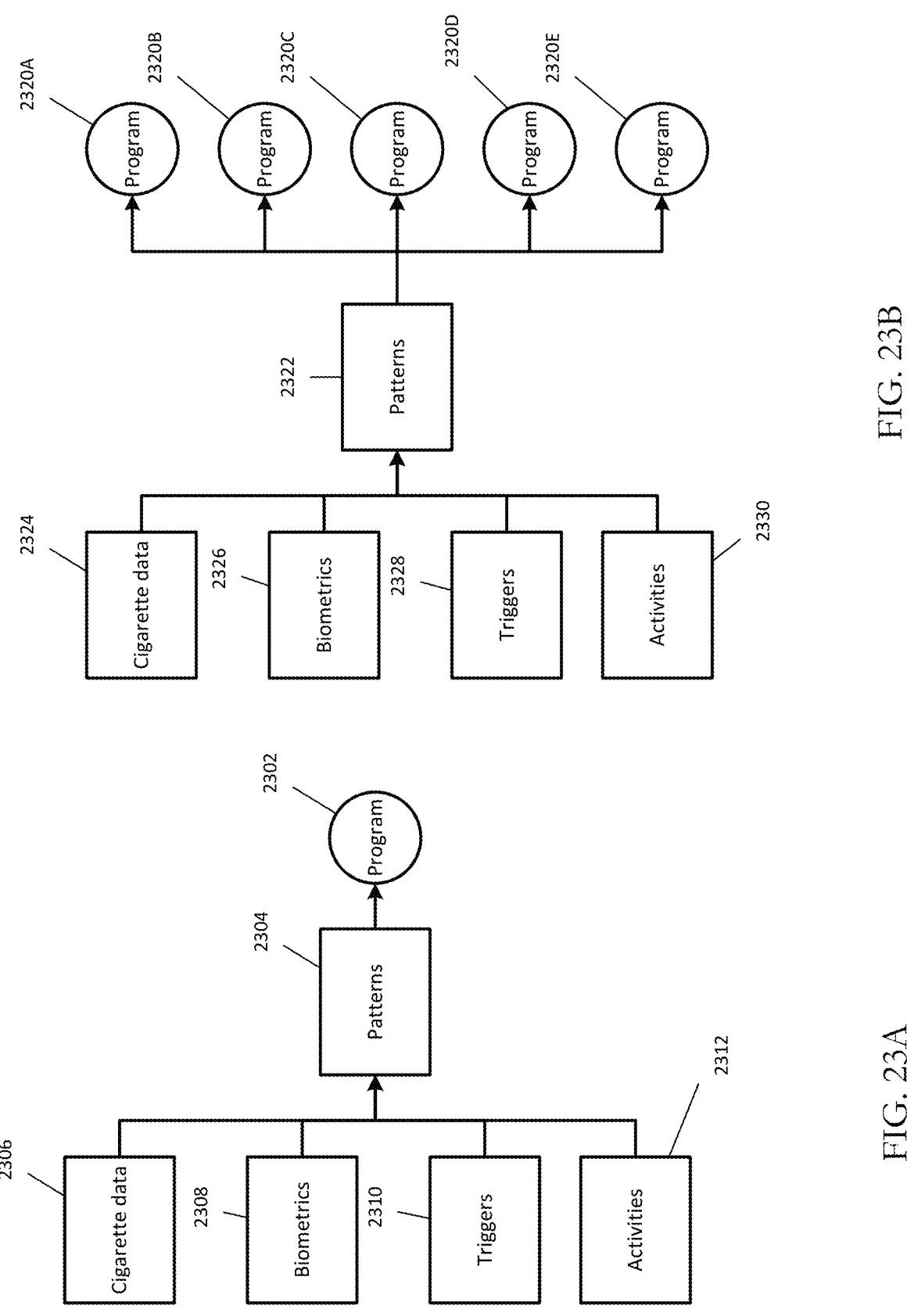
FIG. 23A depicts an example flowchart for pattern identification and updating a user's personalized NRT program based on the identified patterns.
FIG. 23B depicts an example flowchart for pattern identification and updating NRT programs for multiple users based on the identified patterns.

FIG. 23A depicts an example flowchart for pattern identification and updating a user's personalized NRT program based on the identified patterns. As shown, patterns 2304 may be used to modify a user's personalized NRT program 2302. The patterns 2304 may be identified by analyzing (e.g., continuously analyzing) a variety of data. The variety of data may include cigarette data 2306, biometrics 2308, triggers 2310, and/or activities 2312.

FIG. 23B depicts an example flowchart for pattern identification and updating NRT programs for multiple users based on the identified patterns. As shown, patterns 2322 may be used to modify users' personalized NRT programs 2320A-2320E. The patterns 2322 may be identified by analyzing (e.g., continuously analyzing) a variety of data. The variety of data may include cigarette data 2324, biometrics 2326, triggers 2328, and activity data 2330 from multiple users (e.g., users in an NRT community, users having similar demographic information). The patterns 2322 may be used to develop personalized and modify NRT programs 2320A-2320E for multiple users. For example, the patterns 2322 may be used to generate recommendations for replacing which type of cigarettes with NRT. The patterns 2322 may be used to generate recommendations for which NRT to start with in an NRT reduction journey.

Figure 24:
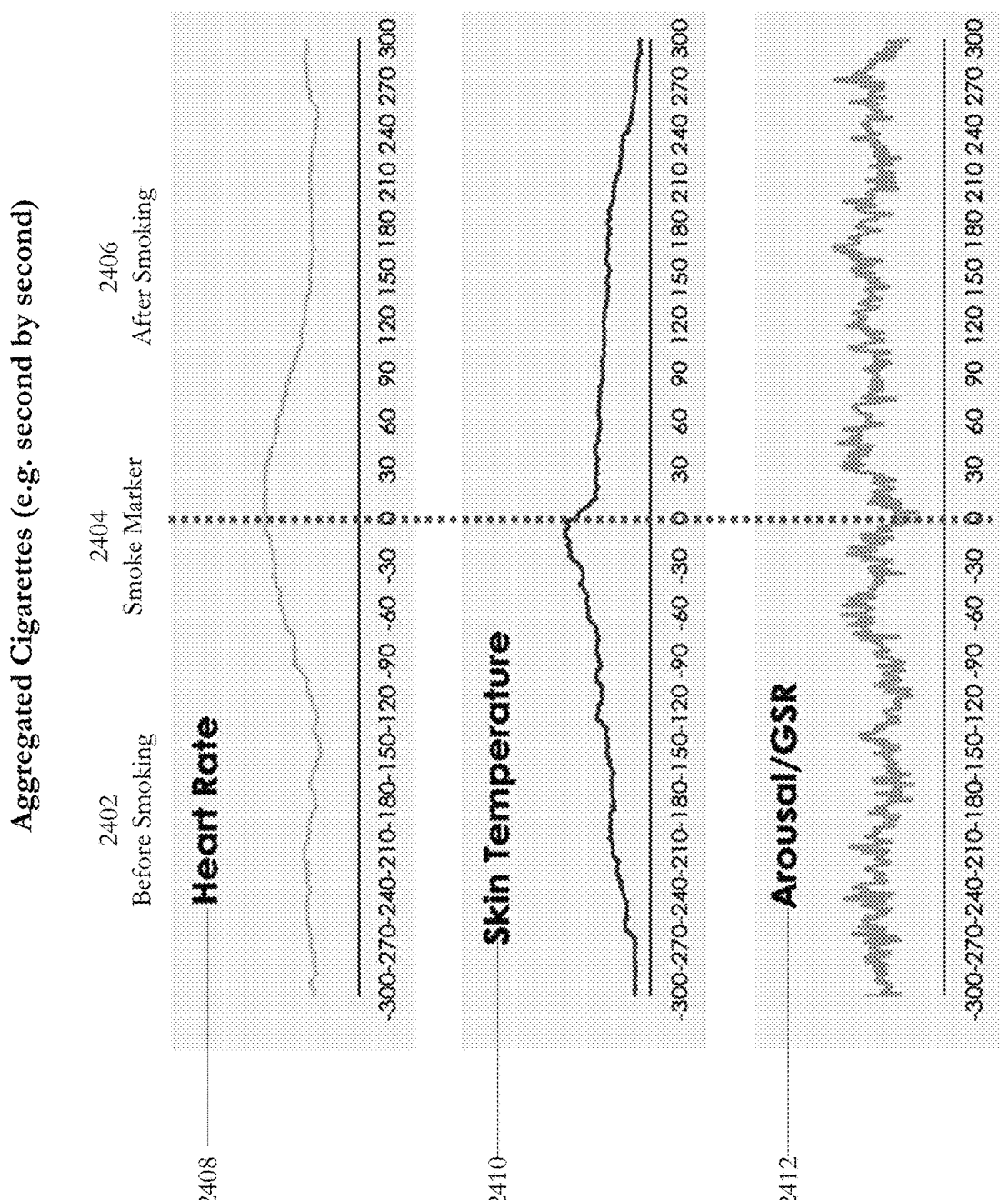
FIG. 24 depicts examples of biometrics affected by smoking.

FIG. 24 depicts examples of biometrics affected by smoking. As shown, at 2402, the biometrics may change before the smoke marker 2404. At 2406, the biometrics may change after the smoke marker 2404. The time in relation to the smoke marker 2404 is shown in seconds in FIG. 24. Examples of biometrics that may be affected are heart rate 2408, skin temperature 2410, and arousal/GSR 2412. For example, the heart rate 2408 may begin to increase for about two and a half minutes (−150 seconds as shown in FIG. 24) before users start smoking at 2402 (before the smoke marker 2404) and may decrease for about two and half minutes (150 seconds as shown in FIG. 24) after users smart smoking at 2406 (after the smoke marker 2404). For example, skin temperature 2410 may increase (e.g., steadily increase) at 2402 before users start smoking (before the smoke marker 2404) and may decrease once they begin smoking at the smoke marker 2404 and after smoking at 2406. The increase in skin temperature 2410 before the smoke marker 2404 may occur despite that users may often (e.g., most often) smoke outside. For example, the arousal/GSR 2412 may increase between two minutes and one minute before the smoke marker 2404. The arousal/GSR 2412 may dip (e.g., immediately dip) before the smoke marker 2404 and may increase (e.g., increase again) for about thirty seconds after the smoke marker 2404.

In examples, smoking cessation may have effects on blood pressure and heart rate variability in habitual smokers. As explained in in Minami et al. (Minami, Junichi, Toshihiko Ishimitsu, and Hiroaki Matsuoka. "Effects of smoking cessation on blood pressure and heart rate variability in habitual smokers." Hypertension 33.1 (1999): 586-590), ambulatory blood pressure, heart rate, and heart rate variability in 39 normotensive male habitual smokers with a mean age of about 33 years old were tested. The examples were randomized to start with one week nonsmoking and (e.g., and then) one week smoking with 19 smokers and randomized to start with one week smoking and (e.g., and then) one week nonsmoking with 23 smokers. In these examples, a cuff-oscillometric device measured blood every 30 minutes on the last day of each period and measured the R-R interval of the ECG for five-minute block on the last day of each period. The results indicated that smokers have a higher heart blood pressure (e.g., systolic: 3.5 mmHg, diastolic: 1.9 mmHg but only during daytime), a higher heart rate (e.g., 7.3 beats/min), a lower LF, a lower HF, and a higher LF/HV ratio (e.g., but only during daytime).

In the examples, in the 24 hour trends of BP and HR during the smoking and nonsmoking periods and the average number of cigarettes smoked per hour in the smoking period, the daylight BP was significantly lower in the nonsmoking period than in the smoking period, whereas the nighttime BP did not differ (e.g., differ significantly) between the two periods. In the examples, the daytime and nighttime HR values were significantly lower in the nonsmoking period than in the smoking period. In the examples, in the 24 hour trends of the LF component, the HF component, and the LF/HF ratio during the smoking and nonsmoking periods and the average number of cigarettes smoked per hour in the smoking period, the LF and HF components were both higher (e.g., significantly higher) in the nonsmoking period than in the smoking period in both the daytime and nighttime. In the examples, in the 24 hour trends of the LF/HF ratio, the daytime LF/HF ratio was significantly lower in the nonsmoking period than in the smoking period, whereas the nighttime LF/HF ratio did not differ (e.g., differ significantly) between the two periods.

In examples, smoking cessation and nicotine patches may have effects on affect heart rate variability. As explained in Stein et al. (Stein, Phyllis K., Jeffrey N. Rottman, and Robert E. Kleiger. "Effect of 21 mg transdermal nicotine patches and smoking cessation on heart rate variability." The American journal of cardiology 77.9 (1996): 701-705), 54 male smokers with mean (SD) age of 43 (12) with a desire to quit smoking were given at least one pack/day and had at least one prior attempt to quit. 35 smokers used 21 mg patches for four to six weeks and 25 smokers ceased the use of patch for 4 weeks. In the results, as measured by the 24 h ECG during smoking cessation, smoking cessation decreased (e.g., significantly decreased) the heart rate and increased all 24 hour time and frequency domain indexes of heart rate variability. Part of the change may have occurred in the transition from smoking to the patch, and further changes may occur with cessation of patch use. In the results as measured four weeks after cessation of all nicotine use, the average heart rate remained higher, and heart rate variability remained lower than values reported for healthy, middle-aged adults.

In examples, smoking cessation may have effects on heart rate variability among long-term male smokers. As explained in Harte et al. (Harte, Christopher B., and Cindy M. Meston. "Effects of smoking cessation on heart rate variability among long-term male smokers." International journal of behavioral medicine 21.2 (2014): 302-309), 62 male smokers between 23-60 years old who smoked over 15 cigarettes/day over at least five years were enrolled in an eight-week nicotine transdermal patch treatment. There were 20 successful quitters and 42 unsuccessful quitters. Participates' heart rate variabilities were assessed at baseline (e.g., while smoking regularly), at mid-treatment (e.g., while using a high-dose patch), and a follow-up, four weeks after patch discontinuation using a three-channel ECG for four hours on-site. The 20 successful quitters compared to the 42 who were unsuccessful quitters displayed higher (e.g., significantly higher) SDNN, RMSSD, pNN50, LF, and HF at the follow-up, when they were both nicotine and smoke free.

In examples, smoking may have effects on resting heart rate, heart rates during exercise, and heart rate recovery in young adults. As explained in Papathanasiou et al. (Papathanasiou, George, et al. "Effects of smoking on heart rate at rest and during exercise, and on heart rate recovery, in young adults." Hellenic J Cardiol 54.3 (2013): 168-177), a sample of 298 adults between 20-29 years old with normal BMI and normotensive were tested. 79 female non-smokers, 60 female smokers, 86 male non-smokers, and 73 male smokers were tested. The smokers smoked at least 20 cigarettes/day for at least three years while the non-smokers never smoked. A 12-lead ECG was used for measuring heart rate and the maximal Bruce treadmill test was during to measure heart rates during, at peak, and after termination of exercise. In the results, the smokers had higher (e.g., significantly higher) resting heart rates than the non-smokers. Both female and male smokers showed a slower (e.g., significantly slower) HR increase during exercise. Female smokers failed to reach their age-predicted maximum HR by 6.0 bpm and males by 3.6 bpm. The actual maximum HR achieved (HRmax) was significantly lower for both female smokers (191.0 bpm vs.198.0 bpm) and male smokers (193.2 bpm vs.199.3 bpm), compared to non-smokers. Heart rate reserve was also lower (e.g., significantly lower) in female (114.6 bpm vs. 128.1 bpm) and male smokers (120.4 bpm vs. 133.0 bpm). During recovery, the HR decline was attenuated (e.g., significantly attenuated), but only in female smokers. Females had a higher resting HR and showed a higher HR response during sub-maximal exercise compared to males.

Figure 25:
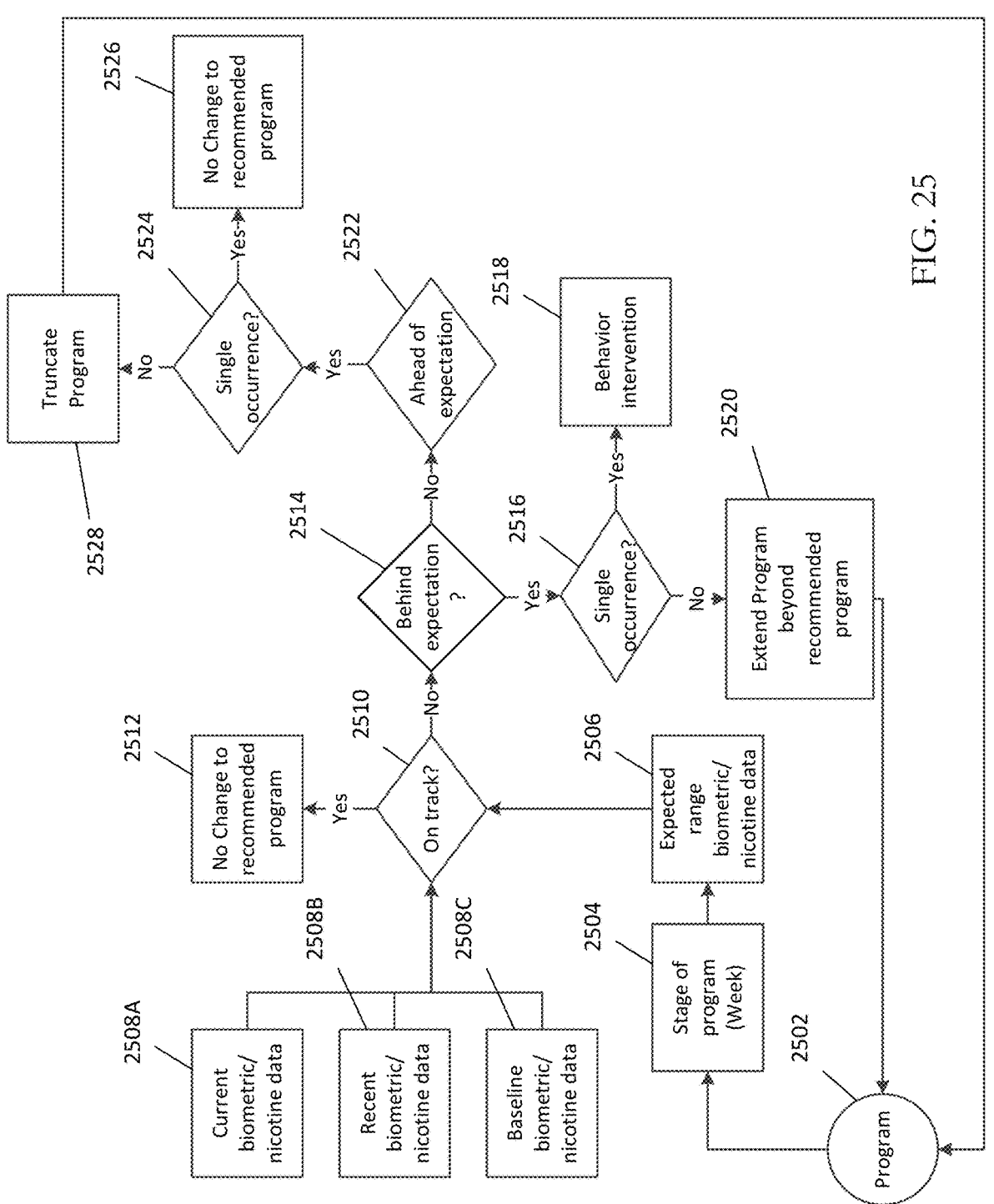
FIG. 25 depicts an example flowchart for modifying a personalized NRT program for a user based on various biometric data sources and nicotine data sources.

FIG. 25 depicts an example flowchart for modifying a personalized NRT program for a user based on various biometric data sources and nicotine data sources. An NRT program 2502 may be modified based on various factors. For example, at 2504, the stage of the NRT program 2502 may be determined. The stage of the program may be determined on a weekly basis. Based on the stage of the program, an expected range of biometric and/or nicotine data may be determined at 2506. For example, at some point of the cigarette smoking elimination program, the expected CO levels may be trending towards those of a non-smoker. For example, at some point of the cigarette smoking elimination program, the expected HR may be 10 bpm lower than the user's control HR. The expected range of biometric/nicotine may include data from one or more biometric data source(s), nicotine data source(s), and/or various combinations of HR, HRV, RHR, CO, respiration, NRT, cigarettes, other NRT consumption data.

As shown in FIG. 25, whether the user is on track with the program may be determined at 2510 by comparing current biometric and/or nicotine data at 2508A, recent biometric and/or nicotine data at 2508B, and baseline biometric and/or nicotine at 2508C with the expected biometric and/or nicotine data at 2506.

If it is determined that the user is on track at 2510, no change may be made to the NRT program 2502 at 2512. If it is determined that the user is not on track at 2510, whether the user's progress is behind expectation may be determined at 2514 or ahead of expectation may be determined at 2522. If the user is ahead of expectation at 2522, it may be determined whether the user has had a single occurrence of being ahead of expectation at 2524. If no at 2524, and it is determined that the user has been ahead of expectation multiple times (e.g., occurrence exceeding a threshold), the NRT program 2502 may be truncated at 2528. If yes at 2524 and it is determined that the user is ahead of expectation, but the occurrence may be a single or rare occurrence, no change may be made to the recommended program at 2526. If the user is behind expectation at 2514, it may be determined whether the user has had a single occurrence of being behind of expectation at 2516. If no at 2516 and it is determined that the user has been behind expectation multiple times (e.g., occurrence exceeding a threshold), the NRT program 2502 may be extended beyond the initial recommended program at 2520. If yes at 2516 and it is determined that the user is behind expectation, but the occurrence may be a single or rare occurrence, a behavior intervention recommendation may be indicated to the user at 2518. Behavior intervention could include providing (e.g., sending a text message, displaying a notification, or a like) a motivation for continuing with the NRT program 2502, prompting the user to start a breathing exercise, prompting the user to deploy one or more coping strategies and/or distraction techniques, prompting the user to review goal setting, etc.

Figure 26:
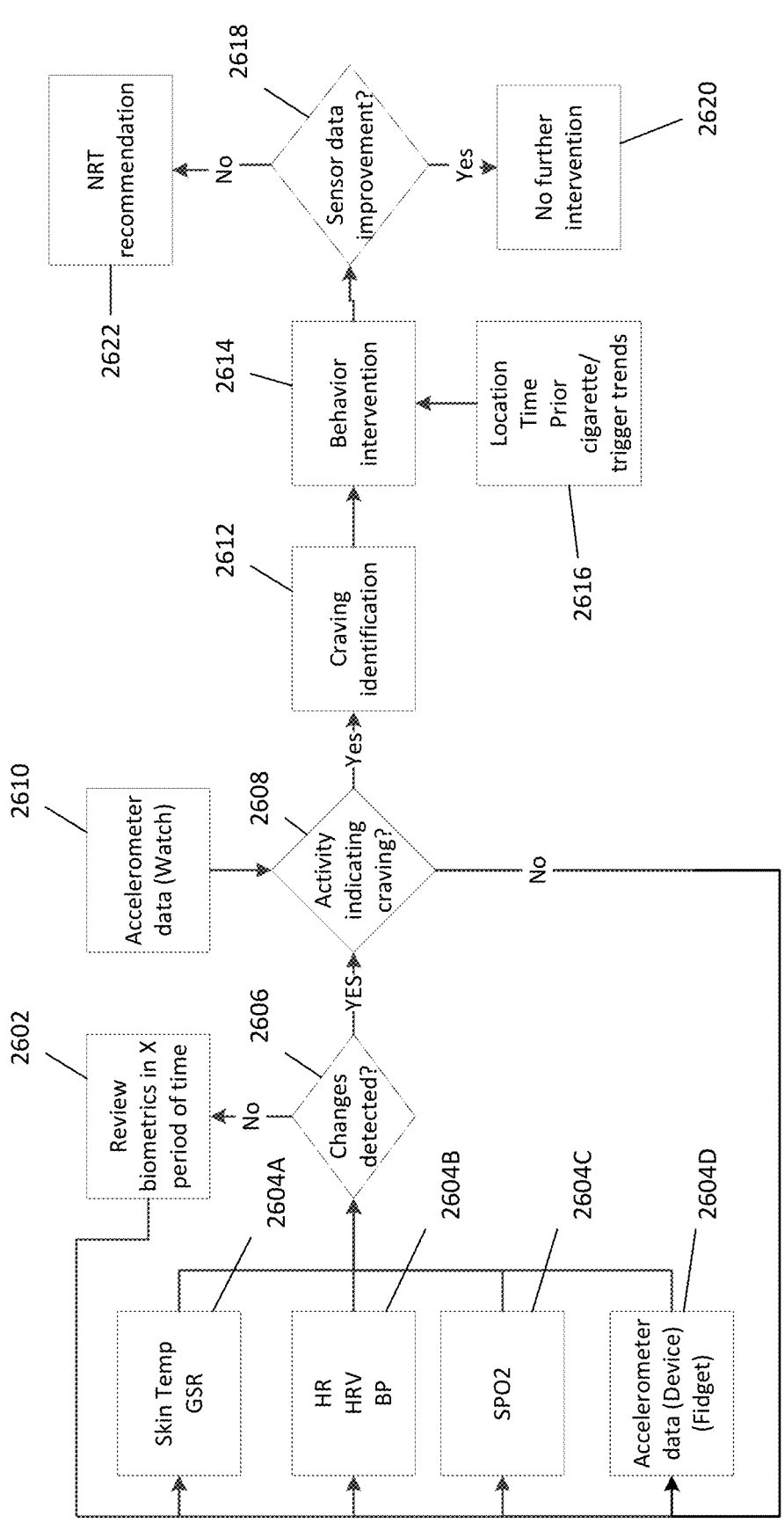
FIG. 26 depicts an example flowchart for craving identification. If nicotine/smoking craving is detected, use of NRT may be recommended to alleviate the craving.

FIG. 26 depicts an example flowchart for craving identification. If nicotine/smoking craving is detected, use of NRT may be recommended to alleviate the craving. If craving onset is correlated with certain locations or time of day, behavior intervention and/or NRT use recommendation may be provided to alleviate the craving (e.g., in advance of the craving). As a user progresses through each stage of their recommended program, the system may use a range of data to determine if or when the user experiences a nicotine/smoking craving. The types of data used may be collected biometric data. The collected biometric data may include GSR values and skin temp values at 2604A, HR values, HRV values, and blood pressure values at 2604B, SPO2 values at 2604C, and/or accelerometer data at 2604D such as fidgeting behavior (e.g., which may be associated with the NRT dispenser), that may be measured.

For example, at 2602 the biometric data may be reviewed periodically (e.g., weekly). Whether significant changes have occurred to the biometric data reviewed periodically may be determined at 2606. If no at 2606 and no changes are detected, the periodically reviewing biometric data monitoring may be continued at 2602. If yes at 2606 and it is determined that significant changes (e.g., one or more changes exceeding a threshold) are detected, whether the user's present or recent activity indicates a craving may be determined at 2608. For example, the user's present or recent activity may be determined based on user's accelerometer data (e.g., detected and received from a smart watch) at 2610. If the user's activity does not indicate a craving at 2608, the periodically reviewing of biometric data monitoring may be continued at 2602. If the user's activity indicates a craving at 2608, a craving identification is provided at 2612. If a craving identification is provided, a behavior intervention recommendation may be indicated to the user at 2614. Behavior intervention may be or may include providing (e.g., sending a text message, displaying a notification, or a like) a motivation for continuing with the NRT program, prompting the user to start a breathing exercise, prompting the user to deploy one or more coping strategies and/or distraction techniques, prompting the user to review goal setting, etc. The behavior intervention may be identified based on user's location, time, prior cigarette consumption, cigarette consumption trends, cigarette or NRT consumption triggers, and/or cigarette or NRT consumption trends at 2616. Whether the behavior intervention at 2614 leads to sensor data improvement may be determined at 2618. If yes at 2618 and the behavior intervention at 2614 leads to sensor data invention, no further intervention may be necessary at 2620. If no at 2618 and the behavior intervention does not lead to sensor data improvement, a suggestion to use NRT may be prompted at 2622.

Figure 27:
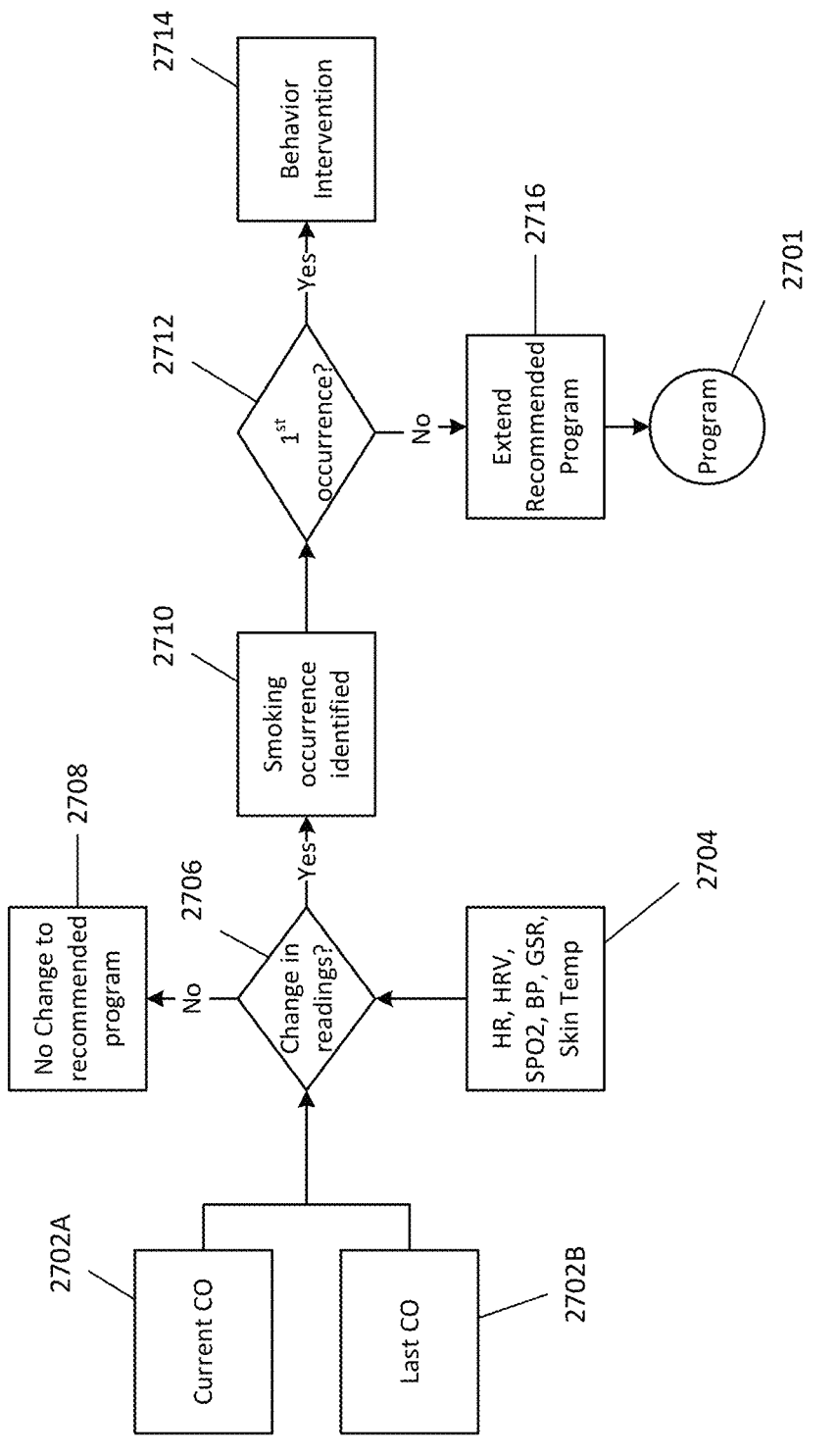
FIG. 27 depicts an example flowchart for behavior intervention.

FIG. 27 depicts an example flowchart for behavior intervention. As a user progresses through each stage of NRT program 2701, the system may use measured biometrics to determine if a cigarette smoking relapse has occurred. If cigarette smoking by the user is not detected, the system may make no changes to the recommended program. If cigarette smoking is detected, the system may further determine whether or not a single smoking act or multiple smoking acts occurred. If only a single smoking act occurred, a behavior intervention may be recommended to get the patient back on track. If multiple cigarette smoking acts occurred, then the system may recommend extension of the program to give the patient more time to get back on track.

As shown in FIG. 27, a current CO level 2702A and a previous CO level 2702B may be compared. Current and previous biometric data such as GSR values, skin temp values, HR values, HRV values, blood pressure values, SPO2 values may be compared at 2704. Whether there are changes detected between the current and previous readings may be determined at 2706. If no at 2706 and there are no changes in readings, or the changes are insignificant, the recommended program may remain the same at 2708. If yes at 2706 and a change in reading (e.g., a significant change such as one or more changes exceeding a threshold) is detected, a smoking occurrence may be identified at 2710. Whether the smoking occurrence is a first or a rare occurrence may be determined at 2712. If yes at 2712 and the detected smoking occurrence is a first occurrence or a rare occurrence, a behavior intervention recommendation, as described herein, may be indicated to the user at 2714. If no at 2712 and multiple or frequent smoking occurrences have been detected, the NRT program 2701 may be extended beyond the recommended program at 2716.

CO levels may be measured in ppm (COppm). 100+ COppm may indicate the heaviest smokers and are rare. 50-99 COppm may be seen in smokers consuming two or more packs a day. 36-49 COppm may be seen in smokers consuming a pack and a half a day. 20-35 COppm may be seen in smokers consuming a pack a day. 11-19 COppm may be seen in smokers just under a pack a day. 7-10 COppm may be seen in smokers who consume a small number of cigarettes per day but their level dependence may be high, particularly if they are getting their nicotine from multiple sources. 0-6 COppm may be in non-smokers and those who have recently stopped smoking. In examples, a cut-off level of 12 COppm may classify recent smokers from smokers having refrained from smoking during the past eight hours with a specificity of 94% and a sensitivity of 90% (see Sandberg, AnnSofi, et al. "Assessing recent smoking status by measuring exhaled carbon monoxide levels." *PLoS One* 6.12 (2011): e28864). In examples, in observational analyses among current smokers, 1 cigarette/day higher level of smoking heaviness was associated with a higher (0.21 bpm; 95% confidence interval 0.19; 0.24) resting heart rate and a higher (e.g., slightly higher) diastolic blood pressure (0.05 mm Hg; 95% confidence interval 0.02; 0.08) and systolic blood pressure (0.08 mm Hg; 95% confidence interval 0.03; 0.13) (see Linneberg, Allan, et al. "Effect of smoking on blood pressure and resting heart rate: a Mendelian random-ization meta-analysis in the CARTA consortium." Circula-tion: Cardiovascular Genetics 8.6 (2015): 832-841).

Figure 28:
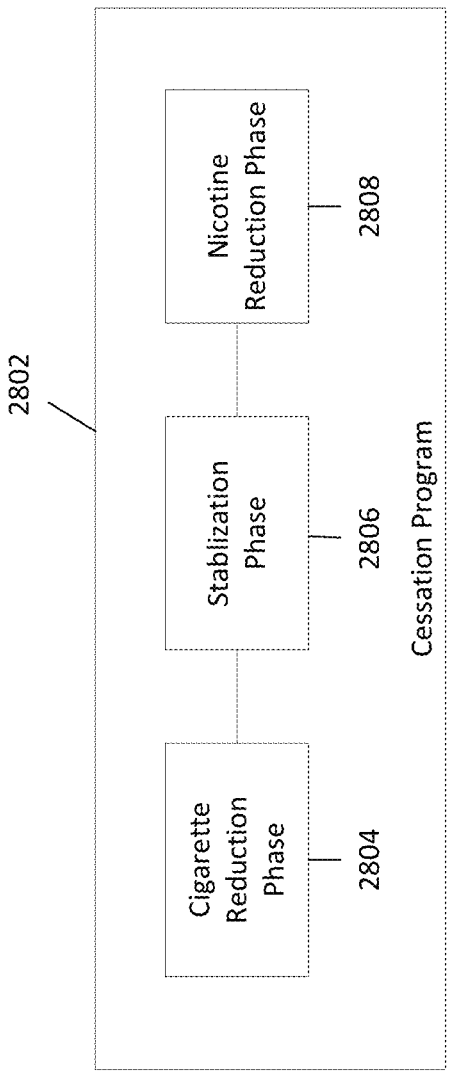
FIG. 28 depicts an example of a cessation program with multiple phases.

FIG. 28 depicts an example of a cessation program with multiple phases. As shown, a cessation program 2802 may include a cigarette reduction phase 2804, a stabilization phase 2806, and a nicotine reduction phase 2808. During the cigarette reduction phase 2804, cigarettes may be reduced or eliminated and replaced with NRT. The NRT may act as a replacement to cigarettes to provide (e.g., temporarily pro-vide) nicotine for users while reducing or eliminating ciga-rettes. In examples, the cigarette reduction phase 2804 may be the first phase within the cessation program 2802 (e.g., during weeks 1-4 of the cessation program 2802). In the cigarette reduction phase 2804, users may have a similar (e.g., somewhat similar) overall nicotine intake, but may reduce or eliminate cigarette use while instead using NRT instead for their nicotine intake. During the stabilization phase 2806, cigarettes may be entirely eliminated while the amount of NRT stays the same or decreases. The stabiliza-tion phase 2806 may be the second phase within the cessa-tion program (e.g., during weeks 5-8 of the cessation pro-gram 2802). In the stabilization phase 2806, users may have a same amount of nicotine intake or a lower amount of nicotine intake while entirely eliminating cigarettes. Instead, users during the stabilization phase 2806 may rely entirely on NRT for their nicotine intake. During the NRT reduction phase 2808, the NRT use should be reduced or eliminated, reducing or eliminating the nicotine intake for users. The NRT reduction phase may be the third and final phase of the cessation program 2802 (e.g., during weeks 9-12 of the cessation program 2802). In the NRT reduction phase 2808, users should be on track to entirely eliminate their nicotine intake.

Each of the cigarette reduction phase 2804, the stabiliza-tion phase 2806, and the NRT reduction phase 2808 may be completed in succession. For example, the stabilization phase 2806 may not begin until the user completes the cigarette reduction phase 2804 and the NRT reduction phase 2808 may not begin until the user completes the stabilization phase 2806. Depending on the performance of the users, which may be measured by various biometrics as described in examples herein, each of the cigarette reduction phase 2804, the stabilization phase 2806, and the NRT reduction phase 2808 may be extended or truncated. Extension of a phase may mean extending the duration of the phase, reducing the amount of reduction of cigarettes and/or NRT in a phase, reducing the rate of reduction of cigarettes and/or NRT in a phase, and/or moving back a phase. Truncation of a phase may mean shortening the duration of the phase, increasing the amount of reduction of cigarettes and/or NRT in a phase, and/or increasing the rate of reduction of ciga-rettes and/or NRT in a phase.

Figure 29:
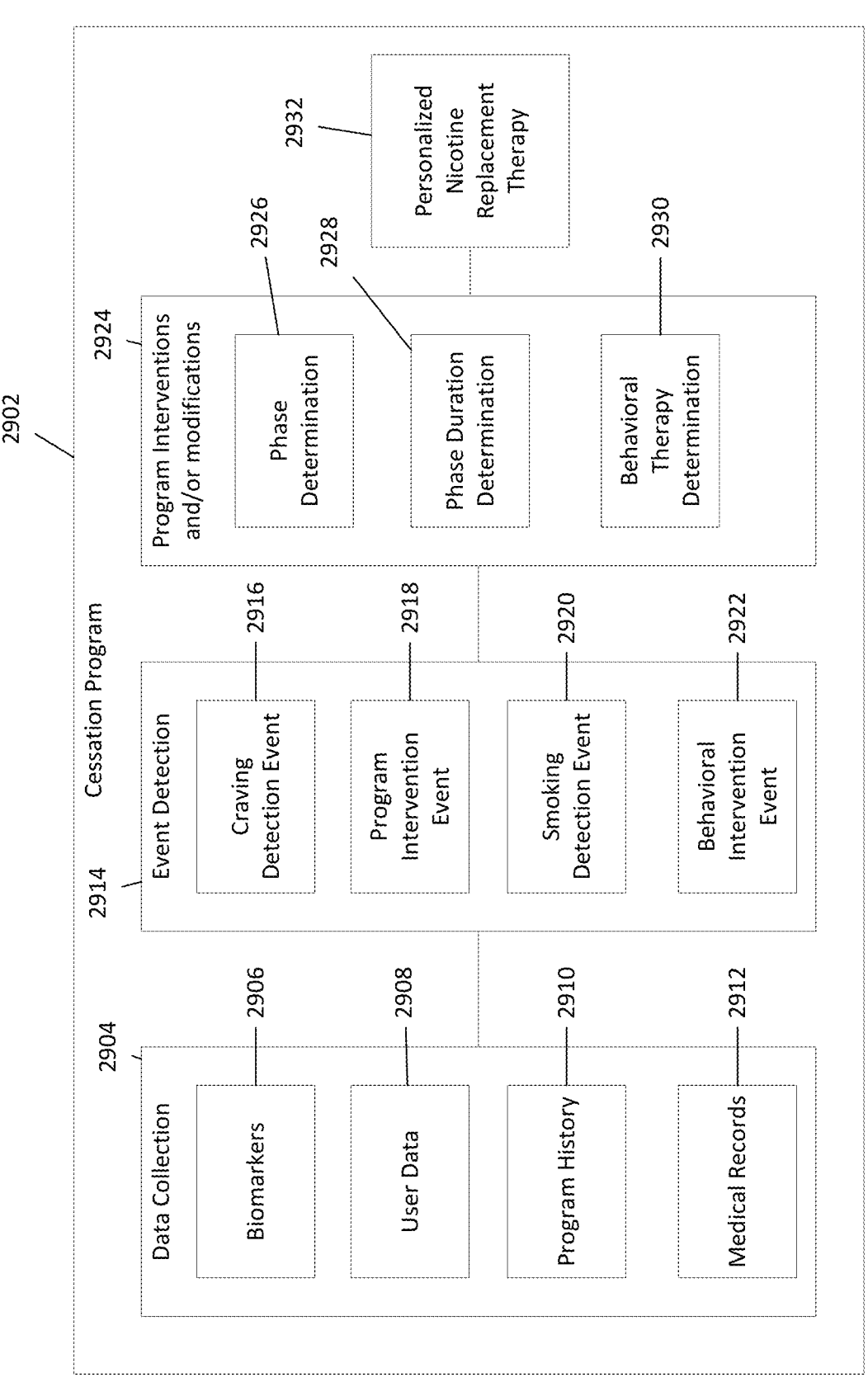
FIG. 29 depicts a block diagram of an example cessation program that generates a personalized nicotine replacement therapy.

FIG. 29 depicts a block diagram of an example cessation program that generates a personalized nicotine replacement therapy. A cessation program 2902 may utilize data collec-tion 2904, event detection 2914, and program interventions and/or modifications 2924 to generate a personalized nico-tine replacement therapy 2932. The data collection 2904 may be used to generate or trigger the event detection 2914. The event detection 2914 may be used to generate or trigger the program interventions and/or modifications 2924. The data collection 2904 may include biomarkers 2906, user data 2908, program history 2910, and medical records 2912. Biomarkers 2906 may include CO values, GSR values, skin temp values, HR values, HRV values, blood pressure values, SPO2 values, etc. User data 2908 may include personal data such as weight, height, BMI, history with smoking and/or other nicotine products, current and/or previous health con-ditions, and family history, etc. Program history 2910 may include any past data regarding the user using the cessation program 2902 and/or similar cessation programs. In examples, program history 2910 may include (e.g., may also include) any past data regarding users with similar personal characteristics, similar smoking histories, physical attri-butes, and/or health conditions. Medical records 2912 may include medical records relevant to smoking and nicotine replacement therapy.

The event detection 2914 may include a craving detection event 2916, a program intervention event 2918, a smoking detection event 2920, and a behavior intervention event 2922. The craving detection event 2916 may be determined by inputting biomarkers, which is described in more detail herein. The program intervention event 2918 may be deter-mined by inputting biomarkers and/or by determining the change in the amount of cigarettes used, the amount of NRT used, and the amount of carbon monoxide detected, which is described in more detail herein. The smoking detection event 2920 may be determined by biomarkers and/or by the amount of carbon monoxide detected, which is described in more detail herein. The behavior intervention event 2922 may be determined by biomarkers which may prompt the user to deploy one or more coping strategies and/or distrac-tion techniques or may prompt the user to review goal settings, etc.

Program interventions and/or modifications 2924 may include a phase determination 2926, a phase duration deter-mination 2928, and a behavioral therapy determination 2930. In examples, the phase determination 2926 may use the data collection 2904 and the event detection 2914 to determine whether a user is in the correct phase of the cessation program 2902. If yes, then the user may continue to follow the recommended cessation program. If no, then the user may move back a phase within the cessation program 2902 or move forward a phase within the cessation program 2902. In examples, the phase duration determina-tion 2928 may use the data collection 2904 and the event detection 2914 to determine whether the correct phase duration is being applied for a user in the cessation program 2902. If yes, then the user may continue to follow the recommended cessation program. If no, then the user may extend the phase duration of the phase the user is currently in within the cessation program 2902 or may truncate (e.g., shorten) the phase duration of the phase the user is currently in within the cessation program 2902. In examples, the behavioral therapy determination 2930 may use the data collection 2904 and the event detection 2914 to determine a type of behavior therapy for a user. Types of behavior therapy could include providing (e.g., sending a text mes-sage, displaying a notification, or a like) a motivation for continuing with the cessation program 2902, prompting the user to start a breathing exercise, prompting the user to deploy one or more coping strategies and/or distraction techniques, prompting the user to review goal setting, etc. Each of the program interventions and/or modifications 2924 may be applied to the recommended cessation program to update the personalized nicotine replacement therapy 2932.

Figure 30:
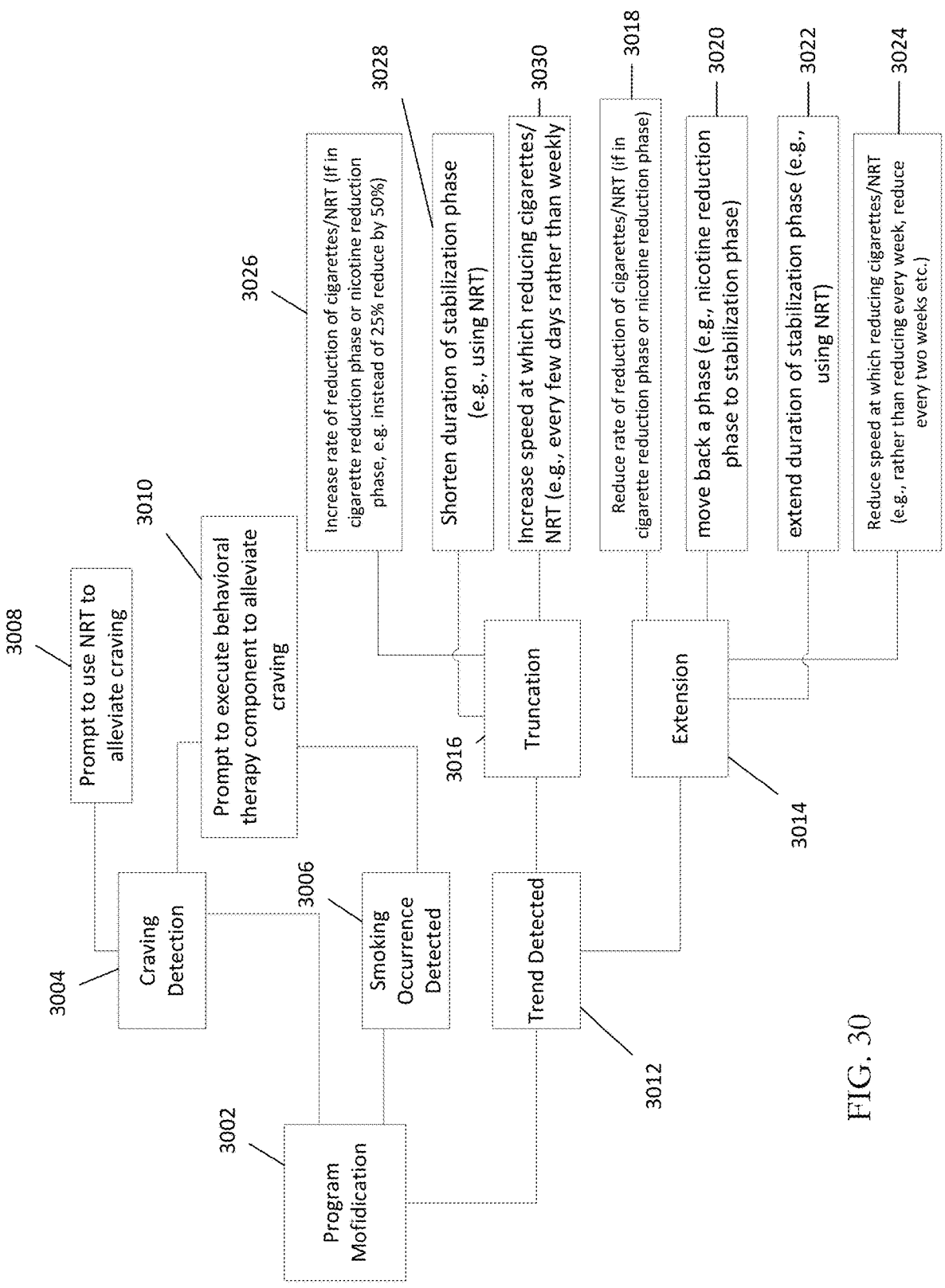
FIG. 30 depicts an example block diagram for a program modification of a cessation program.

FIG. 30 depicts an example block diagram for a program modification of a cessation program. A program modification 3002 may be applied to detect a nicotine craving at 3004. In examples, if a nicotine craving is determined at 3004, the program may prompt the use of NRT to alleviate craving at 3008. In examples, if a nicotine craving is determined at 3004, the program may (e.g., may also) execute behavioral therapy component to alleviate craving at 3010. The program modification 3002 may be applied to detect a smoking occurrence at 3006. In examples, if a smoking occurrence is determined at 3006, the program may execute behavioral therapy component to alleviate craving at 3010.

The program modification 3002 may be applied to detect trends at 3012. If a trend is detected a 3012, the program may be extended at 3014 or truncated at 3016. In examples, if the program is extended at 3014, the program may reduce the rate of reduction of cigarettes if the program is in the cigarette reduction phase or may reduce the rate or NRT if the program is in the nicotine reduction phase at 3018, which is described in further detail herein. In examples, if the program is extended at 3014, the program may move back a phase (e.g., move from the nicotine reduction phase to the stabilization phase) at 3020. In examples, if the program is extended at 3014, the program may extend the duration of a phase (e.g., the use of NRT in the stabilization phase) at 3022. In examples, if the program is extended at 3014, the program may reduce the speed of reducing cigarettes/NRT (e.g., rather than reducing every week, reduce every two weeks, etc.) at 3024.

In examples, if the program is truncated at 3016, the program may increase the rate of reduction of cigarettes/NRT (e.g., if in the cigarette reduction phase or the nicotine reduction phase, reduce cigarettes/NRT by 50% rather than by 25%) at 3026. In examples, if the program is truncated at 3016, the program may shorten the duration of a phase (e.g., the use of NRT in the stabilization phase) at 3028. In examples, if the program is truncated at 3016, the program may increase the speed of reducing cigarettes/NRT (e.g., reduce cigarettes/NTR every few days rather than weekly) at 3030.

Figures 31A, 31B:
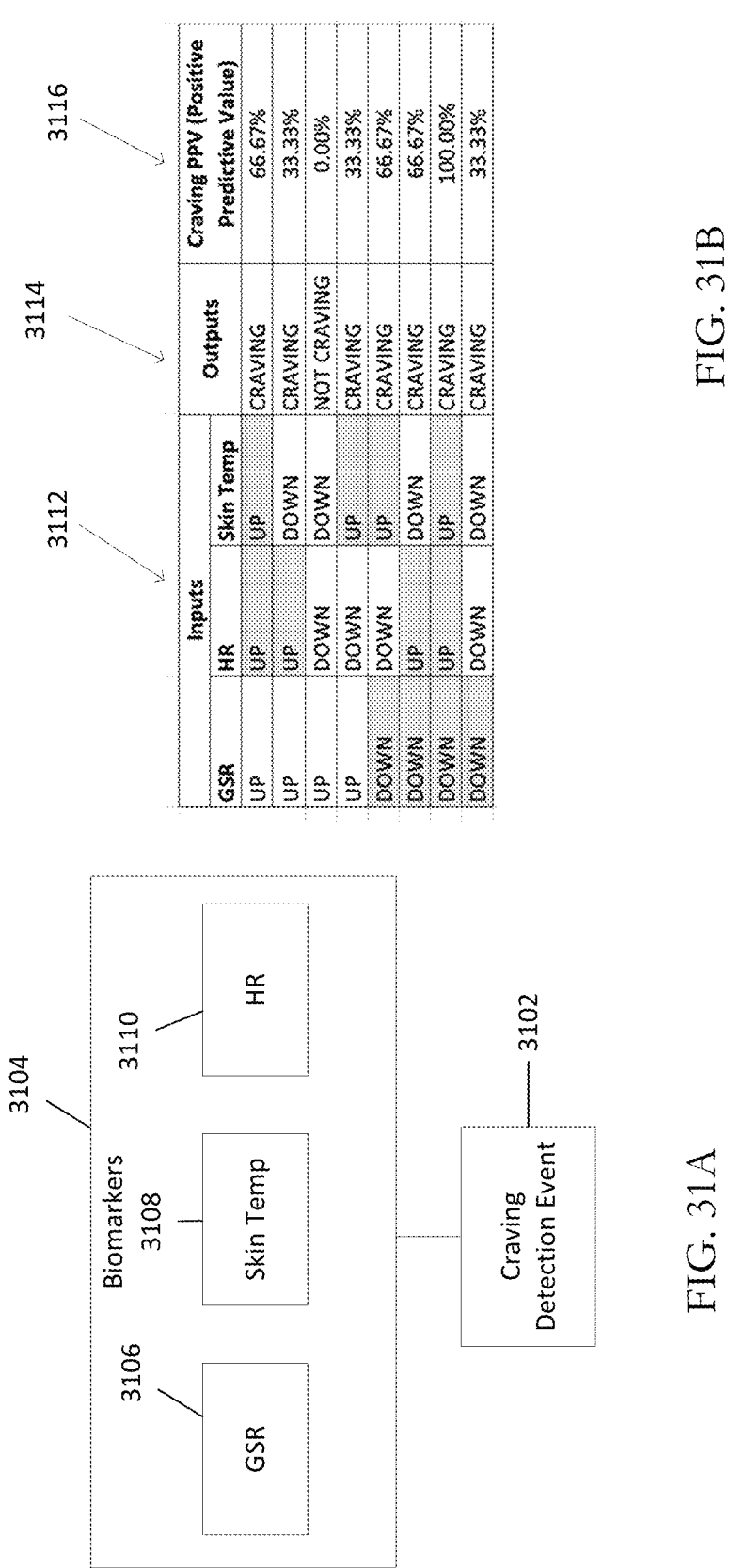
FIG. 31A depicts an example block diagram of a craving detection event.
FIG. 31B depicts an example table for determining a craving detection event.

FIG. 31A depicts an example block diagram of a craving detection event. FIG. 31B depicts an example table for determining a craving detection event. As shown in FIG. 31A, a craving detection event 3102 may be determined by a number of biomarkers 3104. The biomarkers 3104 may include GSR 3106, skin temperature 3108, and/or heart rate 3110. As shown in FIG. 31B, each of the biomarkers 3104 may be used as craving event inputs 3112 to determine a craving event output 3114. The craving event output 3114 may indicate whether there is a craving or not. As shown in FIG. 31B, a craving positive predictive value (craving PPV) 3116 may be calculated using the craving event inputs 3112. The craving PPV 3116 may be calculated by dividing the result of the number of craving event inputs 3112 that are positively predictive of a craving by the total number of craving event inputs 3112.

As shown in FIG. 31B, craving event inputs 3112 that are positively predictive of a craving are shaded and craving event inputs 3112 that are negatively predictive of a craving are not shaded. In examples, craving input events 3112 may be indicated as "UP" or "DOWN" in comparison to craving input events previously measured. In examples, craving event inputs 3112 of the GSR 3106 may be "UP" or "DOWN" compared with a previously measured GSR. In examples, craving event inputs 3112 of the heart rate 3110 may be "UP" or "DOWN" compared with a previously measured heart rate. In examples, craving event inputs of the skin temperature 3108 may be "UP" or "DOWN" compared with a previously measured skin temperature.

As shown in FIG. 31B, craving event inputs 3112 of the GSR 3106 being "DOWN" are shaded, which may be positively predictive of a craving, while craving evening inputs 3112 of the GSR 3106 being "UP" are not shaded, which may be negatively predictive of a craving. Craving event inputs 3112 of the heart rate 3110 being "UP" are shaded, which may be positively predictive of a craving, while craving evening inputs 3112 of the heart rate 3110 being "DOWN" are not shaded, which may be negatively predictive of a craving. Craving event inputs 3112 of the skin temperature 3008 being "UP" are shaded, which may be positively predictive of a craving, while craving evening inputs 3112 of the skin temperature 3008 being "DOWN" are not shaded, which may be negatively predictive of a craving.

In examples, if one craving event input 3112 out of the three craving event inputs 3112 is shaded and positively predictive of a craving, it may lead to a craving event output 3114 indicating "CRAVING". If one craving event input 3112 out of the three craving event inputs 3112 is shaded and positively predictive of a craving, it may have a craving PPV 3116 of 33.33% (1/3). In examples, if two craving event inputs 3112 out of the three craving event inputs 3112 are shaded and positively predictive of a craving, it may lead to a craving event output 3114 indicating "CRAVING". If two craving event inputs 3112 out of the three craving event inputs 3112 are shaded and positively predictive of a craving, it may have a craving PPV 3116 of 66.67% (2/3). In examples, if three craving event inputs 3112 out of the three craving event inputs 3112 are shaded and positively predictive of a craving, it may lead to a craving event output 3114 indicating "CRAVING". If three craving event inputs 3112 out of the three craving event inputs 3112 are shaded and positively predictive of a craving, it may have a craving PPV 3116 of 100% (3/3). In examples, if zero craving event inputs 3112 out of the three craving event inputs 3112 are shaded and positively predictive of a craving, it may lead to a craving event output 3114 indicating "NO CRAVING". If zero craving event inputs 3112 out of the three craving event inputs 3112 are shaded and positively predictive of a craving, it may have a craving PPV 3116 of 0% (0/3).

Figure 32C:
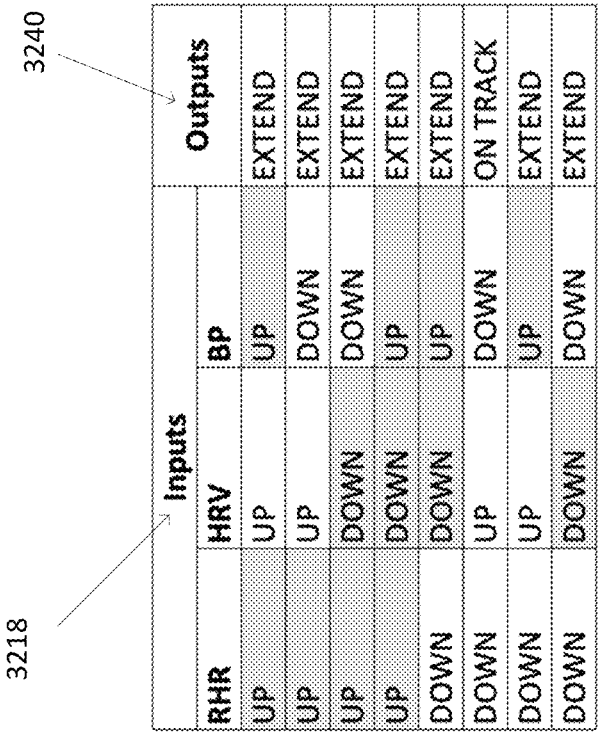
Figure 32A:
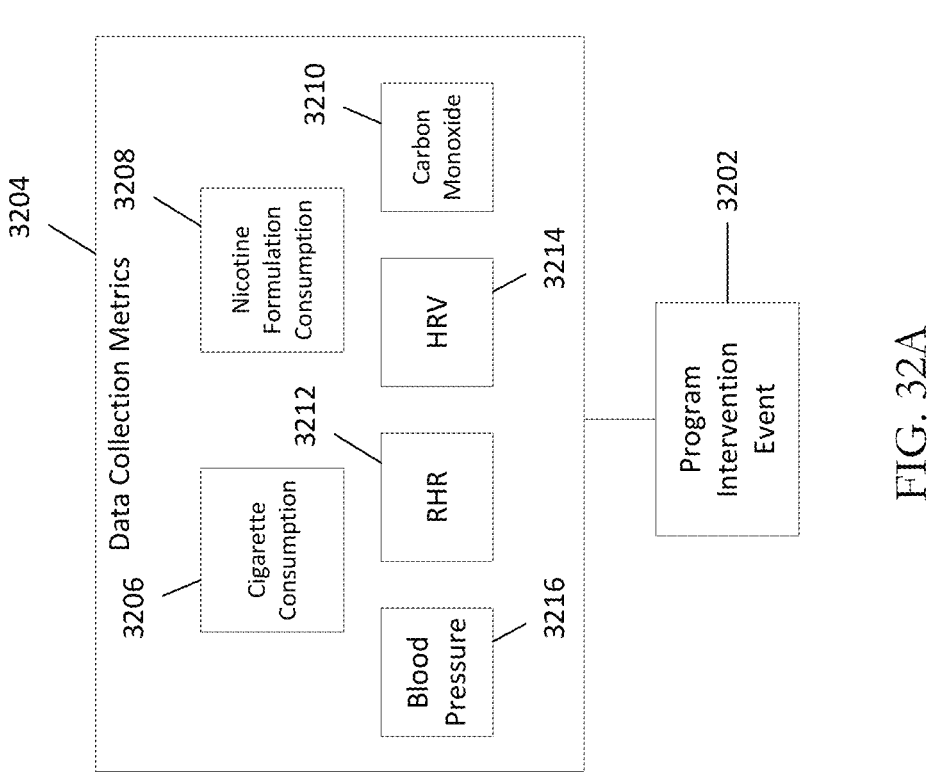
FIG. 32A depicts an example block diagram of a program intervention event.

FIG. 32A depicts an example block diagram of a program intervention event. FIGS. 32B-32C depict example tables for determining a program intervention event. As shown in FIG. 32A, a program intervention event 3202 may be determined by data collection metrics 3204. The data collection metrics 3204 may include cigarette consumption 3206, NRT consumption 3208, carbon monoxide 3210, RHR 3212, HRV 3214, and/or blood pressure 3216. As shown in FIG. 32B, some of the data collection metrics 3204 may be used as program intervention inputs 3218 to determine program intervention outputs. In examples, the program intervention inputs 3218 may be the cigarette consumption 3206, the NRT consumption 3208, and/or the carbon monoxide 3210.

Cessation programs may include (e.g., may be divided into) a cigarette reduction phase 3222, a stabilization phase 3224, and a nicotine reduction phase 3226. The cigarette reduction phase 3222 may include a cigarette reduction phase output 3230. The stabilization phase 3224 may include a stabilization phase output 3234. The NRT reduction phase 3226 may include a NRT reduction phase output 3238. Each of the cigarette reduction phase output 3230, the stabilization phase output 3234, and the NRT reduction phase output 3238 may be determined by the program intervention inputs 3218.

During the cigarette reduction phase 3222, cigarettes may be reduced or eliminated and replaced with NRT. The NRT may act as a replacement to cigarettes to provide (e.g., temporarily provide) nicotine for users while reducing or eliminating cigarettes. In examples, the cigarette reduction phase 3222 may be the first phase within a cessation program (e.g., during weeks 1-4 of the cessation program). During the stabilization phase 3224, cigarettes may be entirely eliminated while the amount of NRT stays the same or decreases. The stabilization phase 3224 may be the second phase within a cessation program (e.g., during weeks 5-8 of a cessation program). During the NRT reduction phase 3226, the NRT use should be reduced or eliminated, reducing or eliminating the nicotine intake for users. The NRT reduction phase 3226 may be the third and final phase of a cessation program (e.g., during weeks 9-12 of a cessation program). In the NRT reduction phase 3226, users should be on track to entirely eliminate their nicotine intake.

In examples, program intervention inputs 3218 may be indicated as "UP" or "DOWN" in comparison to craving input events previously measured. In examples, program intervention inputs 3218 of the cigarette consumption 3206 may be "UP" or "DOWN" compared with a previously measured cigarette consumption. In examples, program intervention inputs 3218 of the NRT consumption 3208 may be "UP" or "DOWN" compared with a previously measured NRT consumption. In examples, program intervention inputs 3218 of the carbon monoxide 3210 may be "UP" or "DOWN" compared with a previously measured carbon monoxide.

During the cigarette reduction phase 3222, if the program intervention input 3218 of the cigarette consumption 3206, the NRT consumption 3208, and the carbon monoxide 3210 are all indicated as "UP", then the user may be considered behind with regards to their cessation program and the cigarette reduction phase 3222 may be extended, which may be indicated by the cigarette reduction phase output 3230 as "EXTEND". If the program intervention input 3218 of the cigarette consumption 3206 is indicated as "UP", the NRT consumption 3028 is indicated as "DOWN", and the cardon monoxide 3210 is indicated as "UP", then the user may be considered behind with regards to their cessation program and the cigarette reduction phase 3222 may be extended, which may be indicated by the cigarette reduction phase output 3230 as "EXTEND". If the program intervention input 3218 of the cigarette consumption 3206 is indicated as "DOWN", the NRT consumption 3028 is indicated as "UP", and the cardon monoxide 3210 is indicated as "DOWN", then the user may be considered on track with regards to their cessation program, which may be indicated by the cigarette reduction phase output 3230 as "ON TRACK". If the program intervention input 3218 of the cigarette consumption 3206 is indicated as "DOWN", the NRT consumption 3028 is indicated as "DOWN", and the cardon monoxide 3210 is indicated as "DOWN", then the user may be considered ahead with regards to their cessation program and the cigarette reduction phase 3222 may be truncated (e.g., expedited), which may be indicated by the cigarette reduction phase output 3230 as "TRUNCATE". As shown in FIG. 32B, some program intervention inputs 3218 and cigarette reduction phase outputs 3230 are shaded, which may indicate that the combination of program intervention inputs and/or cigarette reduction phase outputs 3230 cannot occur together. In these cases, the cigarette reduction phase output 3230 may be indicated as "N/A".

During the stabilization phase 3224, if the program intervention input 3218 of the cigarette consumption 3206, the NRT consumption 3208, and the carbon monoxide 3210 are all indicated as "UP", then the user may be considered behind with regards to their cessation program and the stabilization phase 3224 may be extended, which may be indicated by the stabilization phase output 3234 as "EXTEND". If the program intervention input 3218 of the cigarette consumption 3206 is indicated as "UP", the NRT consumption 3028 is indicated as "DOWN", and the cardon monoxide 3210 is indicated as "UP", then the user may be considered behind with regards to their cessation program and the stabilization phase 3224 may be extended, which may be indicated by the stabilization phase output 3234 as "EXTEND". If the program intervention input 3218 of the cigarette consumption 3206 is indicated as "DOWN", the NRT consumption 3028 is indicated as "UP", and the cardon monoxide 3210 is indicated as "DOWN", then the user may be considered behind with regards to their cessation program and the stabilization phase 3224 may be extended, which may be indicated by the stabilization phase output 3234 as "EXTEND". If the program intervention input 3218 of the cigarette consumption 3206 is indicated as "DOWN", the NRT consumption 3028 is indicated as "DOWN", and the cardon monoxide 3210 is indicated as "DOWN", then the user may be considered ahead with regards to their cessation program and the stabilization phase 3224 may be truncated (e.g., expedited), which may be indicated by the stabilization phase output 3234 as "TRUNCATE". As shown in FIG. 32B, some program intervention inputs 3218 and stabilization phase outputs 3234 are shaded, which may indicate that the combination of program intervention inputs and/or stabilization phase outputs 3230 cannot occur together. In these cases, the stabilization phase output 3230 may be indicated as "N/A".

During the NRT reduction phase 3226, if the program intervention input 3218 of the cigarette consumption 3206, the NRT consumption 3208, and the carbon monoxide 3210 are all indicated as "UP", then the user may be considered behind with regards to their cessation program and the NRT reduction phase 3226 may be extended, which may be indicated by the NRT reduction phase output 3238 as "EXTEND". If the program intervention input 3218 of the cigarette consumption 3206 is indicated as "UP", the NRT consumption 3028 is indicated as "DOWN", and the cardon monoxide 3210 is indicated as "UP", then the user may be considered behind with regards to their cessation program and the NRT reduction phase 3226 may be extended, which may be indicated by the NRT reduction phase output 3238 as "EXTEND". If the program intervention input 3218 of the cigarette consumption 3206 is indicated as "DOWN", the NRT consumption 3028 is indicated as "UP", and the cardon monoxide 3210 is indicated as "DOWN", then the user may be considered behind with regards to their cessation program and the NRT reduction phase 3226 may be extended, which may be indicated by the NRT reduction phase output 3238 as "EXTEND". If the program intervention input 3218 of the cigarette consumption 3206 is indicated as "DOWN", the NRT consumption 3028 is indicated as "DOWN", and the cardon monoxide 3210 is indicated as "DOWN", then the user may be considered on track with regards to their cessation program, which may be indicated by the NRT reduction phase output 3238 as "ON TRACK". As shown in FIG. 32B, some program intervention inputs 3218 and NRT reduction phase outputs 3238 are shaded, which may indicate that the combination of program intervention inputs and/or NRT reduction phase outputs 3238 cannot occur together. In these cases, the NRT reduction phase output 3238 may be indicated as "N/A".

As shown in FIG. 32C, some (e.g., some other) data collection metrics 3204 may be used as program intervention inputs 3218 to determine program intervention outputs 3240. In examples, the program intervention inputs 3218 may be the RHR 3212, the HRV 3214, and/or the blood pressure 3216. The program intervention outputs 3240 found in FIG. 32C may act to verify and/or supplement the cigarette reduction phase outputs 3230, stabilization phase outputs 3234, and NRT reduction phase outputs 3238 found in FIG. 32B.

As shown in FIG. 32C, program intervention inputs 3218 that are positively predictive of the need to extend a phase are shaded and the program interventions inputs 3218 that are negatively predictive of the need to extend a phase are not shaded. In examples, program intervention inputs 3218 may be indicated as "UP" or "DOWN" in comparison to program intervention inputs previously measured. In examples, program intervention inputs 3218 of the RHR 3212 may be "UP" or "DOWN" compared with a previously measured RHR. In examples, program intervention inputs 3218 of the HRV 3214 may be "UP" or "DOWN" compared with a previously measured HRV. In examples, program intervention inputs 3218 of the blood pressure 3216 may be "UP" or "DOWN" compared with a previously measured blood pressure.

As shown in FIG. 32C, program intervention inputs 3218 of the RHR 3212 being "UP" are shaded, which may be positively predictive of a phase extension, while program intervention events 3218 of the RHR 3212 being "DOWN" are not shaded, which may be negatively predictive of a phase extension. Program interventions inputs 3218 of the HRV 3214 being "DOWN" are shaded, which may be positively predictive of a craving, while program intervention inputs 3218 of the HRV 3214 being "UP" are not shaded, which may be negatively predictive of a phase extension. Program intervention inputs 3218 of blood pressure 3216 being "UP" are shaded, which may be positively predictive of a phase extension, while program intervention inputs 3218 of the blood pressure 3216 being "DOWN" are not shaded, which may be negatively predictive of a craving.

In examples, if one program intervention input 3218 out of the three program intervention inputs 3218 is shaded and positively predictive of a craving, it may lead to a program intervention output 3240 indicating "EXTEND". In examples, if two program intervention inputs 3218 out of the three program intervention inputs 3218 are shaded and positively predictive of a craving, it may lead to a program intervention output 3240 indicating "EXTEND". In examples, if three program intervention inputs 3218 out of the three program intervention inputs 3218 are shaded and positively predictive of a craving, it may lead to a program intervention output 3240 indicating "EXTEND". In examples, if zero program intervention inputs 3218 out of the three program intervention inputs 3218 are shaded and positively predictive of a craving, it may lead to a program intervention output 3240 indicating "ON TRACK".

Figures 33A, 33B:
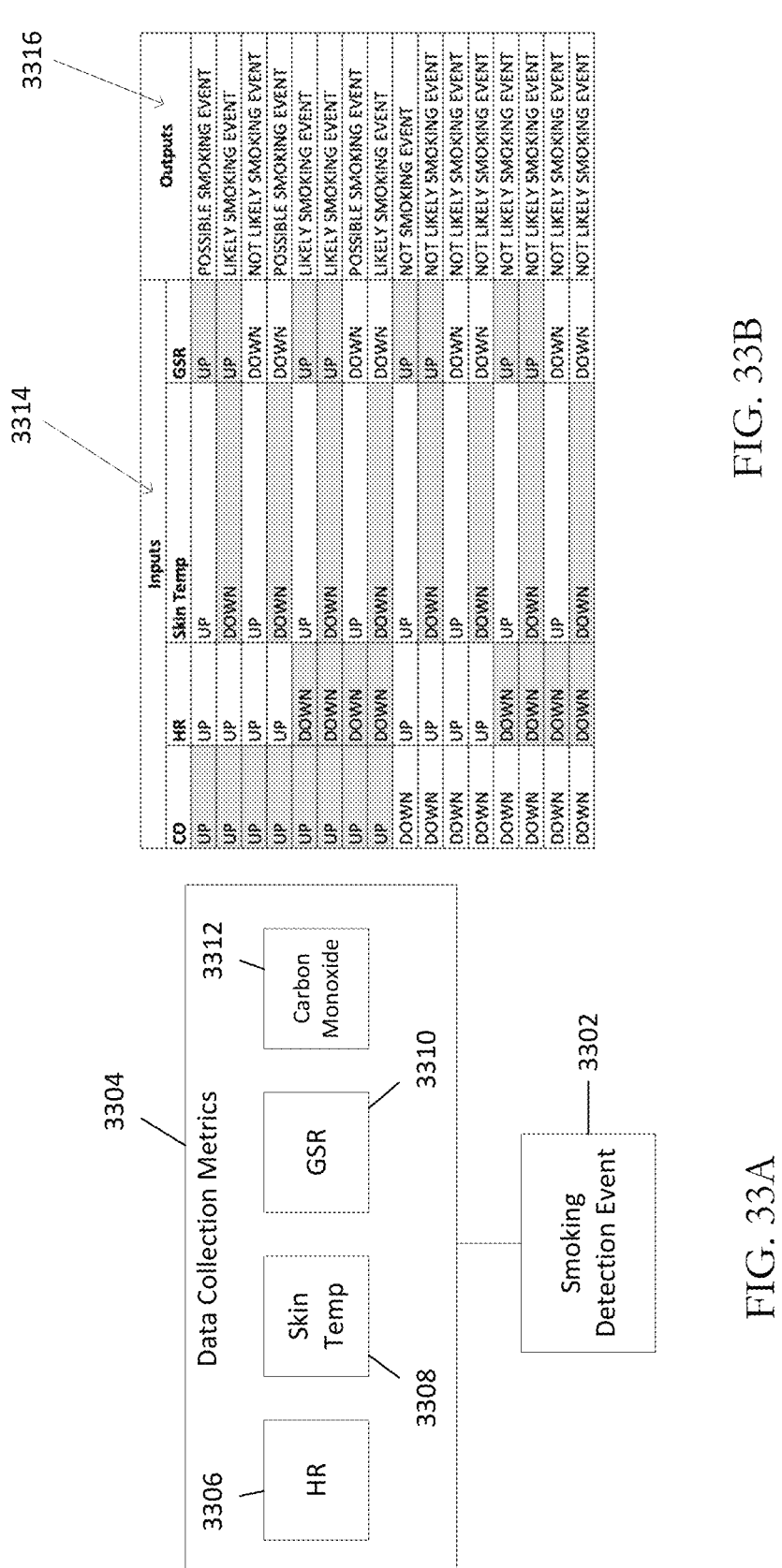
FIG. 33A depicts an example block diagram of a smoking detection event.
FIG. 33B depicts an example table for determining a smoking detection event.

FIG. 33A depicts an example block diagram of a smoking detection event. FIG. 33B depicts an example table for determining a smoking detection event. As shown in FIG. 33A, a smoking detection event 3302 may be determined by a data collection metrics 3304. The data collection metrics 3304 may include heart rate 3306, skin temperature 3308, GSR 3310, and/or carbon monoxide 3312. As shown in FIG. 33B, each of the data collection metrics 3304 may be used as smoking event inputs 3314 to determine a smoking event output 3316. The smoking event output 3316 may indicate whether there is a smoking event, not likely a smoking event, a possible smoking event, not likely a smoking event, or no smoking event.

As shown in FIG. 33B, smoking event inputs 3314 that are positively predictive of a smoking event are shaded and smoking event inputs 3314 that are negatively predictive of a smoking event are not shaded. In examples, smoking event inputs 3314 may be indicated as "UP" or "DOWN" in comparison to smoking event inputs 3314 previously measured. In examples, smoking event inputs 3314 of the carbon monoxide 3312 may be "UP" or "DOWN" compared with a previously measured carbon monoxide. In examples, smoking event inputs 3314 of the heart rate 3306 may be "UP" or "DOWN" compared with a previously measured heart rate. In examples, smoking event inputs 3314 of the skin temperature 3308 may be "UP" or "DOWN" compared with a previously measured skin temperature. In examples, smoking event inputs 3314 of the GSR 3310 may be "UP" or "DOWN" compared with a previously measured GSR.

As shown in FIG. 33B, smoking event inputs 3314 of the carbon monoxide 3310 being "UP" are shaded, which may be positively predictive of a smoking event, while smoking event inputs 3314 of the carbon monoxide 3310 being "DOWN" are not shaded, which may be negatively predictive of a smoking event. Smoking event inputs 3314 of the heart rate 3306 being "DOWN" are shaded, which may be positively predictive of a smoking event, while smoking event inputs 3314 of the heart rate 3110 being "UP" are not shaded, which may be negatively predictive of a smoking event. Smoking event inputs 3314 of the skin temperature 3308 being "DOWN" are shaded, which may be positively predictive of a smoking event, while smoking event inputs 3314 of the skin temperature 3008 being "UP" are not shaded, which may be negatively predictive of a smoking event. Smoking event inputs 3314 of the GSR 3310 being "UP" are shaded, which may be positively predictive of a smoking event, while smoking event inputs 3314 of the GSR 3310 being "DOWN" are not shaded, which may be negatively predictive of a smoking event.

In examples, if carbon monoxide 3310 is shaded along with zero other (e.g., out of the three other) smoking event inputs 3314 shaded, it may lead to a smoking event output 3316 indicating "NOT LIKELY SMOKING EVENT". In examples, if carbon monoxide 3310 is shaded along with one other (e.g., out of the three other) smoking event input 3314 shaded, it may lead to a smoking event output 3316 indicating "POSSIBLE SMOKING EVENT". In examples, if carbon monoxide 3310 is shaded along with two other (e.g., out of the three other) smoking event inputs 3314 shaded, it may lead to a smoking event output 3316 indicating "LIKELY SMOKING EVENT". In examples, if carbon monoxide 3310 is shaded along with three other (e.g., out of the three other) smoking event inputs 3314 shaded, it may lead to a smoking event output 3316 indicating "SMOKING EVENT".

In examples, if carbon monoxide 3310 is not shaded along with zero other (e.g., out of the three other) smoking event inputs 3314 not shaded, it may lead to a smoking event output 3316 indicating "NO SMOKING EVENT". In examples, if carbon monoxide 3310 is not shaded along with one other (e.g., out of the three other) smoking event input 3314 not shaded, it may lead to a smoking event output 3316 indicating "NOT LIKELY SMOKING EVENT". In examples, if carbon monoxide 3310 is not shaded along with two other (e.g., out of the three other) smoking event inputs 3314 not shaded, it may lead to a smoking event output 3316 indicating "NOT LIKELY SMOKING EVENT". In examples, if carbon monoxide 3310 is not shaded along with three other (e.g., out of the three other) smoking event inputs 3314 not shaded, it may lead to a smoking event output 3316 indicating "NOT LIKELY SMOKING EVENT".

Figure 34:
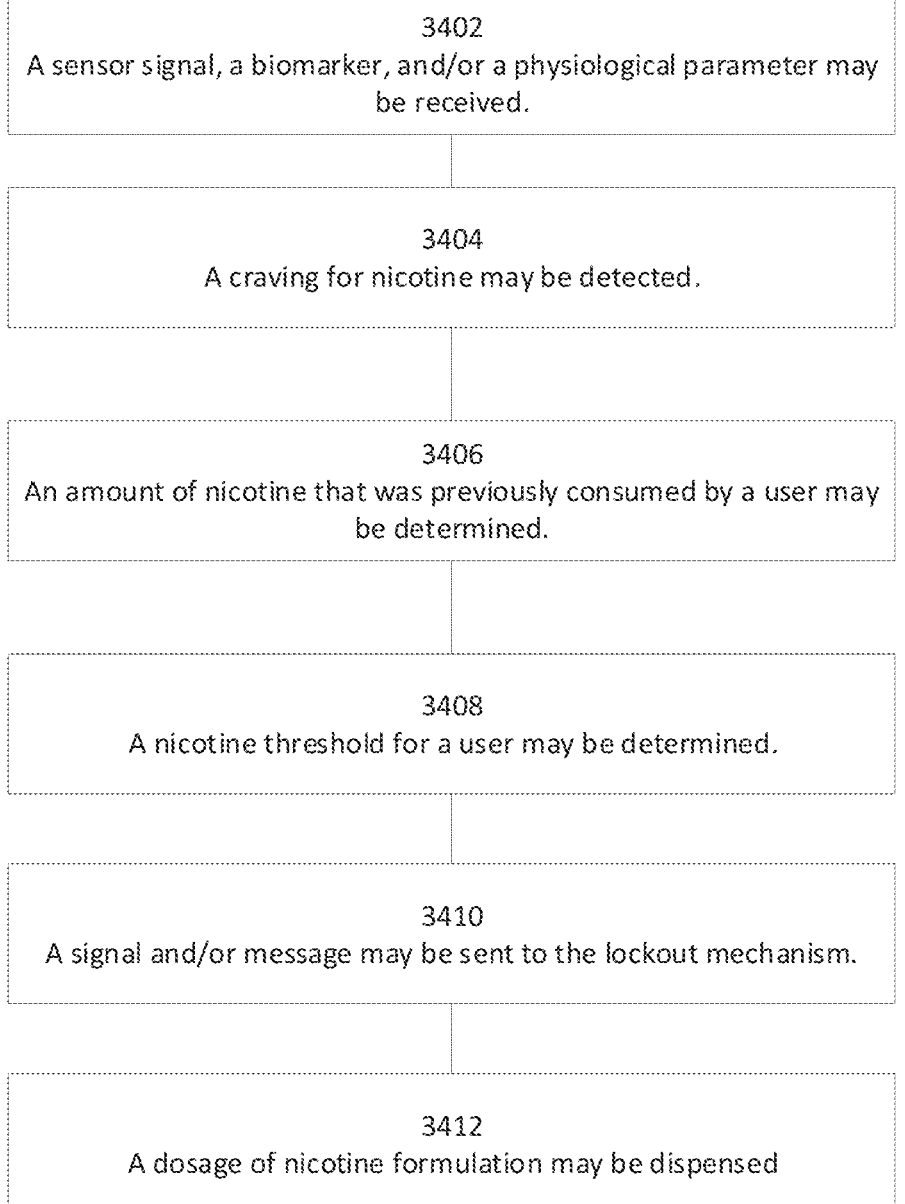
FIG. 34 depicts a method for providing nicotine replacement therapy that may be implemented by a device.

FIG. 34 depicts a method for providing nicotine replacement therapy that may be implemented by a device. The device may comprise a dispenser body. The device may comprise a dispenser for dispensing a nicotine formulation. The device may comprise an actuating member mounted to actuate the dispenser. The device may comprise a carriage mounted to move relative to the dispenser body when contacted by the actuating member. The device may comprise a sensor that may be configured to sense a movement of the carriage.

The device may comprise a lockout mechanism that may be movable between an operative position that allows the actuating member to move so as to actuate the dispenser, and a non-operative position that prevents the actuating member from moving. The device may comprise a transmitter for sending a nicotine amount signal that may indicate an amount of nicotine that may have been previously consumed by a user. The device may comprise a receiver for receiving a locking signal that may indicate that the lockout mechanism is to be moved to the non-operative position. The device may comprise a sensor for measuring a physiological parameter.

The device may comprise a processor that may be configured to perform a one or more actions shown for the method 3400. For example, the device may perform one or more of 3402, 3404, 3406, 3408, 3410, 3412, and/or any combination thereof.

At 3402, a sensor signal, a biomarker, and/or a physiological parameter may be received. The sensor signal, biomarker, and/or physiological parameter may be used as described herein. For example, the biomarker may be used to determine nicotine consumption for a user, a cessation phase for a user, progression within a cessation phase for the user, a health parameter for the user, a craving for nicotine, and/or the like.

In an example, a sensor signal may be received from a sensor for measuring a physiological parameter that may indicate a value of the physiological parameter of the user. The value of the physiological parameter of the user may be determined based on the sensor signal. The value of the physiological parameter of the user may sent, for example, to a user and/or a device. The physiological parameter may be any biometric parameter and/or biomarker as described herein.

In an example, data may be received from a sensor. The data may include one or more of a heart rate, heart rate variability, blood pressure, temperature, respiration rate, oxygen saturation, carboxyhemoglobin, carbon monoxide, galvanic skin response, and accelerometer data from a wearable device associated with a user. A personalized nicotine replacement or reduction therapy program may be modified for the user based on the received data from the wearable device.

At 3404, a craving for nicotine may be detected. The craving for nicotine may be detected using user input, biomarkers, a signal from a sensor, a physiological parameter, a history of nicotine usage, and the like. In an example, a motion signal may be received from a motion sensor. It may be determined from the motion signal that the user is fidgeting for a period of time. User fidgeting may indicate that the user may be experiencing a craving for nicotine. An indication of the user fidgeting and/or an indication of a nicotine craving may be sent, for example, to a user (e.g., a notification) and/or a device, such as a smartphone.

In an example, it may be determined the user is experiencing a nicotine craving using at least one of a detected motion, a physical location, a time of day, a scheduled activity, a calendar of the user, social media data, and a biometric measurement. In an example, it may be determined that the user is experiencing a nicotine craving using a resting heart rate associated with the user or using a perceived change in a heart rate for the user.

In an example, an anticipated craving time may be determined. For example, the anticipated craving time may be determined using one or more of a time that a first dosage of the nicotine formulation was dispensed and the amount of nicotine that was previously consumed by the user. A notification suggesting a second dosage of the nicotine formulation may be sent at the anticipated craving time.

In an example, an anticipated craving time may be determined and/or a smoking lapse event may be detected. A heart rate data associated with a user may be received. A heart rate trend and/or a change in heart rate trend for the user may be determined using the received heart rate data. An expected time of occurrence of a smoking lapse event may be determined.

An instruction, message, and/or signal may be sent. For example, a message may be sent to request that a user dispense nicotine formulation at the expected time of occurrence of a smoking lapse event or prior thereto. As an example, a signal may be sent to a nicotine dispensing device to instruct the nicotine dispensing device to dispense and/or allow a user to dispense nicotine formulation at the expected time of occurrence of a smoking lapse event or prior thereto. As an example, a message may be sent to instruct an actuating member to actuate the dispenser such that the dispenser dispenses an amount of nicotine formulation at the expected time of occurrence of a smoking lapse event or prior thereto.

At 3406, An amount of nicotine that was previously consumed by a user may be determined. In an example, the amount of nicotine that was previously consumed may be determined using a count of the dispenser actuations. A number of actuations of the dispenser may be determined. The number of actuations of the dispenser may be for and/or associated with a period of time. A concentration of the nicotine formulation may be determined. An amount of nicotine consumed by the user during the period of time may be determined based on the number of actuations and the concentration of the nicotine formulation. The amount of nicotine that was previously consumed by the user may be determined based on the amount of nicotine consumed by the user during the period of time.

In an example, the amount of nicotine that was previously consumed by the user by determining one or more tobacco products that may have been consumed by the user within a time period. A level of nicotine associated with the one or more tobacco products may be determined. For example, a level of nicotine may be determined for an electronic cigarette that may have been consumed by a user.

In an example, a total amount of nicotine consumed may be determined. The total amount of nicotine consumed may indicate the amount of nicotine that was previously consumed by a user. An amount of nicotine to be dispensed may be determined. A user may be allowed to dispense nicotine formulation when the total amount of nicotine consumed and the amount of nicotine to be dispensed may be less than a maximum nicotine dosage for a day. For example, an actuating member may be instructed to actuate the dispenser such that the dispenser dispenses the amount of nicotine when the total amount of nicotine consumed and the amount of nicotine to be dispensed is less than a maximum nicotine dosage for a day. A user may be preventing from dispensing nicotine formulation when the total amount of nicotine consumed and the amount of nicotine to be dispensed may be greater than or equal to a maximum nicotine dosage for a day.

At 3408, a nicotine threshold for a user may be determined. The nicotine threshold may account for nicotine consumption from one or more sources, such as cigarettes, smokeless tobacco, electronic cigarettes, heated tobacco, nicotine formulation, nicotine gum, and the like. The nicotine threshold may be personalized for the user. The nicotine threshold may be based on an age of the user, a weight of the user, a cessation phase for the user, a nicotine consumption rate for the user, and the like. The nicotine threshold may be determined to prevent a user from receiving a fatal dosage of nicotine, an overdose of nicotine, an amount of nicotine that may be harmful to nicotine cessation, and/or the like.

In an example, it may be determined that the amount of nicotine that was previously consumed by the user may be at or above the nicotine threshold. It may be determined that the user may not be allowed to consume additional nicotine. The lockout mechanism may be instructed to prevent the dispenser from dispensing nicotine formulation (e.g., at 3410).

In an example, it may be determined that the amount of nicotine that was previously consumed by the user may be below the nicotine threshold. It may be determined that the user may be allowed to consume additional nicotine. A message may be sent (e.g., a notification) to user to advise the user to dispense a dose of nicotine to, for example, reduce a nicotine craving. The lockout mechanism may be instructed to allow the dispense to dispense nicotine formulation (e.g., at 3410)

In an example, a nicotine threshold for a user may be determined using one or more smoking behaviors for the user. For example, one or more smoking behaviors for the user may be determined. A smoking cessation program for the user may be determined based on the one or more smoking behaviors for the user.

At 3410, a signal, such as a lockout mechanism signal, and/or a message may be sent to the to the lockout mechanism. In an example, the lockout mechanism signal may cause the lockout mechanism to move to the operative position. For example, it may be determined that the user has not exceeded the nicotine threshold, is experiencing a nicotine craving, and/or is permitted to consume nicotine. And a signal may be sent to cause the lockout mechanism to move and/or stay in the operative position such that the user may dispense nicotine formulation.

In an example, the lockout mechanism signal may cause the lockout mechanism to move to the non-operative position. In an example, it may be determined that amount of nicotine that was previously consumed by the user may exceed the nicotine threshold. And the lockout mechanism signal may be sent on a condition that the amount of nicotine that was previously consumed by the user exceeds the nicotine threshold to cause the lockout mechanism to move to the non-operative position.

In an example, it may be determined that the user may be experiencing a nicotine craving (e.g., at 3402) and that a condition may indicate that the user should not receive a dose of the nicotine formulation. And a lockout mechanism signal may be sent to the lockout mechanism that may cause the lockout mechanism to move to the non-operative position (e.g., even though the user may be experiencing a nicotine craving).

In an example, the lockout mechanism may be included in another device, which may be a nicotine delivery device. A message may be sent to the nicotine delivery device to instruct the nicotine delivery device to allow a dose of nicotine to be dispensed.

At 3412, a dosage of nicotine formulation may be dispensed. For example, a device may dispense the nicotine formulation. In another example, the device may send a message and/or signal to a nicotine dispensing device to dispense the nicotine formulation.

In an example, a dosage of the nicotine formulation may be dispensed. The dosage of the nicotine formulation may be detected based on a signal from a sensor, as described herein. An indication of the dosage of the nicotine formulation may be sent. For example, the user may be notified of the dosage of the nicotine formulation. In another example, a message may be sent to a smartphone indicating that the dosage of the nicotine formulation may have dispensed.

A time that the dosage of the nicotine formulation was dispensed may be determined. And the indication of the dosage may indicate the time.

A device for providing nicotine replacement therapy may be provided. The device may comprise a dispenser for dispensing a nicotine formulation. The device may comprise an actuating member mounted to actuate the dispenser. The device may comprise a lockout mechanism that may be movable between an operative position that may allow the actuating member to move so as to actuate the dispenser, and a non-operative position that may prevent the actuating member from moving. The device may comprise a processor. The processor may be configured to determine an amount of nicotine that was previously consumed by a user. The processor may be configured to send a lockout mechanism signal to the lockout mechanism that causes the lockout mechanism to move to the non-operative position.

In an example, a nicotine threshold for the user may be determined, wherein the nicotine threshold may account for nicotine consumption from one or more sources. It may be determined whether the amount of nicotine that was previously consumed by the user may exceed the nicotine threshold, wherein the lockout mechanism signal that causes the lockout mechanism to move to the non-operative position may have been sent on a condition that the amount of nicotine that was previously consumed by the user exceeds the nicotine threshold.

In an example, the device may comprise a transmitter that may be used for sending a nicotine amount signal indicating the amount of nicotine that was previously consumed by the user. The device may comprise a receiver that may be used for receiving a locking signal that may indicate that a lockout mechanism is to be moved to the non-operative position.

In an example, the device may comprise a sensor for measuring a physiological parameter.

In an example, the may comprise a transmitter and the processor may be configured to receive a sensor signal from the sensor for measuring a first physiological parameter that indicates a value of the first physiological parameter of the user. The value of the first physiological parameter of the user may be determined based on the sensor signal. The transmitter may be instructed to send the value of the first physiological parameter of the user.

In an example, the processor may be configured to determine a number of actuations of the dispenser associated with a period of time. A concentration of the nicotine formulation may be obtained. An amount of nicotine consumed by the user during the period of time may be determined based on the number of actuations and the concentration of the nicotine formulation, wherein the amount of nicotine that was previously consumed by the user may be determined based on the amount of nicotine consumed by the user during the period of time.

In an example, the processor may be configured to determine that the user is experiencing a nicotine craving and that a condition indicates that the user should not receive a dose of the nicotine formulation, wherein the lockout mechanism signal to the lockout mechanism that causes the lockout mechanism to move to the non-operative position was sent upon determining that the user is experiencing the nicotine craving.

In an example, the device may comprise a motion sensor, and the processor may be configured to receive a motion signal from the motion sensor. It may be determined from the motion signal that the user is fidgeting for a period of time. An indication of the user fidgeting may be sent.

A device for providing nicotine replacement therapy may be provided. The device may comprise a memory and a processor. The processor may be configured to perform a method. It may be determined that a user is experiencing a nicotine craving. An amount of nicotine that was previously consumed by the user may be determined. A nicotine threshold for the user may be determined. It may be determined that the amount of nicotine that was previously consumed by the user is below the nicotine threshold. A message may be sent to advise the user to dispense a dose of nicotine to reduce the nicotine craving.

In an example, the message may be a first message and the processor may be configured to send a second message to a nicotine delivery device that may instruct the nicotine delivery device to allow the dose of nicotine to be dispensed.

In an example, the processor may be configured to that the user may be experiencing a nicotine craving using at least one of a detected motion, a physical location, a time of day, a scheduled activity, a calendar of the user, social media data, and a biometric measurement.

In an example, t the processor may be configured to determine that the user may be experiencing a nicotine craving using a resting heart rate associated with the user or using a perceived change in a heart rate for the user.

In an example, the processor may be configured to determine the amount of nicotine that was previously consumed by the user. For example, one or more tobacco products consumed by the user within a time period may be determined. A level of nicotine associated with the one or more tobacco products may be determined.

In an example, the processor is further configured to determine a nicotine threshold for the user. For example, one or more smoking behaviors for the user may be determined. A smoking cessation program for the user may be determined based on the one or more smoking behaviors for the user.

A device for providing nicotine replacement therapy may be provided. The device may comprise a dispenser body.

The device may comprise a dispenser for dispensing a dosage of a nicotine formulation. The device may comprise an actuating member mounted to actuate the dispenser. The device may comprise a carriage mounted to move relative to the dispenser body when contacted by the actuating member. The device may comprise a sensor configured to sense a movement of the carriage. The device may comprise a processor. The processor may be configured to perform one or more actions. It may be determined that a dosage of the nicotine formulation was dispensed based on a signal from the sensor. An indication of the dosage of the nicotine formulation may be sent.

In an example, the carriage may be a magnetic carriage. The sensor may be a magnetic sensor that may be able to detect when the magnetic carriage is within a range.

In an example, the processor may be configured to determine a time that the dosage of the nicotine formulation was dispensed. The indication of the dosage may further indicate the time.

In an example, the dosage of the nicotine formulation may be a first dosage, and the processor may be configured to determine an amount of nicotine that was previously consumed by a user. An anticipated craving time may be determined using the time that the first dosage of the nicotine formulation was dispensed and the amount of nicotine that was previously consumed by the user. A notification suggesting a second dosage of the nicotine formulation at the anticipated craving time may be provided.

In an example, the processor may be configured to receive heart rate data associated with a user. A heart rate trend and/or a change in heart rate trend for the user may be determined by using the received heart rate data. An expected time of occurrence of a smoking lapse event may be determined. The actuating member may be instructed to actuate the dispenser such that the dispenser dispenses an amount of nicotine formulation at the expected time of occurrence of a smoking lapse event or prior thereto.

In an example, the processor may be configured to receive data. The may include one or more of a heart rate, heart rate variability, blood pressure, temperature, respiration rate, oxygen saturation, carboxyhemoglobin, carbon monoxide, galvanic skin response, and accelerometer data from a wearable device associated with a user. A personalized nicotine replacement or reduction therapy program for the user may be modified based on the received data from the wearable device.

In an example, the processor may be configured to determine a total amount of nicotine consumed. The total amount of nicotine consumed may indicate the amount of nicotine that was previously consumed by a user. An amount of nicotine to be dispensed may be determined. The actuating member may be instructed to actuate the dispenser such that the dispenser dispenses the amount of nicotine when the total amount of nicotine consumed and the amount of nicotine to be dispensed is less than a maximum nicotine dosage for a day.

Figure 35:
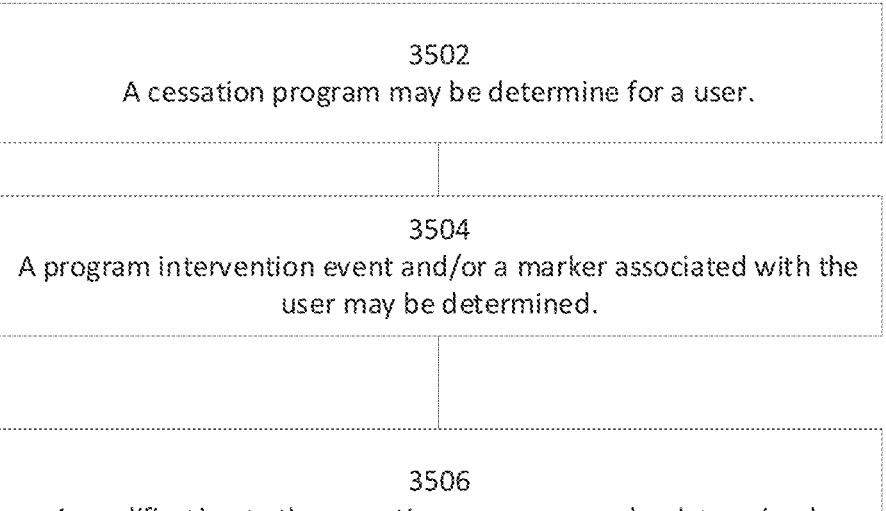
FIG. 35 depicts an example method for providing nicotine replacement therapy that may use a biomarker.

FIG. 35 depicts an example method for providing nicotine replacement therapy that may use a biomarker. The method may be performed by a device that comprises a processor that may be configured to perform a one or more actions shown for the method 3500. For example, the device may perform one or more of 3502, 3504, 3506, and/or any combination thereof.

At 3502, a cessation program for a user may be determined. The cessation program may comprise one or more phases. A phase of the cessation program may be determined as described herein. A phase may be one of a cigarette reduction phase, a nicotine stabilization phase, or a nicotine reduction phase.

At 3504, a program intervention event may be determined. The program intervention event may be determined based on a phase of the cessation program and/or a marker associated with the user.

The program intervention event may be one or more of a craving detection event, a smoking detection event, and a behavioral intervention event. In an example, it may be determined that a behavioral intervention may have been recommended to a user. It may be determined that the previously recommended behavioral intervention may not have been effective. A modification to the cessation program and/or a phase of the cessation program may be made based on the determination that the previously recommended behavioral intervention was not effective. A different behavioral intervention may be suggested to the user when it is determined that the previously recommend behavioral intervention was not effective.

The marker may comprise one or more of a cigarette count, nicotine data, a user biomarker, an indicator of user behavior, a craving detection, and a smoking detection. The marker may comprise one or more of a heart rate, a resting heart rate, a heart rate variability, a blood pressure, a temperature of the user, a respiration rate, an oxygen saturation, a skin temperature, a detection of carbon monoxide, and a galvanic skin response.

The program intervention event may be determined using a cigarette consumption rate for the user. For example, a nicotine formulation consumption rate for the user may be determined. A carbon monoxide saturation level for the user may be determined. The program intervention event may be based on the cigarette consumption rate, the nicotine formulation consumption rate, and the carbon monoxide saturation level for the user.

The program intervention event may be a smoking detection event. For example, a smoking detection event may be determined based on a biomarker associated with the user.

The program intervention event may be a nicotine consumption detection event. For example, a nicotine consumption detection event may be determined based on a biomarker associated with the user.

At 3506, a modification to the cessation program may be determined. The modification to the cessation program may be based on the program intervention event. The modification to the cessation program may be one or more of a rate of reduction of cigarettes, a duration of the phase, a speed at which to reduce cigarettes, a rate of reduction of nicotine replacement therapy, and a speed at which to reduce the nicotine replacement therapy.

The modification to the cessation program may be determined using a cessation trend. A cessation trend may be indicated by the program intervention event. A duration for a phase of the cessation program may be changed based on the cessation trend. For example, the program intervention event may indicate that the user has increased their smoking, the cessation trend may indicate an increase in cigarette consumption, and the duration of cigarette reduction phase may be extended.

The modification to the cessation program may be determined based on the phase and/or a smoking detection event. For example, the program intervention event may be a smoking detection event. It may be determined that the phase may be a cigarette reduction phase, and it may be determined that the cigarette reduction phase may be extended based on the smoking detection event.

The modification to the cessation program be based on a biomarker, a biomarker trend, and/or a smoking detection event. A user may be assigned to a second phase of the cessation program when it is determined that the biomarker trend has exceeded the threshold. A rate of cigarette consumption may be determined using a smoking detection event. A duration for the second phase of the cessation program may be determined based on the rate of cigarette consumption.

The modification to the cessation program may be determined based on rate of cigarette consumption. The rate of cigarette consumption may be determined using a smoking event. It may be determined that a threshold for a biomarker trend may have been exceeded. The rate of consumption may be determined using the smoking detection event when the biomarker trend may have exceeded the threshold. A duration for a phase of the cessation program may be determined based on the rate of cigarette consumption.

The modification to the cessation program may be based on a cessation program and a program intervention event that may be a smoking event. For example, a cigarette consumption rate for the user may be determined using a smoking detection event. An increase to a duration of a first phase may be determined using the smoking detection event. The increase to the duration of the first phase may exceed a threshold. The user may be assigned to a second phase of the cessation program when the duration of the first phase may exceed a threshold.

A modification to the cessation program may be determined based on the phase and a nicotine consumption detection event. For example, the program intervention event may be a nicotine consumption detection event. It may be determined that the phase may be a cigarette reduction phase, and it may be determined that the cigarette reduction phase may be extended based on the smoking detection event. In an example, modification to the cessation program may comprise assigning a user to a phase of the cessation program, determine a rate of nicotine consumption using the nicotine detection event, and determining a duration for the phase of the cessation program based on the rate of nicotine consumption.

A device for providing nicotine replacement therapy may be provided. The device may comprise a processor. The processor may be configured to perform one or more actions. A cessation program for a user may be determined. A program intervention event based on a phase of the cessation program may be determined. A marker associated with the user may be determined. A modification to the cessation program may be determined based on the program intervention event.

In an example, the marker may comprise one or more of a cigarette count, nicotine data, a user biomarker, an indicator of user behavior, a craving detection, and a smoking detection.

In an example, the marker may comprise one or more of a heart rate, a resting heart rate, a heart rate variability, a blood pressure, a temperature of the user, a respiration rate, an oxygen saturation, a skin temperature, a detection of carbon monoxide, and a galvanic skin response.

In an example, the phase is one of a cigarette reduction phase, a nicotine stabilization phase, or a nicotine reduction phase.

In an example, the program intervention event may be one or more of a craving detection event, a smoking detection event, and a behavioral intervention event In an example, the modification to the cessation program that may be based on the program intervention event may comprises a change to one or more of a rate of reduction of cigarettes, a duration of the phase, a speed at which to reduce cigarettes, a rate of reduction of nicotine replacement therapy, and a speed at which to reduce the nicotine replacement therapy.

In an example, the marker may be a cigarette consumption rate for the user, and wherein the processor may be configured to determine the program intervention event. For example, a nicotine formulation consumption rate for the user may be determined. A carbon monoxide saturation level for the user may be determined. The program intervention event may be determined based on the cigarette consumption rate, the nicotine formulation consumption rate, and the carbon monoxide saturation level for the user.

In an example, the modification to the cessation program may be determined using a cessation trend. For example, a cessation trend may be indicated by the program intervention event. A duration for the phase of the cessation program may be changed based on the cessation trend. In another example, the modification may be based on a determination that a biomarker trend may have exceed a threshold.

A device for providing nicotine replacement therapy may be provided. The device may comprise a processor that may be configured to perform one or more actions. A phase of a cessation program associated with a user may be determined. A smoking detection event based on a biomarker associated with the user may be determined. A modification to the cessation program may be determined based on the phase and the smoking detection event.

In an example, the biomarker may be one or more of a carbon monoxide level associated with the user, a heart rate for the user, a skin temperature for the user, and a galvanic skin response for the user.

In an example, the phase may be a first phase, and the processor may be configured to determine the modification the cessation program based on the first phase and the smoking detection event. For example, a cigarette consumption rate for the user may be determined using the smoking detection event. An increase to a duration of the first phase may be determined based on the cigarette consumption rate. The increase to the duration of the first phase may be determined to exceed a threshold. The user may be assigned to a second phase of the cessation program.

In an example, the processor may be configured to determine a biomarker trend may have exceeded a threshold. The biomarker trend may be associated with the biomarker.

In an example, the phase may be a first phase, and the processor may be configured to determine the modification the cessation program based on the first phase and the smoking detection event. For example, the user may be assigned to a second phase of the cessation program when it is determined that the biomarker trend has exceeded the threshold. A rate of cigarette consumption may be determined using the smoking detection event. A duration for the second phase of the cessation program may be determined based on the rate of cigarette consumption.

In an example, the processor may be configured to determine the modification to the cessation program based on the phase and the smoking detection event. A rate of cigarette consumption may be determined using the smoking detection event when it is determined that the biomarker trend has exceeded the threshold. A duration for the phase of the cessation program may be determined based on the rate of cigarette consumption.

A device for providing nicotine replacement therapy may be provided. The device may comprise a processor. The processor may be configured to determine a phase of a cessation program associated with a user. A nicotine consumption detection event may be determined. A modification to the cessation program may be determined based on the phase and the nicotine consumption detection event.

In an example, the phase may be a first phase, and the processor may be configured to determine the modification of the cessation program based on the first phase and the nicotine consumption. The user may be assigned to a second phase of the cessation program when it is determined that the nicotine consumption is below a nicotine threshold for the user. A rate of nicotine consumption may be determined using the nicotine detection event. A duration for the second phase of the cessation program may be determined based on the rate of nicotine consumption.

Figure 36:
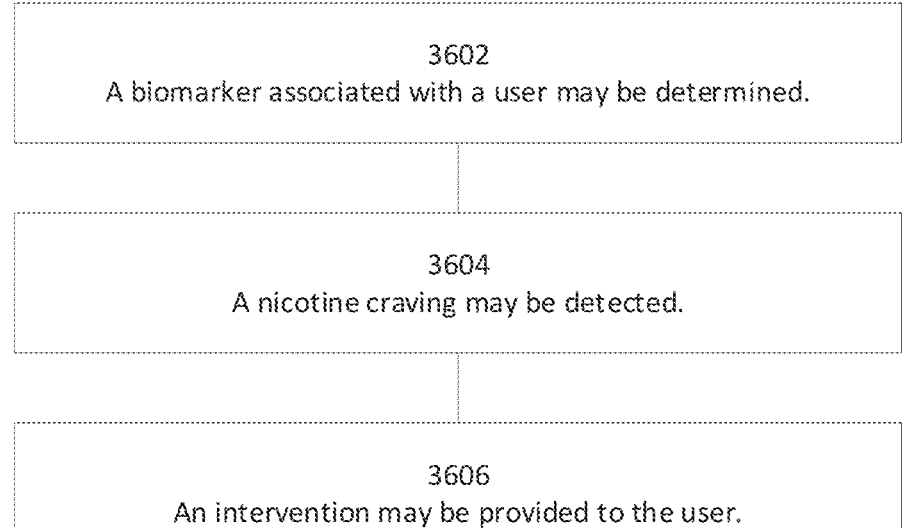
FIG. 36 depicts an example method for providing nicotine replacement therapy that may use a biomarker to detect a nicotine craving.

FIG. 36 depicts an example method for providing nicotine replacement therapy that may use a biomarker to detect a nicotine craving. The method may be performed by a device that comprises a processor that may be configured to perform a one or more actions shown for the method 3600. For example, the device may perform one or more of 3602, 3604, 3606, and/or any combination thereof.

At 3602, a biomarker associated with a user may be determined. The biomarker may be any biomarker described herein.

At 3604, a nicotine craving may be detected. The nicotine craving may be detected using a biomarker. For example, a second biomarker associated with the user may be determined. A predictive value may be calculated based on the first biomarker and/or the second biomarker. The predictive value may indicate a probability that the user may be experiencing a craving for nicotine. It may be determined that the user may be experiencing the nicotine craving when the predictive value exceeds a threshold.

The nicotine craving may be detecting using one or more biomarkers. For example, a galvanic skin response associated with the user may be determined. A heart rate for the user may be determined. A skin temperature for the user may be determined. The nicotine craving may be determined using the galvanic skin response, the heart rate, and the skin temperature.

At 3606, an intervention may be provided to the user. The intervention may be a behavioral intervention, a nicotine replacement therapy intervention, a combination thereof, and/or the like. The intervention may be intended to reduce tobacco consumption, nicotine consumption, electronic cigarette consumption, cigarette consumption, and/or the like.

The intervention to the user may be provided based on the nicotine craving and a phase of the cessation program. The phase of the cessation program may be associated with the user.

The intervention may be provided to the to the user based on the nicotine craving and the phase by sending a notification to the user. The notification may comprise one or more of an indication that the user may dispense a dose of nicotine formulation, a behavioral therapy instruction, an indication of an action the user may take to reduce the nicotine craving, and an indication of the biomarker.

The intervention may be a modification to the cessation program and/or a phase of the cessation program. For example, the intervention may change a duration for the phase may be changed based on a cessation trend.

A device for providing nicotine replacement therapy may be provided. The device may comprise a processor. A biomarker associated with a user may be determined. A nicotine craving may be detected using the biomarker associated with the user. An intervention may be provided to the user based on the nicotine craving.

In an example, the biomarker may be a first biomarker, and the processor may be configured to detect the nicotine craving using the first biomarker and/or a second biomarker. For example, the second biomarker may be associated with the user. A predictive value based on the first biomarker and/or the second biomarker may be determined. The predictive value may indicate a probability that the user may be experiencing a craving for nicotine. It may be determined that the user may be experiencing the nicotine craving when the predictive value exceeds a threshold.

In an example, the biomarker may be a galvanic skin response associated with the user, and the processor may be configured to detect the nicotine craving using the galvanic skin response. A heart rate for the user may be determined. A skin temperature for the user may be determined. The nicotine craving may be detected using the galvanic skin response, the heart rate, and the skin temperature.

In an example, the processor may be configured to determine a phase of a cessation program associated with the user. The intervention to the user may be provided based on the nicotine craving and the phase of the cessation program.

In an example, the intervention may be one or more of a behavioral intervention and a nicotine replacement therapy intervention, and the processor may be configured to provide the intervention to the user based on the nicotine craving and the phase by sending a notification to the user. The notification may comprise one or more of an indication that the user may dispense a dose of nicotine formulation, a behavioral therapy instruction, an indication of an action the user may take to reduce the nicotine craving, and an indication of the biomarker.

In an example, the modification to the cessation program may be based on the intervention, the phase, and the biomarker. In an example, the processor may be configured to determine a cessation trend that may be indicated by the intervention, the phase, and the biomarker. A duration for the phase may be changed based on the cessation trend.

This application may refer to "determining" various pieces of information. Determining the information can include one or more of, for example, estimating the information, calculating the information, predicting the information, or retrieving the information from memory.

Additionally, this application may refer to "receiving" various pieces of information. Receiving is, as with "accessing", intended to be a broad term. Receiving the information can include one or more of for example, accessing the information, or retrieving the information (for example, from memory). Further, "receiving" is typically involved, in one way or another, during operations such as, for example, storing the information, processing the information, transmitting the information, moving the information, copying the information, erasing the information, calculating the information, determining the information, predicting the information, or estimating the information.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as is clear to one of ordinary skill in this and related arts, for as many items as are listed.

We describe a number of examples. Features of these examples can be provided alone or in any combination, across various claim categories and types. Further, embodiments can include one or more of the following features, devices, or aspects, alone or in any combination, across various claim categories and types.

The invention claimed is:

1. A device for providing nicotine replacement therapy, the device comprising:
   a motion sensor for generating a first digital signal that indicates one or more motions associated with a user;
   a receiver for receiving a second digital signal from a nicotine formulation dispenser, wherein the nicotine formulation dispenser comprises a lockout mechanism; and
   a processor, the processor configured to:
      determine a nicotine formulation consumption rate associated with the user based on the second digital signal from the nicotine formulation dispenser;
      determine a smoking detection event when a carbon monoxide saturation level for the user exceeds a threshold;
      determine a rate of cigarette consumption using the smoking detection event;
      determine a fidgeting motion using the first digital signal, wherein the fidgeting motion is predictive of the smoking detection event;
      determine an anticipated craving time based on the fidgeting motion, the nicotine formulation consumption rate, and the rate of cigarette consumption;
      determine an amount of nicotine formulation to reduce a nicotine craving;
      determine a modification to a cessation program based on the anticipated craving time;
      send a third digital signal to the nicotine formulation dispenser to cause the lockout mechanism to move to an operative position, such that the nicotine formulation dispenser can dispense the amount of nicotine formulation to the user at the anticipated craving time to reduce the nicotine craving; and
      send a notification message to the user at the anticipated craving time, wherein the notification message instructs the user to dispense the amount of nicotine formulation from the nicotine formulation dispenser.

2. The device of claim 1, wherein the processor is further configured to determine a marker, and wherein the marker comprises at least one of a cigarette count, nicotine data, a user biomarker, or an indicator of user behavior.

3. The device of claim 1, wherein the processor is further configured to determine a marker, and wherein the marker is at least one of a heart rate, a resting heart rate, a heart rate variability, a blood pressure, a temperature of the user, a respiration rate, an oxygen saturation, a skin temperature, or a galvanic skin response.

4. The device of claim 1, wherein the modification comprises a change to at least one of a rate of reduction of cigarettes, a duration of a phase, a speed at which to reduce cigarettes, a rate of reduction of nicotine replacement therapy, or a speed at which to reduce the nicotine replacement therapy.

5. The device of claim 4, wherein the processor is configured to determine the modification to the cessation program based on the anticipated craving time by determining a cessation trend.

6. A device for providing nicotine replacement therapy, the device comprising:

a motion sensor for generating a first digital signal that indicates one or more motions associated with a user;

a receiver for receiving a second digital signal from a nicotine formulation dispenser, wherein the nicotine formulation dispenser comprises a lockout mechanism;

a processor, the processor configured to:

determine a biomarker associated with a user;

determine a nicotine formulation consumption rate associated with the user based on the second digital signal from the nicotine formulation dispenser;

determine a smoking detection event when a carbon monoxide saturation level for the user exceeds a threshold;

determine a rate of cigarette consumption using the smoking detection event;

determine a fidgeting motion using the first digital signal, wherein the fidgeting motion is predictive of the smoking detection event;

determine an anticipated craving time based on the fidgeting motion, the nicotine formulation consumption rate, and the rate of cigarette consumption;

detect a nicotine craving using the anticipated craving time and the biomarker associated with the user;

determine an amount of nicotine formulation to reduce the nicotine craving;

send a third digital signal to the nicotine formulation dispenser to cause the lockout mechanism to move to an operative position such that the nicotine formulation dispenser can dispense the amount of nicotine formulation to the user at the anticipated craving time to reduce the nicotine craving; and provide an intervention to the user based on the nicotine craving, wherein the intervention comprises a notification message that instructs the user to dispense the amount of nicotine formulation from the nicotine formulation dispenser at the anticipated craving time.

7. The device of claim 6, wherein the biomarker is a first biomarker, and wherein the processor is configured to detect the nicotine craving using the anticipated craving time and the first biomarker associated with the user by:

determining a second biomarker associated with the user;

calculating a predictive value based on the first biomarker and the second biomarker, wherein the predictive value indicates a probability that the user is experiencing the nicotine craving; and determining that the user is experiencing the nicotine craving when the predictive value exceeds a predictive threshold.

8. The device of claim 6, wherein the biomarker is a galvanic skin response, and wherein the processor is configured to detect the nicotine craving using anticipated craving time and the galvanic skin response associated with the user by:

determining a heart rate for the user;

determining a skin temperature for the user; and detecting the nicotine craving using the galvanic skin response, the heart rate, and the skin temperature.

9. The device of claim 6, wherein the notification message further comprises at least one of a behavioral therapy instruction, an indication of an action the user can take to reduce the nicotine craving, or an indication of the biomarker.

10. The device of claim 6, wherein the processor is further configured to determine a cessation trend indicated by the biomarker.

11. A device for providing nicotine replacement therapy, the device comprising:

a motion sensor for generating a first digital signal that indicates one or more motions associated with a user;

a receiver for receiving a second digital signal from a nicotine formulation dispenser, wherein the nicotine formulation dispenser comprises a lockout mechanism; and a processor, the processor configured to:

determine a nicotine formulation consumption rate associated with the user based on the second digital signal from the nicotine formulation dispenser;

determine a smoking detection event when a carbon monoxide saturation level for the user exceeds a threshold;

determine a rate of cigarette consumption using the smoking detection event;

determine a fidgeting motion using the first digital signal, wherein the fidgeting motion is predictive of the smoking detection event;

determine an anticipated craving time based on the fidgeting motion, the nicotine formulation consumption rate, and the rate of cigarette consumption;

determine a duration for a phase of a cessation program based on the anticipated craving time and the rate of cigarette consumption;

determine an amount of nicotine formulation to reduce a nicotine craving;

determine a modification to a cessation program based on the anticipated craving time, the phase, and the duration;

send a third digital signal to the nicotine formulation dispenser to cause the lockout mechanism to move to an operative position such that the nicotine formulation dispenser can dispense the amount of nicotine formulation to the user at the anticipated craving time to reduce the nicotine craving; and send a notification message to the user at the anticipated craving time, wherein the notification message instructs the user to dispense the amount of nicotine formulation from the nicotine formulation dispenser.

12. The device of claim 11, wherein the processor is further configured to determine a biomarker, and wherein the biomarker is at least one of a heart rate for the user, a skin temperature for the user, or a galvanic skin response for the user.

13. The device of claim 11, wherein the phase is a first phase, and wherein the processor is further configured to:

determine an increase to the duration based on at least the cigarette consumption rate;

determine the increase to the duration would exceed a duration threshold; and assign the user to a second phase of the cessation program.

14. The device of claim 11, wherein the phase is a first phase, wherein the duration is a first duration, and wherein the processor is configured to:

assign the user to a second phase of the cessation program when it is determined that a biomarker trend has exceeded a biomarker threshold; and determine a second duration for the second phase of the cessation program based on at least the cigarette consumption rate.

15. A device for providing nicotine replacement therapy, the device comprising:
 a motion sensor for generating a first digital signal that indicates one or more motions associated with a user;
 a receiver for receiving a second digital signal from a nicotine formulation dispenser;
 a processor, the processor configured to:
  determine a carbon monoxide saturation level for the user;
  determine a nicotine formulation consumption rate associated with the user based on the second digital signal from the nicotine formulation dispenser;
  determine a smoking detection event when the carbon monoxide saturation level exceeds a threshold;
  determine fidgeting motion using the first digital signal, wherein the fidgeting motion is predictive of the smoking detection event;
  determine an anticipated craving time based on the fidgeting motion, the nicotine formulation consumption rate, and a rate of cigarette consumption;
  determine an amount of nicotine formulation to reduce a nicotine craving;
 send a third digital signal to the nicotine formulation dispenser to cause a lockout mechanism to move to an operative position such that the nicotine formulation dispenser can dispense the amount of nicotine formulation to the user at the anticipated craving time to reduce the nicotine craving; and
 send a notification message to the user at the anticipated craving time, wherein the notification message instructs the user to dispense the amount of nicotine formulation from the nicotine formulation dispenser.

16. The device of claim 15, wherein the processor is further configured to:
 determine a phase of a cessation program associated with a user;
 determine a duration for a first phase of the cessation program based on the anticipated craving time and the rate of cigarette consumption;
 determine a modification to the cessation program based on the phase, the duration, the anticipated craving time, and the smoking detection event;
 assign the user to a second phase of the cessation program when it is determined that a nicotine consumption is below a nicotine threshold for the user;
 determine a rate of nicotine consumption using the smoking detection event and the nicotine formulation consumption rate; and
 determine a second duration for the second phase of the cessation program based on the rate of nicotine consumption.

* * * * *